US012516335B2

(12) United States Patent
Pacheco Villalobos et al.

(10) Patent No.: US 12,516,335 B2
(45) Date of Patent: Jan. 6, 2026

(54) REGENERATION OF GENETICALLY MODIFIED PLANTS

(71) Applicants: KWS SAAT SE & Co. KGaA, Einbeck (DE); BASF SE, Ludwigshafen (DE)

(72) Inventors: David Pacheco Villalobos, Einbeck (DE); Wolfgang Koch, Einbeck (DE); Bruno Pollet, Nevele (BE); Oliver Schmitz, Berlin (DE); Jixiang Kong, Einbeck (DE); Susana Martin-Ortigosa, Einbeck (DE)

(73) Assignees: BASF SE, Ludwigshafen (DE); KWS SAAT SE & Co. KgaA, Einbeck (DE)

( * ) Notice: Subject to any disclaimer, the term of this patent is extended or adjusted under 35 U.S.C. 154(b) by 0 days.

(21) Appl. No.: 16/959,555

(22) PCT Filed: Dec. 31, 2018

(86) PCT No.: PCT/EP2018/086902
§ 371 (c)(1),
(2) Date: Jul. 1, 2020

(87) PCT Pub. No.: WO2019/134884
PCT Pub. Date: Jul. 11, 2019

(65) Prior Publication Data

US 2021/0079409 A1 Mar. 18, 2021

(30) Foreign Application Priority Data

Jan. 3, 2018 (EP) .................................... 18150187

(51) Int. Cl.
*C12N 15/82* (2006.01)
*A01H 4/00* (2006.01)

(52) U.S. Cl.
CPC ......... *C12N 15/8205* (2013.01); *A01H 4/008* (2013.01); *C12N 15/8201* (2013.01)

(58) Field of Classification Search
CPC ........................ C12N 15/8201; C12N 15/8205
See application file for complete search history.

(56) References Cited

U.S. PATENT DOCUMENTS

2002/0046419 A1 4/2002 Choo et al.
2013/0117891 A1* 5/2013 Inze .................. C12N 15/8294 800/290
2016/0201076 A1 7/2016 Ge et al.

FOREIGN PATENT DOCUMENTS

CN 103597082 A 2/2014
JP 2010-538670 A 12/2010
WO WO-03/004659 A2 1/2003
WO WO-2009037338 A1 * 3/2009 ........... C07K 14/415
WO WO-2012168124 A1 12/2012

OTHER PUBLICATIONS

Debernardi et al (A GRF-GIF chimeric protein improves the regeneration efficiency of transgenic plants. Nature Biotechnology, 38, 1274-1279, 2020) (Year: 2020).*
(Milne et al (An approach to gene-specific transcription inhibition using oligonucleotides complementary to the template strand of the open complex. PNAS. 97:3136-3141, 2000) (Year: 2000).*
Zhang et al (Predicting DNA Hybridization Kinetics from Sequence. Nature Chemistry. 10:91-98, 2018). (Year: 2018).*
Friedberg (Automated protein function prediction—the genomic challenge. Brief. Bioinformatics. 7:225-242, 2006) (Year: 2016).*
Wang et al (From Protein Sequence to Protein Function via Multi-Label Linear Discriminant Analysis. IEEE/ACM Transactions on Computational Biology and Bioinformatics, vol. 14, No. 3, 503-513, 2017). (Year: 2017).*
Kim et al (The AtGRF family of putative transcription factors is involved in leaf and cotyledon growth in *Arabidopsis*. Plant J, 36:94-104, 2003). (Year: 2003).*
Gliwicka et al (Extensive Modulation of the Transcription Factor Transcriptome during Somatic Embryogenesis in *Arabidopsis thaliana*. PLOS ONE 1-20, 2013). (Year: 2013).*
Lowe et al (Morphogenic Regulators Baby boom and Wuschel Improve Monocot Transformation. The Plant Cell, vol. 28: 1998-2015, Sep. 2016) (Year: 2016).*
Lowe et al (Morphogenic Regulators Baby boom and Wuschel Improve Monocot Transformation. The Plant Cell, vol. 28, p. 1998-2015, 2016) (Year: 2016).*
Boccacci et al (Cultivar-specific gene modulation in Vitis vinifera: analysis of the promoters regulating the expression of WOX transcription Factors. Nature Scientific Report, p. 1-13, 2017) (Year: 2017).*
Horiguchi et al (The transcription factor AtGRF5 and the transcription coactivator AN3 regulate cell proliferation in leaf primordia of *Arabidopsis thaliana*. The Plant Journal 43, 68-78, 2005) (Year: 2005).*
Phytozome Gene Report_AT3G13960.1_PFAM PF08880_ PFAM PF08879_2023. (Year: 2023).*
Huang et al (Genome-wide analysis of growth-regulating factors (GRFs) in Triticum aestivum. PeerJ, p. 1-24, 2021) (Year: 2021).*
Cheng et al., Multiplexed activation of endogenous genes by CRISPR-on, an RNA-guided transcriptional activator system, Cell Res., 23(10):1163-71 (2013).
Dejonghe et al., Plant Chemical Genetics: From Phenotype-Based Screens to Synthetic Biology, Plant Physiol., 174(1):5-20 (2017).
Forster et al., The resurgence of haploids in higher plants, TRENDS in Plant Science, 12(8):368-75 (2007).
Hilton et al., Epigenome editing by a CRISPR-Cas9-based acetyltransferase activates genes from promoters and enhancers, Nat. Biotechnol., 33(5):510-7 (2015).

(Continued)

*Primary Examiner* — Wayne Zhong
(74) *Attorney, Agent, or Firm* — MARSHALL, GERSTEIN & BORUN LLP

(57) ABSTRACT

The present invention relates to the field of plant breeding and in particular to the generation of plants from cells and other tissues. More particularly, the invention provides methods and means for improving plant regeneration, especially from transformed or genetically modified plant cells.

16 Claims, 13 Drawing Sheets

Figure 1:
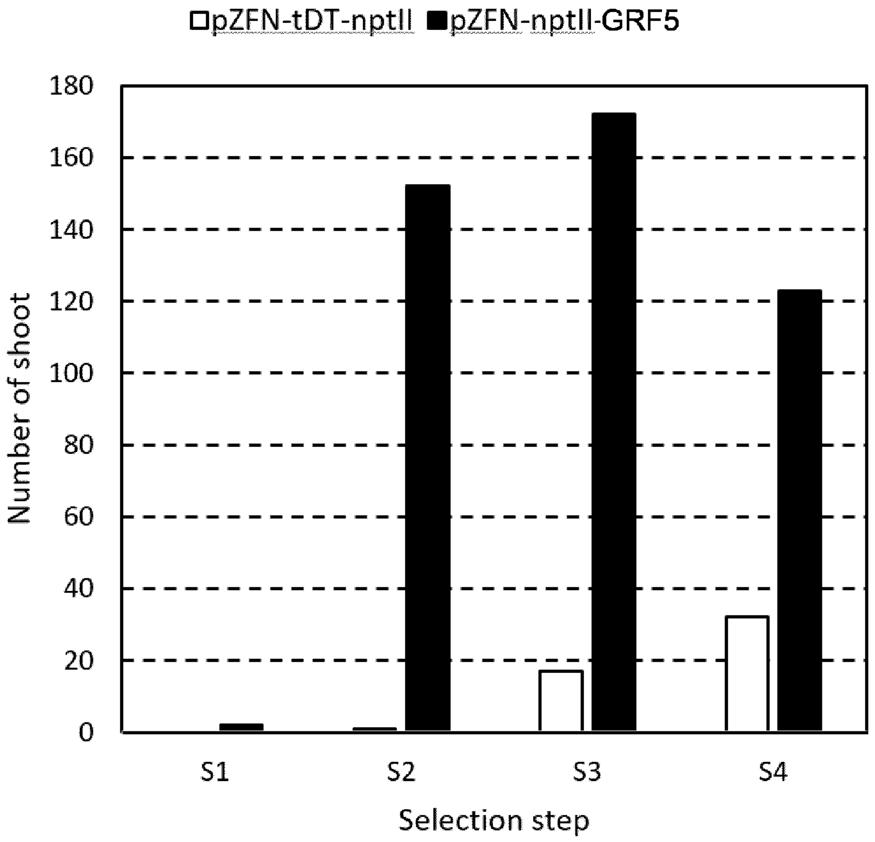

Specification includes a Sequence Listing.

(56) References Cited

OTHER PUBLICATIONS

Kamasumi et al., Chemical genetics: elucidating biological systems with small-molecule compounds, J. Invest. Dermatol., 127(7):1577-84 (2007).
Kishchenko et al., Production of transgenetic sugarbeet (*Beta vulgaris* L.) plants resistant to phosphinothricin, Cell Biol. Int., 29(1):15-9 (2005).
Kujit et al., Interaction between the Growth-Regulating Factor and Knotted1-Like Homeobox families of transcription factors, Plant Physiol., 164(4):1952-66 (2014).
Lindsey et al., Transformation of Sugarbeet (Beta vulgaris) by Agrobacterium tumefaciens, J. Exp. Botany, 41(226):529-36 (1990).
Lowder et al., Multiplexed Transcriptional Activation or Repression in Plants Using CRISPR-dCas9-Based Systems, Methods Mol. Biol., 1629:167-184 (2017).
Moore et al., Transcription activator-like effectors: A toolkit for synthetic biology, ACS Synth. Biol., 3:708-16 (2014).
Rodriguez et al., Control of cell proliferation in *Arabidopsis thaliana* by microRNA miR396, Development, 137(1):103-12 (2010).
Rose et al., Chapter I: Developmental biology of somatic embryogenesis, IN: Pus et al. (eds.), Plant Developmental Biology—Biotechnological Perspectives, vol. 2 (2010).
Segui-Simarro, Androgenesis revisited, Bot. Rev., 76:377-404 (2010).
Van der Knaap et al., A novel gibberellin-induced gene from rice and its potential regulatory role in stem growth, Plant Physiology, 122:695-704 (Mar. 2000).
Vercruyssen et al., Growth Regulating Factor5 stimulates Arabidopsis chloroplast division, photosynthesis, and leaf longevity, Plant Physiol., 167(3):817-32 (2015).
Gaj, Factors influencing somatic embryogenesis induction and plant regeneration with particular reference to *Arabidopsis thaliana* (L.) Heynh, Plant Growth Regulation, 43(1):27-47 (2004).
Horiguchi et al., The Transcription Factor AtGRF5 and the Transcription Coactivator AN3 Regulate Cell Proliferation in Leaf Primordia of *Arabidopsis thaliana*, Plant J., 43(1):68-78 (2005).
International Application No. PCT/EP2018/086902, International Search Report and Written Opinion, mailed Feb. 14, 2019.
Kim et al., The AtGRF Family of Putative Transcription Factors Is Involved in Leaf and Cotyledon Growth in *Arabidopsis*, Plant J., 36(1):94-104 (2003).
Vercruyssen et al., Combining Enhanced Root and Shoot Growth Reveals Cross Talk Between Pathways That Control Plant Organ Size in *Arabidopsis*, Plant Physiol., 155(3):1339-52 (2011).
Li (ed.), General Common Knowledge: Cell Engineering (2008).
Wu et al., Overexpression of the maize GRF10, an endogenous truncated growth-regulating factor protein, leads to reduction in leaf size and plant height, Journal of Integrative Plant Biology, 56(11):1053-63 (Nov. 2014).
Wang et al., Genome-wide identification and analysis of the growth-regulating factor family in Chinese cabbage (*Brassica rapa* L. ssp. *pekinensis*), BMC Genomics, 15:507 (2014).
Choi et al., Whole genome analysis of the OsGRF gene family encoding plant-specific putative transcription activators in rice (*Oryza sativa* L.), Plant Cell Physiol., 45(7):897-904 (2004).
Kong et al., "Overexpression of the Transcription Factor Growth-Regulating Factor5 Improves Transformation of Dicot and Monocot Species," Front. Plant Scie. 11:572319 (2020).

* cited by examiner

Fig. 2
A
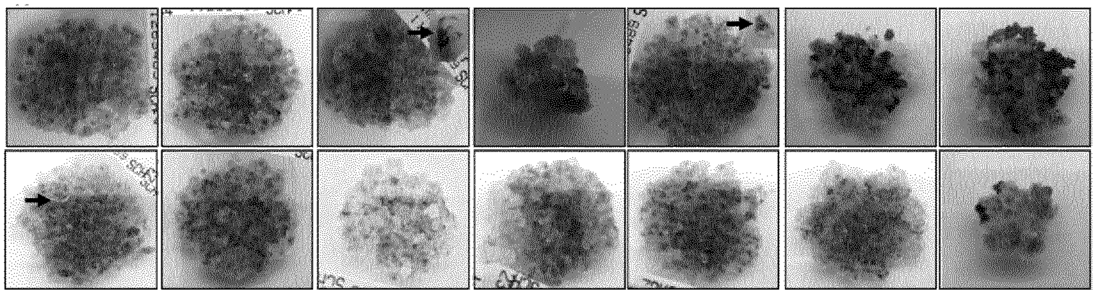
B
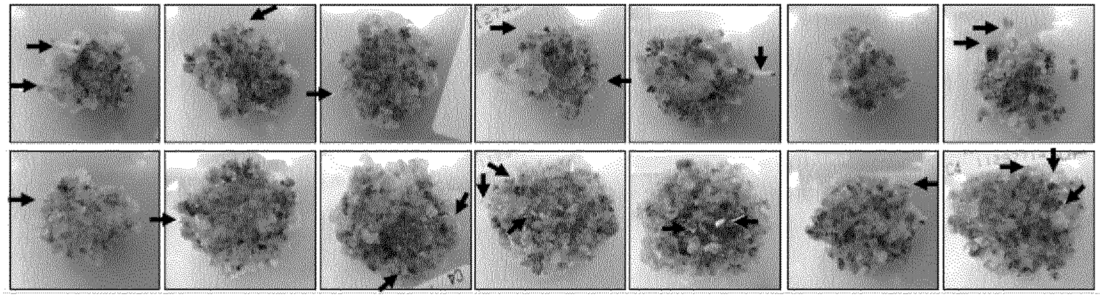

Fig. 3
A
pABM70S.1-GRF5-2014 + pUbi-tDT-nptII (1:1)
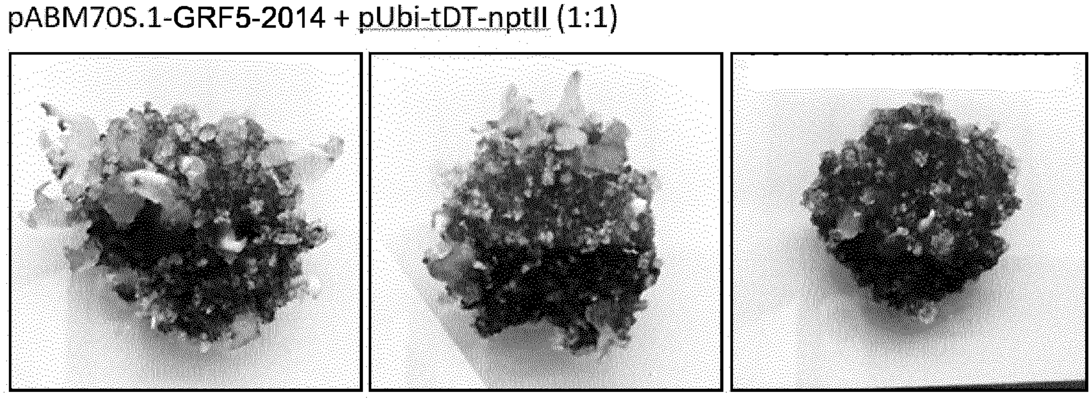
B
pABM70S-TurboYFP-2014 + pUbi-tDT-nptII (1:1)
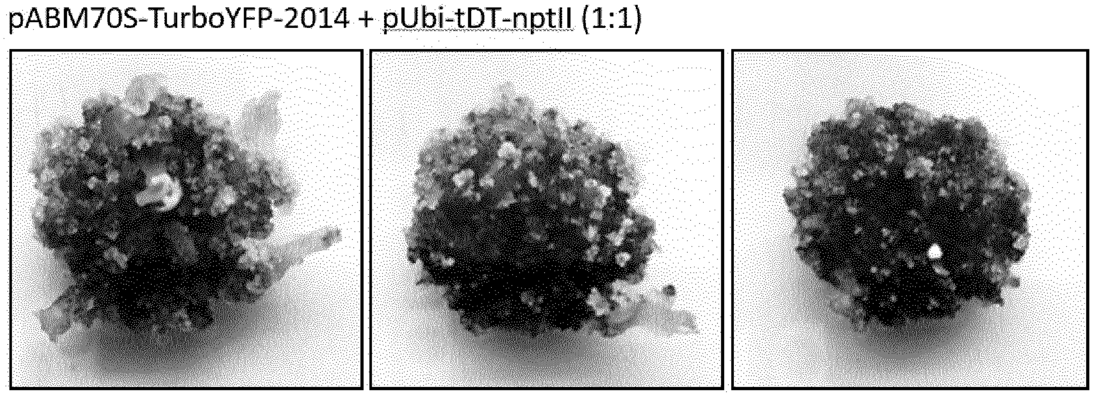

Fig. 5

A

```
AtGRF1_AT2G22840.1 : DPEPGRCRRTDGKKWRCSRDAVPDQKYCERHINRGRHR
AtGRF2_AT4G37740.1 : DPEPGRCRRTDGKKWRCSRDAVPDQKYCERHINRGRHR
AtGRF3_AT2G36400.1 : DPEPGRCRRTDGKKWRCSRDVFAGHKYCERHMHRGRNR
AtGRF4_AT3G52910.1 : DPEPGRCKRTDGKKWRCSRDVVAGHKYCDRHIHRGRNR
AtGRF6_AT2G06200.1 : DAEPGRCRRTDGKKWRCSKEAYPDSKYCERHMHRGKNR
AtGRF7_AT5G53660.1 : DLEPGRCRRTDGKKWRCAKEVVSNHKYCEKHLHRGRPR
AtGRF8_AT4G24150.1 : DLEPWRCKRTDGKKWRCSRNVIPDQKYCERHT-KSRPR
AtGRF9_AT2G45480.1 : ETEPTRCRRTDGKKWRCSNTVLLFEKYCERHMHRGRKR
SEQ ID NO: 2       : DPEPGRCRRTDGKKWRCSREAYPDSKYCEKHMHRGRNR
SEQ ID NO: 4       : DPEPGRCRRTDGKKWRCSKEAYPDSKYCERHMHRGKNR
SEQ ID NO: 6       : DPEPGRCRRTDGKKWRCSKEAYPDSKYCEKHMHRGKNR
SEQ ID NO: 8       : DPEPGRCRRTDGKKWRCSKEAYPDSKYCEKHMHRGKNR
SEQ ID NO: 10      : DPEPGRCRRTDGKKWRCSREAYPDSKYCEKHMHRGRNR
SEQ ID NO: 12      : DPEPGRCRRTDGKKWRCSREAHPDSKYCEKHMHRGRNR
SEQ ID NO: 14      : DPEPGRCRRTDGKKWRCSREAYPDSKYCEKHMHRGRNR
SEQ ID NO: 16      : DPEPGRCRRTDGKKWRCSREAYPDSKYCEKHMHRGRNR
SEQ ID NO: 18      : DPEPGRCRRTDGKKWRCSKEAYPDSKYCEKHMHRGKNR
SEQ ID NO: 20      : DPEPGRCRRTDGKKWRCSKEAYPDSKYCERHMHRGRNR
SEQ ID NO: 22      : DPEPGRCRRTDGKKWRCAKDAYPDSKYCERHMHRGRNR
SEQ ID NO: 24      : DPEPGRCRRTDGKKWRCSREAYPDSKYCEKHMHRGKNR
SEQ ID NO: 26      : DPEPGRCRRTDGKKWRCSKEAYPDSKYCEKHMHRGKNR
SEQ ID NO: 28      : DPEPGRCRRTDGKKWRCSKEAYPDSKYCERHMHRGRNR
SEQ ID NO: 30      : DPEPGRCRRTDGKKWRCSKEAYPDSKYCERHMHRGRNR
SEQ ID NO: 32      : DPEPGRCRRTDGKKWRCSKEAYPDSKYCEKHMHRGKNR
SEQ ID NO: 106     : DPEPGRCRRTDGKKWRCSKEAYPDSKYCERHMHRGRNR
SEQ ID NO: 108     : DPEPGRCRRTDGKKWRCSREAYPDSKYCEKHMHRGRNR
SEQ ID NO: 110     : DLEPGRCRRTDGKKWRCSKEAYPDSKYCERHMHRGRNR
SEQ ID NO: 112     : DPEPGRCRRTDGKKWRCSKEAYPDSKYCEKHMHRGKNR
                     DPEPGRCRRTDGKKWRCSKEAYPDSKYCEKHMHRGKNR

motif              : DPEPGRCRRTDGKKWRCSREAYPDSKYCEKHMHRGRNR
                      L               AKD H         R     K
```

Fig. 5

B

| *Hit_ID* | *Hit Count* | *start* | *stop* | *mis-matches* | *Hit_sequence_region* |
|---|---|---|---|---|---|
| AtGRF1_AT2G22840.1 | 1 | 196 | 233 | 5 | DPEPGRCRRTDGKKWRCSRDAVPDQKYCERHINRGRHR |
| AtGRF2_AT4G37740.1 | 1 | 227 | 264 | 5 | DPEPGRCRRTDGKKWRCSRDAVPDQKYCERHINRGRHR |
| AtGRF3_AT2G36400.1 | 1 | 144 | 181 | 5 | DPEPGRCRRTDGKKWRCSRDVFAGHKYCERHMHRGRNR |
| AtGRF4_AT3G52910.1 | 1 | 151 | 188 | 8 | DPEPGRCKRTDGKKWRCSRDVVAGHKYCDRHIHRGRNR |
| AtGRF6_AT2G06200.1 | 1 | 80 | 117 | 1 | DAEPGRCRRTDGKKWRCSKEAYPDSKYCERHMHRGKNR |
| AtGRF7_AT5G53660.1 | 1 | 107 | 144 | 7 | DLEPGRCRRTDGKKWRCAKEVVSNHKYCEKHLHRGRPR |
| AtGRF9_AT2G45480.1 | 1 | 305 | 342 | 10 | DNEPGRCRRTDGKKWRCSKDVLSGQKYCDKHMHRGMKK |
| SEQ ID NO: 2 | 1 | 81 | 118 | 0 | DPEPGRCRRTDGKKWRCSREAYPDSKYCEKHMHRGRNR |
| SEQ ID NO: 4 | 1 | 87 | 124 | 0 | DPEPGRCRRTDGKKWRCSKEAYPDSKYCERHMHRGKNR |
| SEQ ID NO: 6 | 1 | 90 | 127 | 0 | DPEPGRCRRTDGKKWRCSKEAYPDSKYCEKHMHRGKNR |
| SEQ ID NO: 8 | 1 | 93 | 130 | 0 | DPEPGRCRRTDGKKWRCSKEAYPDSKYCEKHMHRGKNR |
| SEQ ID NO: 10 | 1 | 81 | 118 | 0 | DPEPGRCRRTDGKKWRCSREAYPDSKYCEKHMHRGRNR |
| SEQ ID NO: 12 | 1 | 81 | 118 | 0 | DPEPGRCRRTDGKKWRCSREAHPDSKYCEKHMHRGRNR |
| SEQ ID NO: 14 | 1 | 81 | 118 | 0 | DPEPGRCRRTDGKKWRCSREAYPDSKYCEKHMHRGRNR |
| SEQ ID NO: 16 | 1 | 81 | 118 | 0 | DPEPGRCRRTDGKKWRCSREAYPDSKYCEKHMHRGRNR |
| SEQ ID NO: 18 | 1 | 89 | 126 | 0 | DPEPGRCRRTDGKKWRCSKEAYPDSKYCEKHMHRGKNR |
| SEQ ID NO: 20 | 1 | 87 | 124 | 0 | DPEPGRCRRTDGKKWRCSKEAYPDSKYCERHMHRGRNR |
| SEQ ID NO: 22 | 1 | 71 | 108 | 0 | DPEPGRCRRTDGKKWRCAKDAYPDSKYCERHMHRGRNR |
| SEQ ID NO: 24 | 1 | 93 | 130 | 0 | DPEPGRCRRTDGKKWRCSREAYPDSKYCEKHMHRGKNR |
| SEQ ID NO: 26 | 1 | 93 | 130 | 0 | DPEPGRCRRTDGKKWRCSKEAYPDSKYCEKHMHRGKNR |
| SEQ ID NO: 28 | 1 | 78 | 115 | 0 | DPEPGRCRRTDGKKWRCSKEAYPDSKYCERHMHRGRNR |
| SEQ ID NO: 30 | 1 | 74 | 111 | 0 | DPEPGRCRRTDGKKWRCSKEAYPDSKYCERHMHRGRNR |
| SEQ ID NO: 32 | 1 | 90 | 127 | 0 | DPEPGRCRRTDGKKWRCSKEAYPDSKYCEKHMHRGKNR |
| SEQ ID NO: 106 | 1 | 78 | 115 | 0 | DPEPGRCRRTDGKKWRCSKEAYPDSKYCERHMHRGRNR |
| SEQ ID NO: 108 | 1 | 81 | 118 | 0 | DPEPGRCRRTDGKKWRCSREAYPDSKYCEKHMHRGRNR |
| SEQ ID NO: 110 | 1 | 94 | 131 | 0 | DLEPGRCRRTDGKKWRCSKEAYPDSKYCERHMHRGRNR |
| SEQ ID NO: 112 | 1 | 89 | 126 | 0 | DPEPGRCRRTDGKKWRCSKEAYPDSKYCEKHMHRGKNR |
| SEQ ID NO: 209 | 1 | 90 | 127 | 0 | DPEPGRCRRTDGKKWRCSKEAYPDSKYCEKHMHRGKNR |

Fig. 9
A
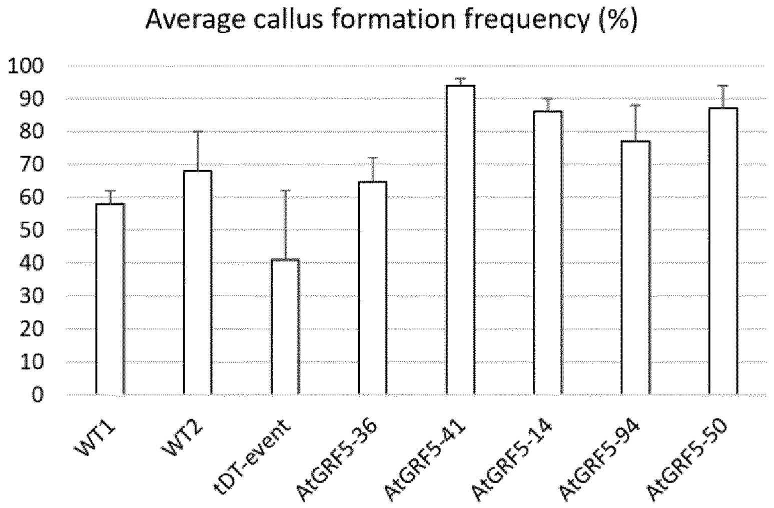
B
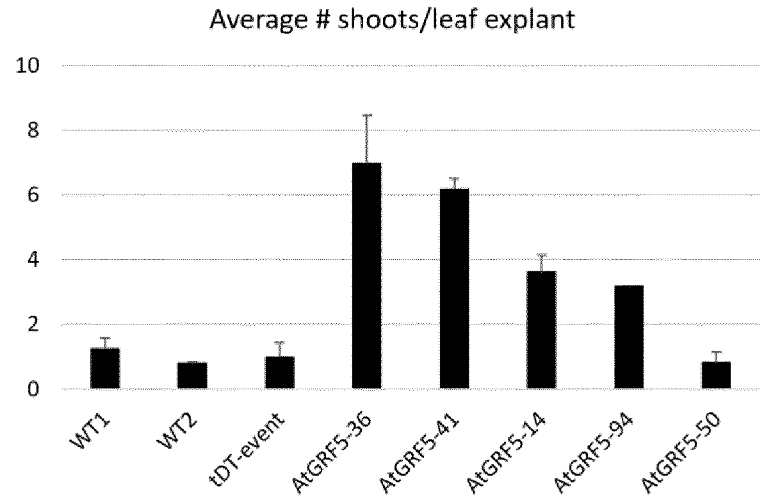
C
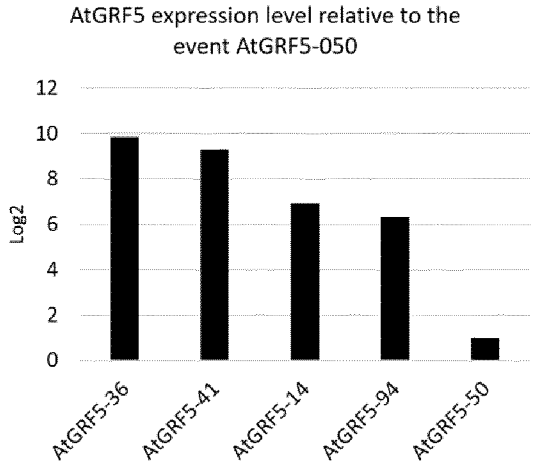

REGENERATION OF GENETICALLY MODIFIED PLANTS

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "W55811_Seqlisting.txt", which was created on Jun. 17, 2020 and is 207,509 bytes in size. The subject matter of the Sequence Listing is incorporated herein in its entirety by reference.

The present invention relates to the field of plant breeding and biotechnology and in particular to the generation of plants from cells and other tissues. More particularly, the invention provides methods and means for improving plant regeneration, especially from transformed or genetically modified plant cells.

In plant breeding, the process of manipulation of plant species has been practiced since near the beginning of human civilization in order to create desired genotypes and phenotypes for specific purposes. With the development of genetic engineering, this field of agriculture has significantly changed during the last decades. A variety of methods for plant genetic engineering has been developed. The choice of transformation method depends on a number of variables, primarily the plant species to be transformed, the purpose of the experiment and the availability of the necessary equipment. The vast majority of plant transformation techniques requires the use of explants with high regeneration capacities as starting material. In addition, gene editing constitutes a new molecular biological method by means of which specific modifications such as insertions, deletions or point mutations or combinations thereof can be introduced into the genome of a plant. To this end, specific molecular instruments are required which firstly have nuclease activity, but above all can be guided to the target sequence to be modified with sufficient specificity to program and carry out a specific and site-directed mutagenesis. In the past few years in plant biotechnology, specific genome editing has developed into an alternative to conventional breeding and to transgenic strategies. However, tools which are currently available, such as meganucleases, zinc finger nucleases (ZFNs), "transcription activator-like effector nucleases" (TALENs) or CRISPR systems are only used in plant biotechnology to a limited extent because of limited regeneration capacities of edited starting material of plants.

A wide variety of cells have the potential to develop into embryos, including haploid gametophytic cells, such as the cells of pollen and embryo sacs (see Forster, B. P., et al. (2007) Trends Plant Sci. 12: 368-375 and Segui-Simarro, J. M. (2010) Bot. Rev. 76: 377-404), as well as somatic cells derived from all three fundamental tissue layers of the plant (Gaj, M. D. (2004) Plant Growth Regul. 43: 27-47 or Rose, R., et al. (2010) "*Developmental biology of somatic embryogenesis*" in: Plant Developmental Biology-Biotechnological Perspectives, Pua E-C and Davey M R, Eds. (Berlin Heidelberg: Springer), pp. 3-26).

The ability to regenerate into plants is often limited to particular genotypes in a certain plant species and weakened in transformed and genetically modified plant cells and other precursor tissues. Even if the step of transformation and genetic modification of a plant cell is successful, this does not necessarily mean that the desired plants can actually be obtained from the modified cells. It is assumed that the treatment, which the plant cells and other precursor tissues are subjected to in order to achieve a genetic modification, affects plant development and regeneration. Thus, it is an object of the present invention to improve efficacy of previously known methods for generating transgenic and genetically modified plants and to support the regeneration of plants from modified plant cells and other plant precursors.

In the present invention, it was surprisingly found that the *Arabidopsis* gene GRF5 (GROWTH-REGULATING FACTOR 5) has an effect in boosting plant regeneration that has never been reported for this gene or its counterparts of the GRF gene family.

In van der Knaap et al. (2000; "A novel gibberellin-induced gene from rice and its potential regulatory role in stem growth", *Plant physiology,* 122(3), 695-704.) the authors have identified and characterized the first member of the GRF gene family in rice (OsGRF1). This was a gibberellic acid-induced gene in intercalary meristems. Overexpression in *Arabidopsis* caused impaired stem growth, female sterility and reduced male fertility. Application of gibberellic acid could not recover the stem elongation defect of transformed plants, suggesting that OsGRF1 could participate in the GA-induced stem elongation. In 2003 Kim et al. ("The AtGRF family of putative transcription factors is involved in leaf and cotyledon growth in *Arabidopsis", The Plant Journal,* 36(1), 94-104.) have characterized the *Arabidopsis* GRF family and determined that the genes are mainly expressed in actively growing tissues. Analysis of null mutants and transgenic plants overexpressing AtGRF1 and AtGRF2 indicated that some members of the GRF family are involved in the regulation of cell expansion during leaf and cotyledon growth. In addition, overexpressor plants showed delayed bolting time, revealing a putative role in flowering. In a study to determine the molecular mechanisms that coordinate cell proliferation in developing leaves, Rodriguez et al. discovered that the miR396 antagonizes the expression pattern of its targets, the GRF transcription factors, in *Arabidopsis* ((2010), "Control of cell proliferation in *Arabidopsis thaliana* by microRNA miR396*", Development,* 137(1), 103-112.). Thus, the balance between miR396 and the GRFs controls the final number of cells in leaves. Furthermore, the authors showed that miR396-targeted GRFs can regulate the size of the shoot apical meristem.

In 2005, Horiguchi et al. ("The transcription factor AtGRF5 and the transcription coactivator AN3 regulate cell proliferation in leaf primordia of *Arabidopsis thaliana", The Plant Journal,* 43(1), 68-78.) first characterized AtGRF5 and its interacting partner ANGUSTFOLA3 (AN3). Knock-out mutants atgrf5 and an3 developed narrow leaves due to decreased cell number, whereas cell proliferation in leaf primordia was enhanced in AtGRF5 and AN3 overexpressor lines. Kuijt et al. ((2014), "Interaction between the GROWTH-REGULATING FACTOR and KNOTTED1-LIKE HOMEOBOX Families of Transcription Factors", Plant physiology, 164(4), 1952-1966.) showed that members of the GRF family act as players in the network controlling the expression of KNOTTED1-LIKE HOMEBOX (KNOX) genes which are involved in restriction of cell differentiation in the shoot apical meristem. AtGRF4, AtGRF5 and AtGRF6 are able to bind to the promoter of a KNOX gene, repressing its expression. *Arabidopsis* seedlings overexpressing AtGRF4, AtGRF5, or AtGRF6 show developmental aberrations in the shoot apical meristem. In a recent study of Vercruyssen et al. ((2015), "Growth regulating factor 5 stimulates *Arabidopsis* chloroplast division, photosynthesis, and leaf longevity", *Plant physiology*, pp-114.) *Arabidopsis* leaves overexpressing GRF5 showed higher chloroplast number per cell, increased chlorophyll content and delayed leaf senescence.

In summary, it is well-known that the *Arabidopsis* gene AtGRF5 and other GRF genes play a role in leaf morphogenesis and stem development. In addition, GRF genes were reported to function in flowering, seed and root development, to control the plant growth under stress conditions and to regulate the plant longevity. However, during their studies, the inventors of the present invention surprisingly found another and novel function of this gene family. GRF5 is capable of providing a positive effect on boosting plant regeneration and thus allowing a more efficient recovery of transgenic plants. The present invention allows to improve the regeneration from diverse tissues or cells (e.g. microspores), may overcome recalcitrance to plant regeneration, in particular genotype dependency, improve the recovery of transgenic plants by e.g. co-expression of gene of interest and GRF5, and of genome-engineered plants by e.g. transient co-expression of genome-editing components and GRF5, as well as shorten the time for the production of transgenic lines and the recovery. Thus, a first aspect of the present invention is the use of GRF5 polypeptide for improving the regenerative ability of a plant.

Any reference hereinafter to a polypeptide or protein useful in the methods of the present invention is taken to mean a GRF5 polypeptide or GRF5 protein as defined herein. Any reference hereinafter to a nucleic acid or polynucleotide useful in the methods of the invention (except for the nucleotide sequence of interest being transformed or the nucleic acid molecule optionally used as repair template for modifying the genome of a plant) is taken to mean a nucleic acid or polynucleotide capable of encoding such a GRF5 polypeptide or GRF5 protein. In one embodiment, any reference to a polypeptide/protein or nucleic acid/polynucleotide useful in the methods of the invention is to be understood to mean proteins or nucleic acids useful in the methods, constructs, expression cassettes, plant cells, plants, seeds, harvestable parts and products of the invention. The nucleic acid/polynucleotide including the mRNA(s) to be introduced into a plant cell or plant (and therefore useful in performing the methods of the invention) is any nucleic acid/polynucleotide encoding the type of polypeptide/protein which will now be described, hereafter also named "GRF5 nucleic acid", "GRF5 polynucleotide", GRF5 gene" or "GRF5 mRNA" or the like.

A "GRF5 polypeptide" or "GRF5 protein" as defined herein refers to any transcription factor preferably a 14-3-3-like protein GF14 upsilon, more preferably comprising a PFAM domain PF08880 (also known as QLQ domain) and a PFAM domain PF08879 (also known as WRC domain) when analyzed with the Interproscan software (www.ebi.ac.uk/interpro), and even more preferably comprises a PFAM domain PF08880 that finds a match of at least 90%, at least 91%, at least 92%, at least 93%, at least 94%, at least 95%, at least 96%, at least 97%, at least 98%, at least 99% or 100% coverage at or near the N-terminus of the GRF5 polypeptide and the PFAM domain PF08879 that finds a match of at least 90%, at least 91%, at least 92%, at least 93%, at least 94%, at least 95%, at least 96%, at least 97%, at least 98%, at least 99% or 100% coverage C-terminally located to the PFAM domain PF08880 of the GRF5 polypeptide, i.e. the amino acid stretch matching PF08879 is located in direction of translation behind the amino acid stretch matching PF08880. Preferably, at least one of the matches has a coverage of at least 95%, at least 96%, at least 97%, at least 98%, at least 99% or 100%.

In one embodiment, both matching amino acid stretches are located in the N-terminal half of the GRF5 polypeptide, preferably the amino acid stretch matching PFAM domain PF08880 is located in the N-terminal quarter of the GRF5 polypeptide. Preferably, the PFAM domain PF08880 matches the amino acid residues of the GRF5 polypeptide starting from residue 5, 6, 7, 8, 9, 10, 11, 12, 13, 14, 15, 16, 17, 18, 19, 20, 21, 22, 23, 24 or 25 of the GRF5 polypeptide, preferably from residue 9, 10, 11, 12, 13, 14, 15, 16, 17, 18, 19, 20 or 21, and the PFAM domain PF08879 matches the amino acid residues of the GRF5 polypeptide starting from residue 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 of the GRF5 polypeptide, preferably from residue 72, 73, 74, 75, 76, 77, 78, 79, 80, 81, 82, 83, 84, 85, 86, 87, 88, 89, 90, 91, 92, 93, 94 or 95. Preferably, the distance between the starting amino acid residue of amino acid stretch matching PFAM domain PF08880 and the starting amino acid residue of amino acid stretch matching PFAM domain PF08879 is 60 to 82 amino acids within the GRF5 polypeptide, more preferably 61 to 75 amino acids, even more preferably 62 to 73 amino acids within the GRF5 polypeptide.

In a further embodiment, the GRF5 polypeptide as used herein comprises the indicator motif: [D]-[PL]-[E]-[P]-[G]-[R]-[C]-[R]-[R]-[T]-[D]-[G]-[K]-[K]-[W]-[R]-[C]-[SA]-[RK]-[ED]-[A]-[YH]-[P]-[D]-[S]-[K]-[Y]-[C]-[E]-[KR]-[H]-[M]-[H]-[R]-[G]-[RK]-[N]-[R], wherein it is allowable/tolerable that the GRF5 polypeptide exhibits a maximum number of three mismatches in comparison with the indicator motif, i.e., up to three mismatches may appear in a sequence alignment between the respective GRF5 polypeptide and the indicator motif, preferably a maximum number of two mismatches in comparison with the indicator motif, i.e., up to two mismatches may appear in a sequence alignment between the respective GRF5 polypeptide and the indicator motif, more preferably a maximum number of one mismatch in comparison with the indicator motif, i.e., only one mismatch may appear in a sequence alignment between the respective GRF5 polypeptide and the indicator motif, and more preferably no mismatch in comparison with the indicator motif. In a particularly preferred embodiment, one of the mismatches or the sole mismatch is located at position 2 of the indicator motif and more preferably the mismatch is [A] instead of [P]. A mismatch means that the amino acid at a certain position according to the indicator motif is replaced by different amino acid or is deleted or shifted by the insertion of at least one additional amino acid. The letters of the indicator motif within square brackets indicate the amino acid residue (one-letter code) and the motif represents the order of the amino acid residues in direction from N-terminus to C-terminus as present in any GRF5 polypeptide of the present invention. If there are two letters within one square bracket they represent alternatives. The motif has been deduced from a comprehensive comparison of the sequences of GRF5 polypeptides derived from 16 different plant species including monocotyledonous and dicotyledonous plants and allows to distinguish GRF5 polypeptides from other members of the GRF protein family like GRF1 (see FIG. 5A). Exemplary motif analysis by sequence alignment/comparison for the determination of the number of mismatches is shown in FIG. 5B. Preferably, the motif is located in the N-terminal half of the GRF5 polypeptide, more preferably the motif is located in the N-terminal half of the GRF5 polypeptide and contains a sub-region of amino acid stretch matching PFAM domain PF08879, i.e. the motif has a sequential overlap with the amino acid stretch matching PFAM domain PF08879. Preferably the indicator motif consists of any of the amino acid sequences SEQ ID NO: 41 to SEQ ID NO: 104 or SEQ ID NO: 113 to SEQ ID NO: 176. Correspondingly the GRF5 polypeptide preferably comprises one contiguous motif consisting of any of the amino acid sequences SEQ ID NO: 41 to SEQ ID NO: 104 or SEQ ID NO: 113 to SEQ ID NO: 176.

Examples of GRF5 polypeptide from various plant species useful in the methods of the present invention are described further below. In Table 1, the locations of the PFAM domain PF08880 and of the PFAM domain PF08879 as well as the individual coverage in any of the presented GRF5 sequences is indicated.

Table 1: Domain analyses in GRF5 polypeptides derived from 16 different plant species GRF5 polypeptide or a GRF5 polypeptide, wherein (i) and (ii) can be introduced in parallel or sequentially in any order, or (a2) introducing into a plant cell at least one nucleotide sequence of interest; and inducing in said plant cell in parallel or sequentially an enhanced expression level of an endogenous gene encoding a GRF5 polypeptide; and (b) optionally cultivating the plant cell of (a1) or (a2) or a plant cell derived from the plant cell of (a1) or (a2) under conditions, where in the plant cell the GRF5 polypeptide is expressed from the expression cassette, the GRF5 polypeptide is translated from introduced mRNA(s), GRF5 polypeptide(s) is enhanced/increased expressed from the endogenous gene, or the GRF5

TABLE 1

Domain analyses in GRF5 polypeptides derived from 16 different plant species

| [SEQ ID NO] | Pfam domain (HMM) | Pfam domain description | Pfam domain length | (i)E_value | score | Pfam domain from | Pfam domain to | sequence from | sequence to | length of Pfam domain covered % |
|---|---|---|---|---|---|---|---|---|---|---|
| 2 | PF08879 | WRC | 43 | 1.60E−20 | 72.5 | 1 | 41 | 82 | 124 | 95 |
| 2 | PF08880 | QLQ | 35 | 7.80E−16 | 57.4 | 1 | 35 | 16 | 50 | 100 |
| 4 | PF08879 | WRC | 43 | 1.10E−20 | 73 | 1 | 43 | 88 | 130 | 100 |
| 4 | PF08880 | QLQ | 35 | 3.00E−16 | 58.8 | 1 | 34 | 20 | 54 | 97 |
| 6 | PF08879 | WRC | 43 | 1.90E−20 | 72.3 | 1 | 43 | 91 | 133 | 100 |
| 6 | PF08880 | QLQ | 35 | 7.00E−14 | 51.2 | 1 | 33 | 19 | 53 | 94 |
| 8 | PF08879 | WRC | 43 | 2.00E−20 | 72.2 | 1 | 43 | 94 | 136 | 100 |
| 8 | PF08880 | QLQ | 35 | 2.20E−15 | 56 | 1 | 34 | 21 | 55 | 97 |
| 10 | PF08879 | WRC | 43 | 1.20E−20 | 72.9 | 1 | 41 | 82 | 124 | 95 |
| 10 | PF08880 | QLQ | 35 | 3.30E−16 | 58.6 | 1 | 35 | 16 | 50 | 100 |
| 12 | PF08879 | WRC | 43 | 1.80E−20 | 72.3 | 1 | 41 | 82 | 124 | 95 |
| 12 | PF08880 | QLQ | 35 | 3.30E−16 | 58.6 | 1 | 35 | 16 | 50 | 100 |
| 14 | PF08879 | WRC | 43 | 1.20E−20 | 72.9 | 1 | 41 | 82 | 124 | 95 |
| 14 | PF08880 | QLQ | 35 | 3.30E−16 | 58.6 | 1 | 35 | 16 | 50 | 100 |
| 16 | PF08879 | WRC | 43 | 1.20E−20 | 72.9 | 1 | 41 | 82 | 124 | 95 |
| 16 | PF08880 | QLQ | 35 | 4.90E−16 | 58.1 | 1 | 35 | 16 | 50 | 100 |
| 18 | PF08879 | WRC | 43 | 1.80E−20 | 72.3 | 1 | 43 | 90 | 132 | 100 |
| 18 | PF08880 | QLQ | 35 | 6.90E−14 | 51.2 | 1 | 33 | 18 | 52 | 94 |
| 20 | PF08879 | WRC | 43 | 2.50E−21 | 75.1 | 1 | 43 | 88 | 130 | 100 |
| 20 | PF08880 | QLQ | 35 | 2.30E−15 | 55.9 | 1 | 34 | 18 | 52 | 97 |
| 22 | PF08879 | WRC | 43 | 2.30E−20 | 72 | 1 | 43 | 72 | 114 | 100 |
| 22 | PF08880 | QLQ | 35 | 8.50E−16 | 57.3 | 1 | 35 | 10 | 44 | 100 |
| 24 | PF08879 | WRC | 43 | 1.10E−20 | 73 | 1 | 43 | 94 | 136 | 100 |
| 24 | PF08880 | QLQ | 35 | 2.20E−15 | 56 | 1 | 34 | 21 | 55 | 97 |
| 26 | PF08879 | WRC | 43 | 1.90E−20 | 72.2 | 1 | 43 | 94 | 136 | 100 |
| 26 | PF08880 | QLQ | 35 | 2.20E−15 | 56 | 1 | 34 | 21 | 55 | 97 |
| 28 | PF08879 | WRC | 43 | 2.80E−21 | 74.9 | 1 | 43 | 79 | 121 | 100 |
| 28 | PF08880 | QLQ | 35 | 8.50E−13 | 47.7 | 1 | 34 | 13 | 47 | 97 |
| 30 | PF08879 | WRC | 43 | 2.30E−21 | 75.2 | 1 | 43 | 75 | 117 | 100 |
| 30 | PF08880 | QLQ | 35 | 2.50E−15 | 55.8 | 2 | 34 | 9 | 43 | 94 |
| 32 | PF08879 | WRC | 43 | 1.90E−20 | 72.3 | 1 | 43 | 91 | 133 | 100 |
| 32 | PF08880 | QLQ | 35 | 3.50E−15 | 55.4 | 1 | 34 | 18 | 52 | 97 |
| 106 | PF08879 | WRC | 43 | 2.80E−21 | 74.9 | 1 | 43 | 79 | 121 | 100 |
| 106 | PF08880 | QLQ | 35 | 8.50E−13 | 47.7 | 1 | 34 | 13 | 47 | 97 |
| 108 | PF08879 | WRC | 43 | 1.20E−20 | 72.9 | 1 | 41 | 82 | 124 | 95 |
| 108 | PF08880 | QLQ | 35 | 3.30E−16 | 58.6 | 1 | 35 | 16 | 50 | 100 |
| 110 | PF08879 | WRC | — | — | — | 2 | 43 | 95 | 137 | — |
| 110 | PF08880 | QLQ | — | — | — | 1 | 37 | 13 | 49 | — |
| 112 | PF08879 | WRC | — | — | — | 1 | 43 | 90 | 131 | — |
| 112 | PF08880 | QLQ | — | — | — | 1 | 33 | 15 | 49 | — |
| 209 | PF08879 | WRC | — | — | — | 1 | 43 | 90 | 131 | — |
| 209 | PF08880 | QLQ | — | — | — | 1 | 33 | 15 | 49 | — |

According to one aspect, the invention provides a method for transforming a plant cell comprising the steps (a1) introducing into a plant cell (i) at least one nucleotide sequence of interest; and (ii) an expression cassette comprising a polynucleotide encoding a GRF5 polypeptide, mRNA(s) encoding polypeptide(s) is (are) present, preferably in an enhanced amount compared to the amount in a wild type plant cell or a plant cell into which the expression cassette comprising a polynucleotide encoding a GRF5 polypeptide, mRNA(s) encoding GRF5 polypeptide or the GRF5 polypeptide(s) has (have) not been introduced according to step (a1) or in which the enhanced expression level of an endogenous gene encoding the GRF5 polypeptide has not been induced according to step (a2).

The methods according to the present invention yields a modified or transformed plant cell having an improved ability of regeneration due to the presence of GRF5 or the presence of GRF5 in an enhanced amount. It is preferred, however, that in the modified plant cell the presence of GRF5 or the presence of GRF5 in an enhanced amount is transient.

Transformation of a plant cell means introducing a nucleic acid molecule into a plant cell in a manner to cause stable integration into the genome of the plant cell or transient appearance in the plant cell leading to expression of the nucleic acid sequence for example constitutively, temporally or specifically related to particular tissue(s) or certain developmental stage(s) et cetera. Transformation and regeneration of both monocotyledonous and dicotyledonous plant cells is now routine, and the selection of the most appropriate transformation technique will be determined by the practitioner. The choice of method will vary with the type of plant or genotype to be transformed; those skilled in the art will recognize the suitability of particular methods for given plant types or genotypes. Suitable methods can include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium*-mediated transformation.

Step (a1) (i) or (a2) of introducing the at least one nucleotide sequence of interest can be performed using any suitable method commonly known in the art. A number of methods is available to transfer nucleic acids of interest into plant cells. An exemplary vector mediated method is *Agrobacterium*-mediated transformation, as described, for example, by Lindsay & Gallois, 1990, Journal of Experimental Botany, and Kischenko et al., 2005, Cell Biology International for sugar beet, by Ishida et al., 2007, ("*Agrobacterium*-mediated transformation of maize." *Nature protocols,* 2(7), 1614-1621) for corn, or by the PureWheat Technology from Japan Tobacco company for wheat. Other suitable techniques include particle bombardment and electroporation.

The nucleotide sequence of interest according to the invention may be a DNA or RNA sequence, e.g. mRNA, siRNA, miRNA etc. More particularly, the nucleotide sequence of interest encodes at least one phenotypic trait. Preferably, the phenotypic trait conferred by the DNA or RNA can be selected from the group consisting of resistance/tolerance to biotic stress, including pathogen resistance/tolerance, wherein the pathogen can be a virus, bacterial, fungal or animal pathogen, resistance/tolerance to abiotic stress including chilling resistance/tolerance, drought stress resistance/tolerance, osmotic resistance/tolerance, heat stress resistance/tolerance, cold or frost stress resistance/tolerance, oxidative stress resistance/tolerance, heavy metal stress resistance/tolerance, salt stress or water logging resistance/tolerance, lodging resistance/tolerance, shattering resistance/tolerance, or resistance/tolerance against one or more herbicides like glyphosate, glufosinate, 2,4-D, Dicamba, ALS inhibitors et cetera. The at least one phenotypic trait of interest can also be selected from the group consisting of the modification of a further agronomic trait of interest including yield increase, flowering time modification, seed color modification, endosperm composition modification, nutritional content modification or metabolic engineering of a pathway of interest.

In context of the present invention, GRF5 can be introduced as an expression cassette comprising a polynucleotide encoding a GRF5 polypeptide, as mRNA encoding a GRF5 polypeptide (including also pre-mRNA or precursor mRNA) or as a GRF5 polypeptide. Exemplary techniques for introducing a nucleic acid molecule are described above. Alternatively, GRF5 can be provided in the plant cell by activating the expression of the endogenous gene encoding for GRF5 polypeptide. This would lead to an enhanced expression level of the endogenous GRF5 gene, i.e. to the presence or occurrence of GRF5 polypeptide in an enhanced amount in the plant cell. The activation of the expression of the endogenous gene can be achieved by modifying the activity or structure of the promoter of the endogenous gene encoding the GRF5 polypeptide. For instances, enhancer elements can be introduced into the promoter by means of gene editing; or either an enhancer element regulating the promoter can be further strengthen or a silencer element regulating the promoter can be weakened by e.g. targeted mutagenesis/modification; or modifications can be introduced into the epigenome related to enhancers by means of gene editing tools like CRISPR systems (Hilton et al. (2015). Epigenome editing by a CRISPR-Cas9-based acetyltransferase activates genes from promoters and enhancers. *Nature biotechnology,* 33(5), 510-517); or synthetic transcription factors based on e.g. TALE activators or dCas9 activators can be introduced into the cell where they are able to bind targeted recognition sites on or near by the promoter und activate transcription of the GRF5 gene (Cheng et al. (2013). Multiplexed activation of endogenous genes by CRISPR-on, an RNA-guided transcriptional activator system. *Cell research,* 23(10), 1163.); or the amount of microRNA (miRNA) in the plant cell regulating the expression of the GRF5 gene by post-transcriptional inhibition can be reduced by e.g. knock out (null mutant) or knock down in order to increase the amount of translated GRF5 polypeptide in the plant cell—for example Rodriguez et al. 2010 (supra) identified in *Arabidopsis* the microRNA miR396 which antagonizes the expression of GRF5 and represents therefore a suitable target for affecting the amount of GRF5 polypeptide in a plant cell.

Figure 4:
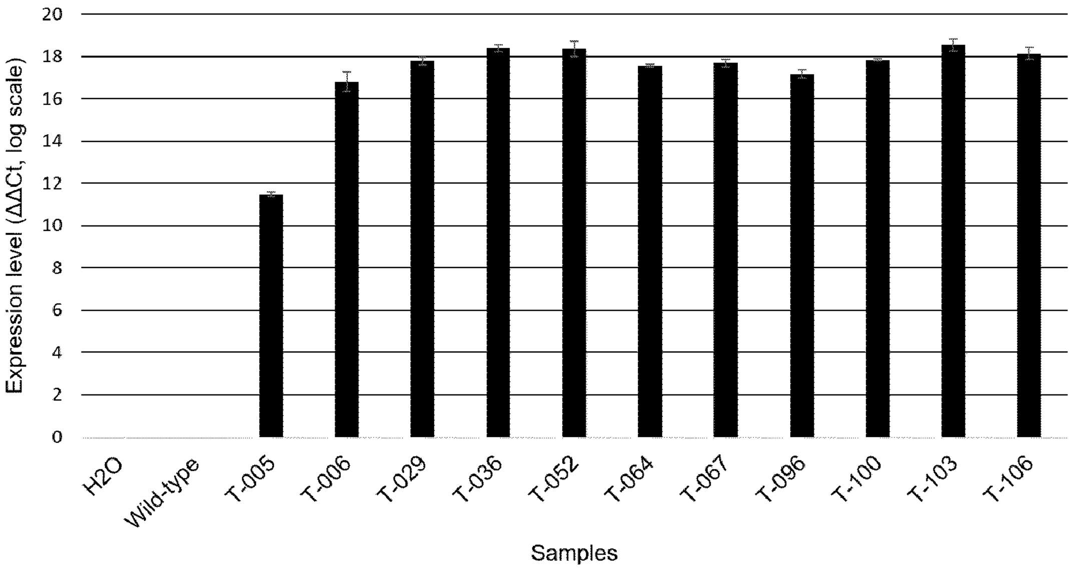

Dependent on the plant species as well as on the cell type different levels of gene or expression activation are needed in order to have adequate amount of GRF5 polypeptide present in the plant cell at the time when regeneration takes place. There are various techniques available to a person skilled in the art in order to measure the actual expression level of an endogenous or an introduced gene, e.g., qPCR, RT-PCR, Northern blot, or microrarrays. Measurement of the expression level of the AtGRF5 gene introduced to a *Beta vulgaris* plant is shown in FIG. 4. These methods allow those skilled in the art by routine work to adjust the level of expression of the GRF5 gene which effects improved regeneration ability from diverse tissues or somatic and reproductive cells (e.g. microspores). In a preferred embodiment, in the plant cell the expression level of an endogenous gene encoding a GRF5 polypeptide is increased at least by the factor of 2, the factor of 3, or the factor of 5, preferably by the factor of 10, the factor of 25 or factor of 50, more preferred by the factor of 100, the factor of 200, or the factor of 500.

As described further above the induction of an enhanced expression level of an endogenous gene in a plant cell can be carried out by the application of one or more activators or a precursor thereof. These can be applied to the medium in which the plant cells are cultivated and is then actively or passively absorbed by the plant cell. Furthermore, the one or more activator or a precursor thereof can be directly introduced into the plant cell by microinjection, electroporation or biolistic bombardment. Beside the above synthetic transcription activators, a number of further activators are known from the state of the art that can be used for increasing the expression level of an endogenous gene, in particular the expression level of the endogenous GRF5 gene: In the recent years, the technical fields of chemical plant genetics and chemical plant biology emerged where biological systems are treated with small molecules to specifically perturb cellular functions. Small molecules are used commercially as drugs, herbicides, and fungicides in different systems, but in recent years they are increasingly exploited also as tools for genetic regulation. For instance, chemical genetics involves the discovery of small-molecule effectors of various cellular functions through screens of compound libraries (Dejonghe & Russinova (2017). Plant Chemical Genetics: From Phenotype-Based Screens to Synthetic Biology. *Plant Physiology*, pp-01805; Kawasumi, M., & Nghiem, P. (2007). Chemical genetics: elucidating biological systems with small-molecule compounds. *Journal of Investigative Dermatology,* 127(7), 1577-1584.). Such small molecule effectors suitable for the activation of the expression of a target gene like GRF5, can be identified by chemical screens following different strategies (Dejonghe & Russinova, 2017). Comprehensive compound libraries are available which allow the simple screening of countless small molecules and the identification of effectors which can be used for activation of the gene expression of genes like GRF5. As mentioned above another approach to enhance the expression level of an endogenous gene like GRF5 is the application of so-called synthetical transcription activators. They are typically designed by the fusion of a recognition domain and at least one activator domain. The recognition domain can be derived from known systems like Zinc finger, TAL effectors or CRISPR; for activation, fusing for instances the herpes simplex virus derived VP-16 or VP-64 activation domains to a recognition domain can cause an increase in transcription. Weaker activation domains such as the AD of human NF-κB add to the variety of options for gene activation. Furthermore, as shown on endogenous promoters, combinations of activators can be used to introduce synergistic effects (Moore et al. (2014). "Transcription activator-like effectors: a toolkit for synthetic biology." *ACS synthetic biology,* 3(10), 708-716.; US 2002/0046419 A1; Lowder et al. (2017). "Multiplexed transcriptional activation or repression in plants using CRISPR-dCas9-based systems." *Plant Gene Regulatory Networks: Methods and Protocols,* 167-184.). The synthetical transcription activator can be delivered to the plant cell or introduced into the plant cell also as precursor, i.e. as DNA or RNA molecule encoding such artificial or synthetical transcription activator or a domain thereof or as inactive form of transcription activator which is activated later in the cell or a in a specific compartment of the cell. Finally, enhancing expression of GRF genes can be also achieved by the inactivation of upstream negative regulators (i.e. miR396) or by the creation of a mutant version of the GRF gene that is resistant to such negative regulators.

Preferably, the GRF5 polypeptide of the present invention comprises an amino acid sequence selected from the group consisting of SEQ ID NO: 2, 4, 6, 8, 10, 12, 14, 16, 18, 20, 22, 24, 26, 28, 30, 32, 106, 108, 110, 112 or 209, or an amino acid sequence having at least 70% identity to SEQ ID NO: 2, 4, 6, 8, 10, 12, 14, 16, 18, 20, 22, 24, 26, 28, 30, 32, 106, 108, 110, 112 or 209, preferably at least 80%, at least 85%, at least 90%, more preferably at least 95%, at least 98% or at least 99% identity to SEQ ID NO: 2, 4, 6, 8, 10, 12, 14, 16, 18, 20, 22, 24, 26, 28, 30, 32, 106, 108, 110, 112 or 209, and preferably comprises an indicator motif as described herein, particularly preferably an indicator motif consisting of any of the amino acid sequences SEQ ID NO: 41 to SEQ ID NO: 104 or SEQ ID NO: 113 to SEQ ID NO: 176. The GRF5 polypeptide, for example encoded by an endogenous gene, may comprise an amino acid sequence selected from the group consisting of the sequences of SEQ ID NO: 2 (*Arabidopsis thaliana*), SEQ ID NO: 4 (*Beta vulgaris*), SEQ ID NO: 6 (*Zea mays*), SEQ ID NO: 8 (*Triticum aestivum*), SEQ ID NO: 10 (*Brassica napus*), SEQ ID NO: 12 (*Brassica rapa*), SEQ ID NO: 14 (*Brassica oleracea*), SEQ ID NO: 16 (*Raphanus sativus*), SEQ ID NO: 18 (*Sorghum bicolor*), SEQ ID NO: 20 (*Helianthus annuus*), SEQ ID NO: 22 (*Solanum tuberosum*), SEQ ID NO: 24 (*Hordeum vulgare*), SEQ ID NO: 26 (Seca/e *cereale*), SEQ ID NO: 28 (*Glycine max*), SEQ ID NO: 30 (*Gossypium hirsutum*), SEQ ID NO: 32 (*Oryza sativa*), SEQ ID NO: 106 (*Glycine max*), SEQ ID NO: 108 (*Brassica napus*), SEQ ID NO: 110 (*Helianthus annuus*), SEQ ID NO: 112 (*Zea mays*) or SEQ ID NO: 209 (*Zea mays*).

An exogenous (heterologous) or endogenous polynucleotide encoding the GRF5 polypeptide of the invention comprises (i) a nucleotide sequence comprising SEQ ID NO: 1, 3, 5, 7, 9, 11, 13, 15, 17, 19, 21, 23, 25, 27, 29, 31, 105, 107, 109, 111, 207, 208 or 210;

(ii) a nucleotide sequence comprising a sequence being at least 70%, preferably at least 80%, at least 85%, at least 90%, more preferably at least 95%, at least 98% or at least 99% identical to a nucleotide sequence comprising SEQ ID NO: 1, 3, 5, 7, 9, 11, 13, 15, 17, 19, 21, 23, 25, 27, 29, 31, 105, 107, 109, 111, 207, 208 or 210;

(iii) a nucleotide sequence encoding a GRF5 polypeptide as defined above or a nucleotide sequence encoding a polypeptide encoded by (i) and/or (ii) within the scope of the degeneracy of the genetic code;

(iv) a nucleotide sequence complementary to a nucleotide sequence of (i), (ii) or (iii); or/and (v) a nucleotide sequence hybridizing with a nucleotide sequence of (iv) under stringent condition.

The polynucleotide encoding the GRF5 polypeptide, particularly the polynucleotide encoding the GRF5 polypeptide, may comprise a nucleotide sequence selected from the group consisting of the sequences of SEQ ID NO: 1 (*Arabidopsis thaliana*); SEQ ID NO: 3 (*Beta vulgaris*), SEQ ID NO: 5 (*Zea mays*), SEQ ID NO: 7 (*Triticum aestivum*), SEQ ID NO: 9 (*Brassica napus*), SEQ ID NO: 11 (*Brassica rapa*), SEQ ID NO: 13 (*Brassica* o/eracea), SEQ ID NO: 15 (*Raphanus sativus*), SEQ ID NO: 17 (*Sorghum bicolor*), SEQ ID NO: 19 (*Helianthus annuus*), SEQ ID NO: 21 (*Solanum tuberosum*), SEQ ID NO: 23 (*Hordeum vulgare*), SEQ ID NO: 25 (Seca/e *cereale*), SEQ ID NO: 27 (*Glycine max*), SEQ ID NO: 29 (*Gossypium hirsutum*), SEQ ID NO: 31 (*Oryza sativa*), SEQ ID NO: 105 (*Glycine max*), SEQ ID NO: 107 (*Brassica napus*), SEQ ID NO: 109 (*Helianthus annuus*), SEQ ID NO: 111 (*Zea mays*), SEQ ID NO: 207 (synthetic), SEQ ID NO: 208 (synthetic) or SEQ ID NO: 210 (synthetic).

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other, is regarded as a position with non-identical residues. The alignment of the two sequences is performed by the Needleman and Wunsch algorithm (Needleman and Wunsch 1970). The computer-assisted sequence alignment above, can be conveniently performed using standard software program such as program NEEDLE as implemented in the The European Molecular Biology Open Software Suite (EMBOSS), e.g. version 6.3.1.2 (*Trends in Genetics* 16 (6), 276 (2000)), with its default parameter, e.g. for proteins matrix= EBLOSUM62, gapopen=10.0 and gapextend=0.5.

The terms "stringent conditions" or "hybridization under stringent conditions" refer to conditions under which nucleotide sequences with sufficient complementarity to one another usually remain hybridized. These stringent conditions are known to the skilled person and described, for example, in Current Protocols in Molecular Biology, John Wiley & Sons, N.Y. (1989) 6.3.1-6.3.6. The skilled person knows how to determine the required hybridization conditions on the basis of, for example, Sambrook et al., Molecular Cloning, Cold Spring Harbour Laboratory, 1989. The term "hybridization conditions" in this respect refers not only to the actual conditions prevailing during actual agglomeration of the nucleic acids, but also to the conditions prevailing during the subsequent washing steps. Examples of stringent hybridization conditions are conditions under which primarily only those nucleic acid molecules that have at least at least 80%, preferably at least 85%, at least 90%, at least 95%, at least 98% or at least 99% sequence identity undergo hybridization. Stringent hybridization conditions are, for example: 4×SSC at 65° C. and subsequent multiple washes in 0.1×SSC at 65° C. for approximately 1 hour. The term "stringent hybridization conditions" as used herein may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization takes place under stringent conditions.

The expression "operably linked" means that said elements of the chimeric gene are linked to one another in such a way that their function is coordinated and allows expression of the coding sequence, i.e. they are functionally linked. By way of example, a promoter is functionally linked to another nucleotide sequence when it is capable of ensuring transcription and ultimately expression of said other nucleotide sequence. Two proteins encoding nucleotide sequences are functionally or operably linked to each other if they are connected in such a way that a fusion protein of first and second protein or polypeptide can be formed.

A gene is said to be expressed when it leads to the formation of an expression product. An expression product denotes an intermediate or end product arising from the transcription and optionally translation of the nucleic acid, DNA or RNA, coding for such product, e. g. the second nucleic acid described herein. During the transcription process, a DNA sequence under control of regulatory regions, particularly the promoter, is transcribed into an RNA molecule. An RNA molecule may either itself form an expression product or be an intermediate product when it is capable of being translated into a peptide or protein. A gene is said to encode an RNA molecule as expression product when the RNA as the end product of the expression of the gene is, e.g., capable of interacting with another nucleic acid or protein. Examples of RNA expression products include inhibitory RNA such as e.g. sense RNA (co-suppression), antisense RNA, ribozymes, miRNA or siRNA, mRNA, rRNA and tRNA. A gene is said to encode a protein as expression product when the end product of the expression of the gene is a protein or peptide.

A nucleic acid (molecule) or nucleotide (sequence) or polynucleotide, as used herein, refers to both DNA and RNA. DNA also includes cDNA and genomic DNA. A nucleic acid molecule can be single- or double-stranded, and can be synthesized chemically or produced by biological expression in vitro or even in vivo.

It will be clear that whenever nucleotide sequences of RNA molecules are defined by reference to nucleotide sequence of corresponding DNA molecules, the thymine (T) in the nucleotide sequence should be replaced by uracil (U). Whether reference is made to RNA or DNA molecules will be clear from the context of the application.

As used herein "comprising" or the like is to be interpreted as specifying the presence of the stated features, integers, steps or components as referred to, but does not preclude the presence or addition of one or more features, integers, steps or components, or groups thereof. Thus, e.g., a nucleic acid or protein comprising a sequence of nucleotides or amino acids, may comprise more nucleotides or amino acids than the actually cited ones, i.e., be embedded in a larger nucleic acid or protein. A chimeric gene comprising a DNA region which is functionally or structurally defined may comprise additional DNA regions etc.

By means of GRF5, a plant cell or other plant precursor tissues can be provided having an improved ability of regeneration. This is particularly helpful for genetically modified plant cells, in particular plant cells with an edited genome.

According to a preferred embodiment of the invention, step (a1) of introducing the at least one nucleotide sequence of interest and GRF5 or the step (a2) of introducing the at least one nucleotide sequence of interest and inducing an enhanced expression level of an endogenous gene encoding the GRF5 yields in transient transformation of the plant cell. In terms of the invention, "transient transformation" means that the inserted sequence is not (stably) integrated into the genome of the plant cell. In another embodiment, a stable transformation is effected, wherein the nucleotide sequence of interest in step (a1) and (a2) of the method for transforming disclosed here and/or the polynucleotide encoding an GRF5 polypeptide in step (a1) of the method of modifying the genome disclosed here is inserted into the genome of the plant cell. According to an especially preferred embodiment of the invention, the nucleotide sequence encoding GRF5 is transformed transiently into the cell while the nucleotide sequence of interest is stably transformed into the genome of the cell.

Modifying the genome of the plant cell can be accomplished by means of a double-stranded DNA break (DSB) inducing enzyme which preferably recognizes a predetermined site in the genome of said cell.

Thus, another embodiment of the present invention is a method for modifying the genome of a plant cell comprising the steps (a1) introducing into a plant cell an expression cassette comprising a polynucleotide encoding a GRF5 polypeptide, mRNA(s) encoding GRF5 polypeptide (including pre-mRNA(s)), or GRF5 polypeptide(s); or (a2) inducing in a plant cell an enhanced expression level of an endogenous gene encoding a GRF5 polypeptide; and (b) cultivating the plant cell of (a1) or (a2) or a plant cell derived from the plant cell of (a1) or (a2) under conditions where in the plant cell the GRF5 polypeptide is expressed from the expression cassette, GRF5 polypeptide is translated from introduced mRNA(s), GRF5 polypeptide is enhanced/increased expressed from the endogenous gene, or GRF5 polypeptide(s) are present, preferably in an enhanced amount compared to the amount in a wild type plant cell or a plant cell into which the expression cassette comprising a polynucleotide encoding a GRF5 polypeptide, mRNA(s) encoding GRF5 polypeptide or the GRF5 polypeptide has not been introduced according to step (a1) or in which the enhanced expression level of an endogenous gene encoding a GRF5 polypeptide has not been induced according to step (a2);

(c) modifying the genome of the plant cell of (b) by means of a double-stranded DNA break (DSB) inducing enzyme which preferably recognizes a predetermined site in the genome of said cell, and optionally by means of a repair nucleic acid molecule, wherein the modification of said genome at said predetermined site is selected from i. a replacement of at least one nucleotide;
ii. a deletion of at least one nucleotide;
iii. an insertion of at least one nucleotide; or
iv. any combination of i.-iii.; and wherein step (c) is conducted simultaneously with step (a1)/(a2) and/or (b), before step (a1)/(a2), between step (a1)/(a2) or (b) or after step (b).

As used herein, a "double-stranded DNA break inducing enzyme" or "DSBI enzyme" is an enzyme capable of inducing a double-stranded DNA break at a particular nucleotide sequence, called the "recognition site". The double-stranded DNA break (DSB)-inducing enzyme can, for example, be selected from the group consisting of meganuclease, TAL effector nuclease, zinc finger nuclease, CRISPR systems like CRISPR/Cas9, CRISPR/Cpf1, CRISPR/CasX, CRISPR/CasY, CRISPR/Csm1 or CRISPR/MAD7. Rare-cleaving endonucleases are DSBI enzymes that have a recognition site of preferably about 14 to 70 consecutive nucleotides, and therefore have a very low frequency of cleaving, even in larger genomes such as most plant genomes. Homing endonucleases, also called meganucleases, constitute a family of such rare-cleaving endonucleases. They may be encoded by introns, independent genes or intervening sequences, and present striking structural and functional properties that distinguish them from the more classical restriction enzymes, usually from bacterial restriction-modification Type II systems. Their recognition sites have a general asymmetry which contrast to the characteristic dyad symmetry of most restriction enzyme recognition sites. Several homing endonucleases encoded by introns or inteins have been shown to promote the homing of their respective genetic elements into allelic intronless or inteinless sites. By making a site-specific double strand break in the intronless or inteinless alleles, these nucleases create recombinogenic ends, which engage in a gene conversion process that duplicates the coding sequence and leads to the insertion of an intron or an intervening sequence at the DNA level. A list of other rare cleaving meganucleases and their respective recognition sites is provided in Table I of WO 03/004659 (pages 17 to 20) (incorporated herein by reference).

Furthermore, methods are available to design custom-tailored rare-cleaving endonucleases that recognize basically any target nucleotide sequence of choice. Briefly, chimeric restriction enzymes can be prepared using hybrids between a zinc-finger domain designed to recognize a specific nucleotide sequence and the non-specific DNA-cleavage domain from a natural restriction enzyme, such as FokI. Such methods have been described e.g. in WO 03/080809, WO 94/18313 or WO 95/09233 and in Isalan et al. (2001). A rapid, generally applicable method to engineer zinc fingers illustrated by targeting the HIV-1 promoter. *Nature biotechnology,* 19(7), 656; Liu et al. (1997). Design of polydactyl zinc-finger proteins for unique addressing within complex genomes. *Proceedings of the National Academy of Sciences,* 94(11), 5525-5530.).

Another example of custom-designed endonucleases includes the TALE nucleases (TALENs), which are based on transcription activator-like effectors (TALEs) from the bacterial genus *Xanthomonas* fused to the catalytic domain of a nuclease (e.g. FokI or a variant thereof). The DNA binding specificity of these TALEs is defined by repeat-variable di-residues (RVDs) of tandem-arranged 34/35-amino acid repeat units, such that one RVD specifically recognizes one nucleotide in the target DNA. The repeat units can be assembled to recognize basically any target sequences and fused to a catalytic domain of a nuclease create sequence specific endonucleases (see e.g. Boch et al. (2009). Breaking the code of DNA binding specificity of TAL-type III effectors. *Science,* 326(5959), 1509-1512; Moscou & Bogdanove (2009). A simple cipher governs DNA recognition by TAL effectors. *Science,* 326(5959), 1501-1501; and WO 2010/079430, WO 2011/072246, WO 2011/154393, WO 2011/146121, WO 2012/001527, WO 2012/093833, WO 2012/104729, WO 2012/138927, WO 2012/138939). WO 2012/138927 further describes monomeric (compact) TALENs and TALEs with various catalytic domains and combinations thereof.

Recently, a new type of customizable endonuclease system has been described; the so-called CRISPR/Cas system. A CRISPR system in its natural environment describes a molecular complex comprising at least one small and individual non-coding RNA in combination with a Cas nuclease or another CRISPR nuclease like a Cpf1 nuclease (Zetsche et al., "Cpf1 Is a Single RNA-Guides Endonuclease of a Class 2 CRISPR-Cas System", Cell, 163, pp. 1-13, October 2015) which can produce a specific DNA double-stranded break. Presently, CRISPR systems are categorized into 2 classes comprising five types of CRISPR systems, the type II system, for instance, using Cas9 as effector and the type V system using Cpf1 as effector molecule (Makarova et al., Nature Rev. Microbiol., 2015). In artificial CRISPR systems, a synthetic non-coding RNA and a CRISPR nuclease and/or optionally a modified CRISPR nuclease, modified to act as nickase or lacking any nuclease function, can be used in combination with at least one synthetic or artificial guide RNA or gRNA combining the function of a crRNA and/or a tracrRNA (Makarova et al., 2015, supra). The immune response mediated by CRISPR/Cas in natural systems requires CRISPR-RNA (crRNA), wherein the maturation of this guiding RNA, which controls the specific activation of the CRISPR nuclease, varies significantly between the various CRISPR systems which have been characterized so far. Firstly, the invading DNA, also known as a spacer, is integrated between two adjacent repeat regions at the proximal end of the CRISPR locus. Type II CRISPR systems code for a Cas9 nuclease as key enzyme for the interference step, which system contains both a crRNA and also a trans-activating RNA (tracrRNA) as the guide motif. These hybridize and form double-stranded (ds) RNA regions which are recognized by RNAseIII and can be cleaved in order to form mature crRNAs. These then in turn associate with the Cas molecule in order to direct the nuclease specifically to the target nucleic acid region. Recombinant gRNA molecules can comprise both the variable DNA recognition region and also the Cas interaction region and thus can be specifically designed, independently of the specific target nucleic acid and the desired Cas nuclease. As a further safety mechanism, PAMs (protospacer adjacent motifs) must be present in the target nucleic acid region; these are DNA sequences which follow on directly from the Cas9/RNA complex-recognized DNA. The PAM sequence for the Cas9 from *Streptococcus pyogenes* has been described to be "NGG" or "NAG" (Standard IUPAC nucleotide code) (Jinek et al, "A programmable dual-RNA-guided DNA endonuclease in adaptive bacterial immunity", Science 2012, 337: 816-821). The PAM sequence for Cas9 from *Staphylococcus aureus* is "NNGRRT" or "NNGRR(N)". Further variant CRISPR/Cas9 systems are known. Thus, a *Neisseria meningitidis* Cas9 cleaves at the PAM sequence NNNNGATT. A *Streptococcus thermophilus* Cas9 cleaves at the PAM sequence NNAGAAW. Recently, a further PAM motif NNNNRYAC has been described for a CRISPR system of *Campylobacter* (WO 2016/021973 A1). For Cpf1 nucleases it has been described that the Cpf1-crRNA complex, without a tracrRNA, efficiently recognize and cleave target DNA proceeded by a short T-rich PAM in contrast to the commonly G-rich PAMs recognized by Cas9 systems (Zetsche et al., supra). Furthermore, by using modified CRISPR polypeptides, specific single-stranded breaks can be obtained. The combined use of Cas nickases with various recombinant gRNAs can also induce highly specific DNA double-stranded breaks by means of double DNA nicking. By using two gRNAs, moreover, the specificity of the DNA binding and thus the DNA cleavage can be optimized. Further CRISPR effectors like CasX and CasY effectors originally described for bacteria, are meanwhile available and represent further effectors, which can be used for genome engineering purposes (Burstein et al., "New CRISPR-Cas systems from uncultivated microbes", Nature, 2017, 542, 237-241).

The cleavage site of a DSBI enzyme relates to the exact location on the DNA where the double-stranded DNA break is induced. The cleavage site may or may not be comprised in (overlap with) the recognition site of the DSBI enzyme and hence it is said that the cleavage site of a DSBI enzyme is located at or near its recognition site. The recognition site of a DSBI enzyme, also sometimes referred to as binding site, is the nucleotide sequence that is (specifically) recognized by the DSBI enzyme and determines its binding specificity. For example, a TALEN or ZNF monomer has a recognition site that is determined by their RVD repeats or ZF repeats respectively, whereas its cleavage site is determined by its nuclease domain (e.g. FokI) and is usually located outside the recognition site. In case of dimeric TALENs or ZFNs, the cleavage site is located between the two recognition/binding sites of the respective monomers, this intervening DNA region where cleavage occurs being referred to as the spacer region.

A person skilled in the art would be able to either choose a DSBI enzyme recognizing a certain recognition site and inducing a DSB at a cleavage site at or in the vicinity of the preselected/predetermined site or engineer such a DSBI enzyme. Alternatively, a DSBI enzyme recognition site may be introduced into the target genome using any conventional transformation method or by crossing with an organism having a DSBI enzyme recognition site in its genome, and any desired DNA may afterwards be introduced at or in the vicinity of the cleavage site of that DSBI enzyme.

In a particularly preferred aspect of this embodiment, a repair nucleic acid molecule is additionally introduced into the plant cell. As used herein, a "repair nucleic acid molecule" is a single-stranded or double-stranded DNA molecule or RNA molecule that is used as a template for modification of the genomic DNA at the preselected site in the vicinity of or at the cleavage site. As used herein, "use as a template for modification of the genomic DNA", means that the repair nucleic acid molecule is copied or integrated at the preselected site by homologous recombination between the flanking region(s) and the corresponding homology region(s) in the target genome flanking the preselected site, optionally in combination with non-homologous end-joining (NHEJ) at one of the two end of the repair nucleic acid molecule (e.g. in case there is only one flanking region). Integration by homologous recombination will allow precise joining of the repair nucleic acid molecule to the target genome up to the nucleotide level, while NHEJ may result in small insertions/deletions at the junction between the repair nucleic acid molecule and genomic DNA.

As used herein, "a modification of the genome", means that the genome has changed by at least one nucleotide. This can occur by replacement of at least one nucleotide and/or a deletion of at least one nucleotide and/or an insertion of at least one nucleotide, as long as it results in a total change of at least one nucleotide compared to the nucleotide sequence of the preselected genomic target site before modification, thereby allowing the identification of the modification, e.g. by techniques such as sequencing or PCR analysis and the like, of which the skilled person will be well aware.

As used herein "a preselected site", "a predetermined site" or "predefined site" indicates a particular nucleotide sequence in the genome (e.g. the nuclear genome or the chloroplast genome) at which location it is desired to insert, replace and/or delete one or more nucleotides. This can e.g. be an endogenous locus or a particular nucleotide sequence in or linked to a previously introduced foreign DNA or transgene. The preselected site can be a particular nucleotide position at (after) which it is intended to make an insertion of one or more nucleotides. The preselected site can also comprise a sequence of one or more nucleotides which are to be exchanged (replaced) or deleted.

As used in the context of the present application, the term "about" means+/−10% of the recited value, preferably +/−5% of the recited value. For example, about 100 nucleotides (nt) shall be understood as a value between 90 and 110 nt, preferably between 95 and 105.

As used herein, a "flanking region", is a region of the repair nucleic acid molecule having a nucleotide sequence which is homologous to the nucleotide sequence of the DNA region flanking (i.e. upstream or downstream) of the preselected site. It will be clear that the length and percentage sequence identity of the flanking regions should be chosen such as to enable homologous recombination between said flanking regions and their corresponding DNA region upstream or downstream of the preselected site. The DNA region or regions flanking the preselected site having homology to the flanking DNA region or regions of the repair nucleic acid molecule are also referred to as the homology region or regions in the genomic DNA.

To have sufficient homology for recombination, the flanking DNA regions of the repair nucleic acid molecule may vary in length, and should be at least about 10 nt, about 15 nt, about 20 nt, about 25 nt, about 30 nt, about 40 nt or about 50 nt in length. However, the flanking region may be as long as is practically possible (e.g. up to about 100-150 kb such as complete bacterial artificial chromosomes (BACs). Preferably, the flanking region will be about 50 nt to about 2000 nt, e.g. about 100 nt, 200 nt, 500 nt or 1000 nt. Moreover, the regions flanking the DNA of interest need not be identical to the homology regions (the DNA regions flanking the preselected site) and may have between about 80% to about 100% sequence identity, preferably about 95% to about 100% sequence identity with the DNA regions flanking the preselected site. The longer the flanking region, the less stringent the requirement for homology. Furthermore, to achieve exchange of the target DNA sequence at the preselected site without changing the DNA sequence of the adjacent DNA sequences, the flanking DNA sequences should preferably be identical to the upstream and downstream DNA regions flanking the preselected site.

As used herein, "upstream" indicates a location on a nucleic acid molecule which is nearer to the 5' end of said nucleic acid molecule. Likewise, the term "downstream" refers to a location on a nucleic acid molecule which is nearer to the 3' end of said nucleic acid molecule. For avoidance of doubt, nucleic acid molecules and their sequences are typically represented in their 5' to 3' direction (left to right).

In order to target sequence modification at the preselected site, the flanking regions must be chosen so that 3' end of the upstream flanking region and/or the 5' end of the downstream flanking region align(s) with the ends of the predefined site. As such, the 3' end of the upstream flanking region determines the 5' end of the predefined site, while the 5' end of the downstream flanking region determines the 3' end of the predefined site.

As used herein, said preselected site being located outside or away from said cleavage (and/or recognition) site, means that the site at which it is intended to make the genomic modification (the preselected site) does not comprise the cleavage site and/or recognition site of the DSBI enzyme, i.e. the preselected site does not overlap with the cleavage (and/or recognition) site. Outside/away from in this respect thus means upstream or downstream of the cleavage (and/or recognition) site.

The modified plant cell that has been transformed or gene edited according to the methods of the present invention and possibly has a modified genome can be regenerated into a whole (fertile) plant. Due to the presence of the additional GRF5 in the plant cell their ability to regenerate is significantly improved. Thus, in a preferred aspect of the invention, the transformation of a plant cell or the modification of a genome of a plant cell, respectively, is followed by a step of regenerating a plant. Accordingly, the present invention provides a method for producing a transgenic plant comprising (a) transforming a plant cell as described hereinabove and
(b) regenerating from the plant cell of (a) or from a plant cell derived from the plant cell of (a) a plant comprising at least one plant cell which comprises the at least one nucleotide sequence of interest as a transgene.

Further, the present invention also provides a method of producing a genetically modified plant comprising (a) modifying the genome of a plant cell as described hereinabove and
(b) regenerating from the plant cell of (a) or from a plant cell derived from the plant cell of (a) a plant comprising in at least one cell the modification of the genome or the modified plant cell.

Regeneration techniques rely on manipulation of certain phytohormones in a tissue culture growth medium, occasionally relying on a biocide and/or herbicide marker that can been introduced together with the desired nucleotide sequence(s) of interest. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, protoplasts, immature or mature embryos, embryonic tissue, meristematic tissues, organs, or parts thereof. Such regeneration techniques are described generally in Klee (1987) Ann. Rev. of Plant Phys. 38:467486. To obtain whole plants from transgenic tissues such as immature embryos, they can be grown under controlled environmental conditions in a series of media containing nutrients and hormones, a process known as tissue culture. Once whole plants are generated and produce seed, evaluation of the progeny begins.

According to the present invention, it is not only possible to improve the regeneration ability of transformed or genetically modified plant cells, but also other types of sensitive cells with poor regeneration abilities. In particular, the production of a haploid plant embryo from precursors like an immature male gametophyte or a microspore can be improved by means of GRF5.

Thus, another aspect of the present invention is a method of producing a haploid plant embryo comprising the steps (a1) introducing into an immature male gametophyte or a microspore an expression cassette comprising a polynucleotide encoding a GRF5 polypeptide, mRNA(s) encoding GRF5 polypeptide, or GRF5 polypeptide(s); or
(a2) inducing in an immature male gametophyte or a microspore an enhanced expression level of an endogenous gene encoding a GRF5 polypeptide; and
(b) cultivating the immature male gametophyte or the microspore of (a) under conditions where in the immature male gametophyte or the microspore the GRF5 polypeptide is expressed from the expression cassette, GRF5 polypeptide is translated from introduced mRNA(s), GRF5 polypeptide is enhanced expressed from the endogenous gene, or GRF5 polypeptide(s) are present, preferably in an enhanced amount compared to the amount in a wild type plant cell or a plant cell into which the expression cassette comprising a polynucleotide encoding a GRF5 polypeptide, mRNA(s) encoding GRF5 polypeptide or the GRF5 polypeptide has not been introduced according to step (a1) or in which the enhanced expression level of an endogenous gene encoding a GRF5 polypeptide has not been induced according to step (a2); and
(c) selecting a haploid plant embryo derived from the immature male gametophyte or the microspore of step (b).

The invention also includes a method of producing haploid seedlings comprising exposing haploid plant material to an expression cassette comprising a polynucleotide encoding a GRF5 polypeptide, mRNA encoding GRF5 polypeptide, or GRF5 polypeptide(s) to produce haploid embryos and then converting (i.e. germinating) the haploid embryos into seedlings. The invention therefore includes a method of making haploid plants comprising growing a seedling produced in accordance with the aforementioned method. The invention also provides a method of producing a double haploid plant comprising culturing haploid plant material in the presence of GRF5 for a period, stimulating or allowing a spontaneous chromosome doubling, and growing the double haploid plant material into a seedling, plantlet or plant. In certain embodiments, haploid embryogenesis and chromosome doubling may take place substantially simultaneously. In other embodiments, there may be a time delay between haploid embryogenesis and chromosome doubling. Should growth of haploid seedlings, plants or plantlets not involve a spontaneous chromosome doubling event, then a chemical chromosome doubling agent may be used, e.g. colchicine. Many procedures involve contact of plant cells with colchicine, anti-microtubule agents or anti-microtubule herbicides such as pronamide, nitrous oxide, or any mitotic inhibitor. The result is homozygous doubled haploid cells. Where colchicine is used, the concentration in the medium may be generally 0.01%-0.2%. The range of colchicine concentration may be from about 400-600 mg/L.

Where a microspore is exposed to GRF5 polypeptide(s), then a callus may form and this may undergo organogenesis to form an embryo. The invention therefore includes a method of producing haploid plant callus comprising exposing an immature male gametophyte or a microspore to GRF5 polypeptide(s) or introducing into it an expression cassette comprising a polynucleotide encoding a GRF5 polypeptide, mRNA encoding GRF5 polypeptide, or GRF5 polypeptide(s).

The exposure of the immature male gametophyte or the microspore to GRF5 during cultivation step is preferably carried out for a period of time sufficient to induce haploid embryo formation. The period of time needed may depend on the species of plant concerned and these are all readily ascertainable by a person of ordinary skilled in the art. A preferred range of GRF5 exposure is from about 1 to about 20 hours; more preferably from about 2 to about 20 hours.

In certain aspects of the invention, a physical stress is applied to the haploid plant material prior to the introduction of the expression cassette comprising a polynucleotide encoding a GRF5 polypeptide, mRNA encoding GRF5 polypeptide, or GRF5 polypeptide(s). The physical stress may be any of temperature, darkness, light or ionizing radiation, starvation or osmotic stress, for example. The light may be full spectrum sunlight, or one or more frequencies selected from the visible, infrared or UV spectrum. The stresses may be continuous or interrupted (periodic); regular or random over time.

The present invention is applicable to any plant species, whether monocot or dicot. Preferably, plants which may be subject to the methods and uses of the present invention are plants of the genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium*, or *Helianthus*. More preferably, the plant is selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale*, Triticale, *Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Omarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Helianthus annuus, Helianthus tuberosus* and/or *Allium tuberosum*. Particularly preferred are *Beta vulgaris, Zea mays, Triticum aestivum, Hordeum vulgare, Secale cereale, Helianthus annuus, Solanum tuberosum, Sorghum bicolor, Brassica rapa, Brassica napus, Brassica juncacea, Brassica oleracea, Raphanus sativus, Oryza sativa, Glycine max*, and/or *Gossypium* sp.

Suitable plant cells according the present invention are especially cells of a callus tissue, preferably of a friable callus, of a meristematic tissue, of a reproductive tissue (e.g. microspores) or an embryonic tissue as well as protoplasts.

A part or parts of plants may be attached to or separated from a whole intact plant. Such parts of a plant include, but are not limited to, organs, tissues, and cells of a plant, and preferably seeds.

Subject matter of the present invention also are the plants that are obtained or obtainable by the methods described above. Accordingly, one embodiment of the invention is a transgenic plant obtained or obtainable by the above method of transforming a plant cell and regenerating a plant from said cell, as well as progeny or parts thereof, wherein the progeny or the part comprises the at least one nucleotide sequence of interest as transgene. Another embodiment of the invention is a genetically modified plant obtained or obtainable by the above method of modifying the genome of a plant cell and regenerating a plant from said cell as well as progeny or parts thereof, wherein the progeny or the part comprises the modification in the genome introduced by the above method of modification.

Further subject matter of the present invention is a plant cell or a seed derived from the above transgenic plant or genetically modified plant. Such a plant cell preferably comprises a polynucleotide encoding a GRF5 polypeptide transiently or stably integrated and a double-stranded DNA break (DSB)-inducing enzyme, which preferably recognizes a predetermined site in the genome of said cell and optionally a repair nucleic acid molecule. The polynucleotide encoding the GRF5 polypeptide is preferably operably linked to a suitable regulatory sequence so that the plant cell is capable of expressing the GRF5 polypeptide. A regulatory sequence means, for example, a "promoter" which refers to a nucleotide sequence, usually upstream (5') to its coding sequence, which controls the expression of the coding sequence by providing the recognition for RNA polymerase and other factors required for proper transcription. "Constitutive promoter" refers to promoters that direct gene expression in nearly all tissues and at all times. Examples of constitutive promoters include CaMV 35S promoter, double CaMV 35S promoter (70S promoter), nopaline synthase (nos) promoter, BdEF1 promoter, or ubiquitin promoter like PcUbi4 or ZmUbi1. "Regulated promoter" refers to promoters that direct gene expression not constitutively but in a temporally and/or spatially regulated manner and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered and are well-known to a person skilled in the art. "Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated (such as in early or late embryogenesis), during fruit ripening in developing seeds or fruit, in fully differentiated leaf, or at the onset of senescence. "Inducible promoter" refers to those regulated promoters that can be turned on in one or more cell types by an external stimulus (such as a chemical, light, hormone, stress, or pathogen). Examples for inducible promoter are promoters inducible by ecdysone, dexamethasone, ethanol. Such promoters are well-known from the state of the art (e.g., Samalova et al. (2005). pOp6/LhGR: a stringently regulated and highly responsive dexamethasone-inducible gene expression system for tobacco. *The Plant Journal,* 41(6), 919-935; Gatz & Lenk (1998). Promoters that respond to chemical inducers. *Trends in Plant Science,* 3(9), 352-358.).

A further subject matter of the invention is a haploid plant embryo obtained or obtainable by the method of the invention.

Another subject-matter of the present invention is a plant cell comprising a polynucleotide encoding a GRF5 polypeptide transiently or stable integrated, and a double stranded DNA break (DSB) inducing enzyme which preferably recognize a predetermined site in the genome of said cell, and optionally a repair nucleic acid molecule, wherein preferably the polynucleotide encoding the GRF5 polypeptide being operatively linked to a suitable regulatory sequence, so that the plant cell is capable of expressing the GRF5 polypeptide. Such plant cell can be obtained when conducting the above described method for modifying the genome of a plant cell.

A further aspect of the present invention is the use of a polynucleotide encoding a GRF5 polypeptide, mRNA encoding a GRF5 polypeptide, GRF5 polypeptide or an activator of expression of an endogenous gene encoding a GRF5 polypeptide in a method of transformation of a plant cell, preferably in the method of transformation as described above, in a method of modifying the genome of a plant cell, preferably in the method of modifying the genome as described above, in a method for the production of a plant or a haploid plant embryo, preferably in the method for the production of a plant or a haploid plant embryo as described above, or in a method for regeneration of a plant, preferably in the method for regeneration of a plant as described above.

Unless stated otherwise in the Examples, all recombinant DNA techniques are carried out according to standard protocols as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Cray, jointly published by BIOS Scientific Publications Ltd (UK) and Blackwell Scientific Publications, UK. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

All patents, patent applications, and publications or public disclosures (including publications on internet) referred to or cited herein are incorporated by reference in their entirety.

The invention will be further described with reference to the following Figures and Examples described herein. However, it is to be understood that the invention is not limited to such Examples.

FIGURES

FIG. 1: Total number of developing shoots in each selection step (S1-S4). Data obtained from 5 independent transformation experiments performed either with the control construct pZFN-tdT-nptII or with pZFN-nptII-GRF5 (compare table 3).

FIG. 2: Shoot regeneration at the beginning of the selection step 3 (S3) of 14 independently transformed calli on a control experiment (A) and an experiment done with pZFN-nptII-GRF5 (B). Arrows indicate developing shoots. Experiments were performed following the method of 2.1.

FIG. 3: Shoot regeneration in sugar beet calli 10 days after bombarded with pZFN-nptII-GRF5 (A) and the control plasmid pABM70S-TurboYFP (B). The calli were co-bombarded with pUbi4-tDT plasmid to control the transient expression levels by red fluorescence. Experiments were performed following the method 2.2. Three independently bombarded calli are shown.

FIG. 4: Expression level of GRF5 in eleven independent sugar beet transgenic events.

FIG. 5: A: Sequence comparison of the sequences of GRF5 polypeptides derived from 16 different plant species and deduction of a GRF5 specific indicator motif (SEQ ID NO: 177); partial sequences of the sequences of GRF5 polypeptides as shown are set forth in SEQ ID NOs: 178-206; B: motif analysis by sequence alignment/comparison on the complete protein sequences derived from 16 different plant species with allowing up to 10 mismatches. The columns "start" and "stop" indicate the starting and ending position of sequence fragment of the GRF5 polypeptides corresponding to the indicator motif; column "mismatches" shows the number of mismatches between the respective GRF5 polypeptide and the indicator motif; partial sequences of the sequences of GRF5 polypeptides as shown are set forth in SEQ ID NOs: 178-184 and SEQ ID NOs: 186-206. AtGRF1_AT2G22840.1 (SEQ ID NO: 33); AtGRF2_AT4G37740.1 (SEQ ID NO: 34); AtGRF3_AT2G36400.1 (SEQ ID NO: 35); AtGRF4_AT3G52910.1 (SEQ ID NO: 36); AtGRF6_AT2G06200.1 (SEQ ID NO: 37); AtGRF7_AT5G53660.1 (SEQ ID NO: 38); AtGRF8_AT4G24150.1 (SEQ ID NO: 39); AtGRF9_AT2G45480.1 (SEQ ID NO: 40).

Figure 6:
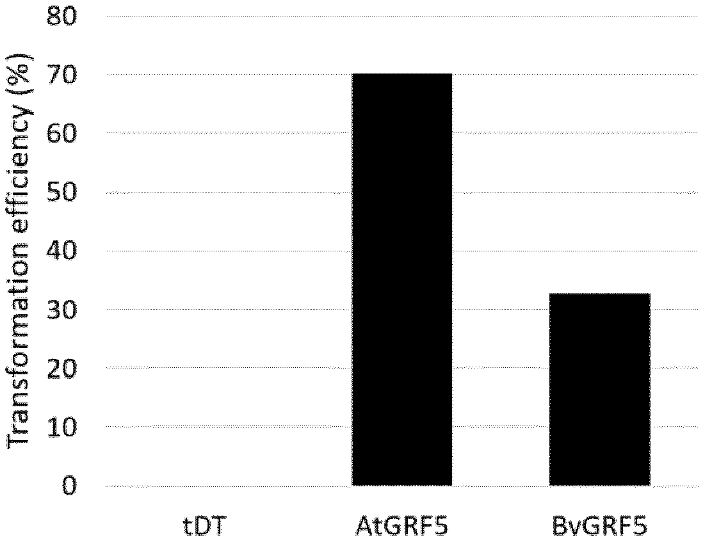

FIG. 6: Transformation frequency in sugar beet obtained with the control construct 70S::tdT, a constructs to overexpress AtGRF5 (cDNA—SEQ ID NO: 1; amino acid sequence—SEQ ID NO: 2), and the sugar beet GRF5 ortholog, BvGRF5 (synthetic DNA—SEQ ID NO: 207; amino acid sequence—SEQ ID NO: 4).

Figure 7:
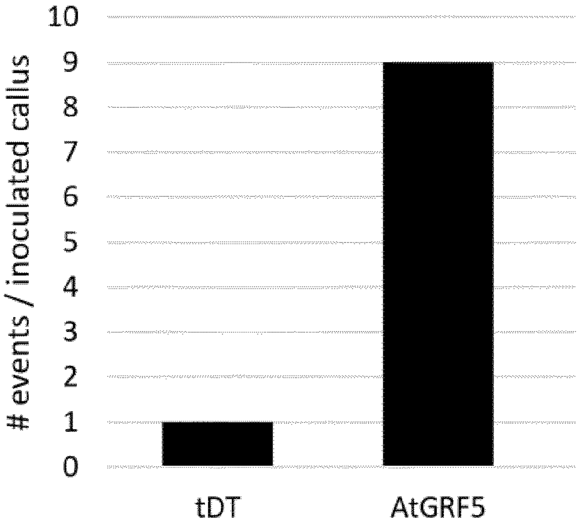

FIG. 7: Number of transgenic shoots per inoculated sugar beet callus obtained in transformation experiments by using constructs to overexpress either tdTomato (tDT) (control) and AtGRF5 (cDNA—SEQ ID NO: 1; amino acid sequence—SEQ ID NO: 2).

Figure 8:
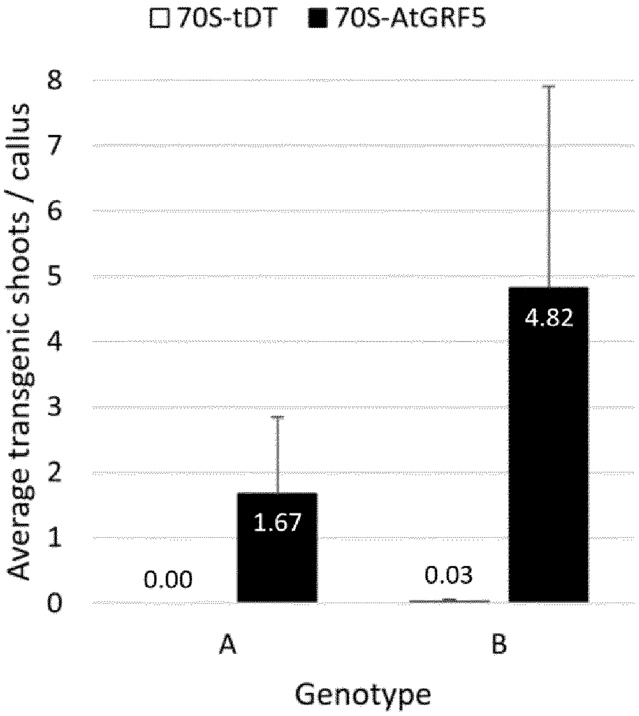

FIG. 8: Average number of transgenic shoots per sugar beet callus obtained from transformation experiments either with the control construct 70S-tDT (control) and the construct to overexpress AtGRF5 (70S-GRF5). Two recalcitrant genotypes A and B were used. The recalcitrance level to regenerate shoots of the genotype A is very high, whereas the genotype B displays a milder recalcitrance that A.

FIG. 9: Callus regeneration experiments of transgenic lines overexpressing AtGRF5 in sugar beet. The callus formation frequency (A) and the shoot regeneration frequency (B) were scored by using the callus induction medium and the shoot regeneration medium described in Kischenko et al., 2005 (see also example 1). A total of 5 independent events overexpressing AtGRF5 were assayed (AtGRF5-36, AtGRF5-41, AtGRF5-14, AtGRF5-94, AtGRF5-50). As control, non-transgenic sugar beet shoots (WT1 and WT2) and transgenic shoots overexpressing the tDT reporter protein (tDT-event) were used. Expression level of AtGRF5 was determined by qRT-PCR on samples isolated from the GRF5 transgenic events used in the assay (C).

Figure 10:
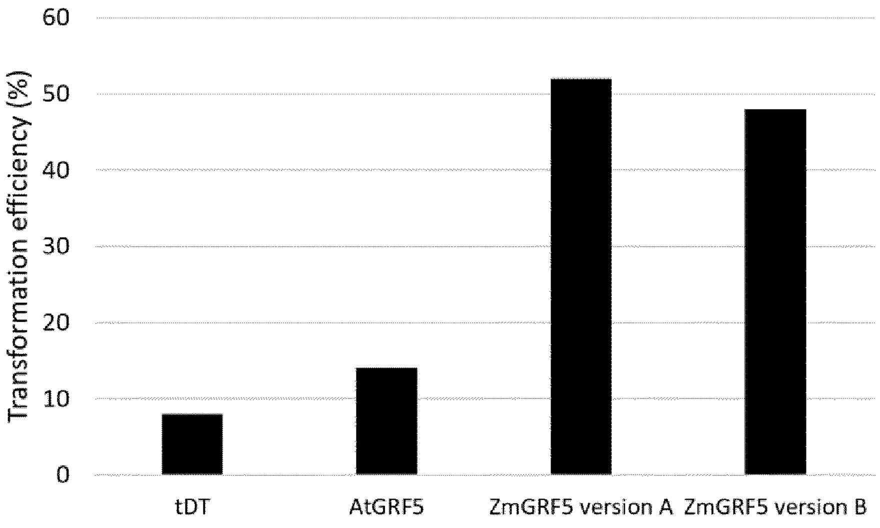

FIG. 10: Transformation frequency in Corn, either with the control construct 70S::tDT, or with constructs to overexpress AtGRF5 (cDNA—SEQ ID NO: 1; amino acid sequence—SEQ ID NO: 2), two GRF5 Corn orthologs [ZmGRF5 version A (synthetic DNA—SEQ ID NO: 208; amino acid sequence—SEQ ID NO: 209) and ZmGRF5 version B (synthetic DNA—SEQ ID NO: 210; amino acid sequence—SEQ ID NO: 112). Transformation efficiency was calculated as the number of transgenic events divided by the number of inoculated immature embryos.

Figure 11:
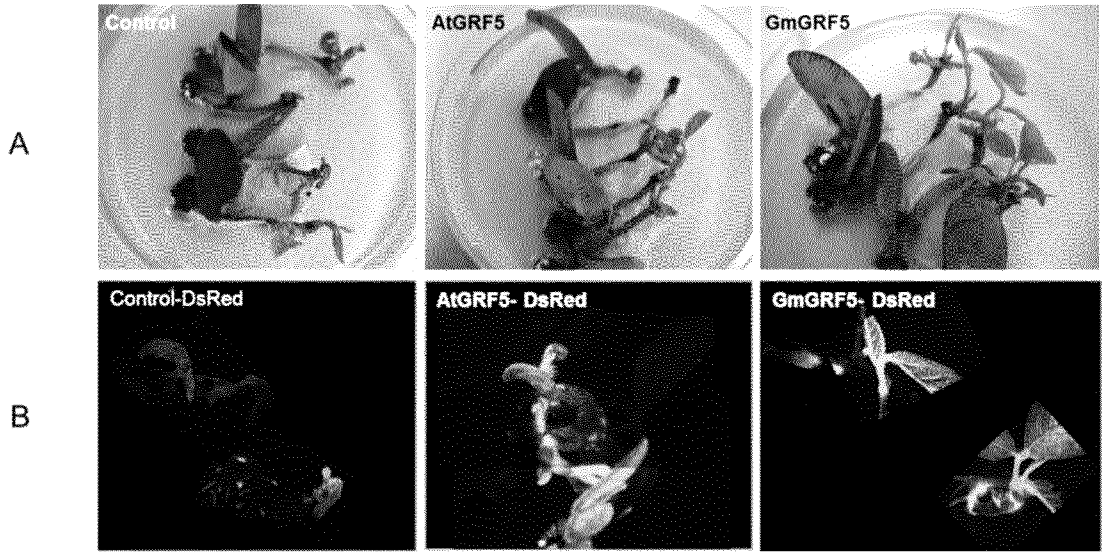

FIG. 11: Shoot development and DsRed fluorescence of shoots on soybean explants 21 days after transformation. Representative pictures of explants from DsRed control, AtGRF5, and GmGRF5 showing (A) shoot development at the primary-node and (B) DsRed fluorescence of shoots. DsRed pictures are a composite of multiple pictures and positioned in approximate position for orientation purposes.

Figure 12:
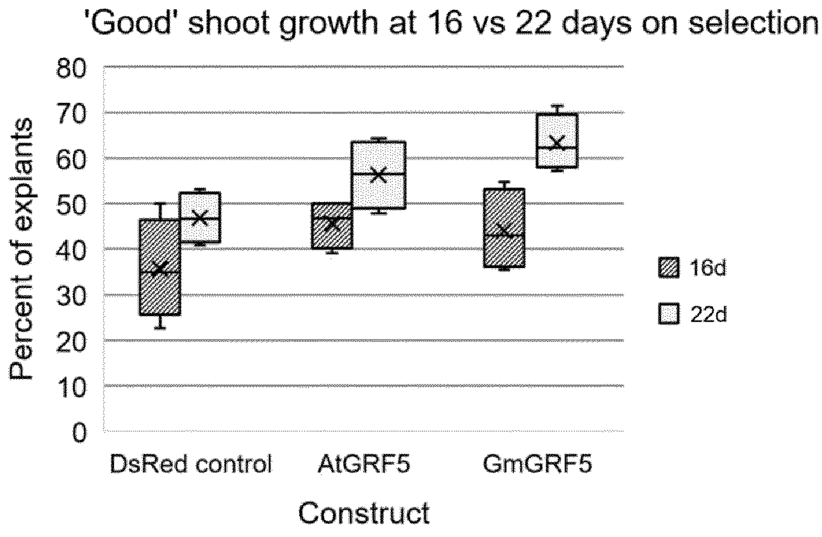

FIG. 12: Formation of 'good' shoot growth continued to rapidly increase from 16 to 22 days on selection. The percent of explants were scored at two timepoints to highlight the rapid production of shoots on selection for explants transformed with the three constructs.

Figure 13:
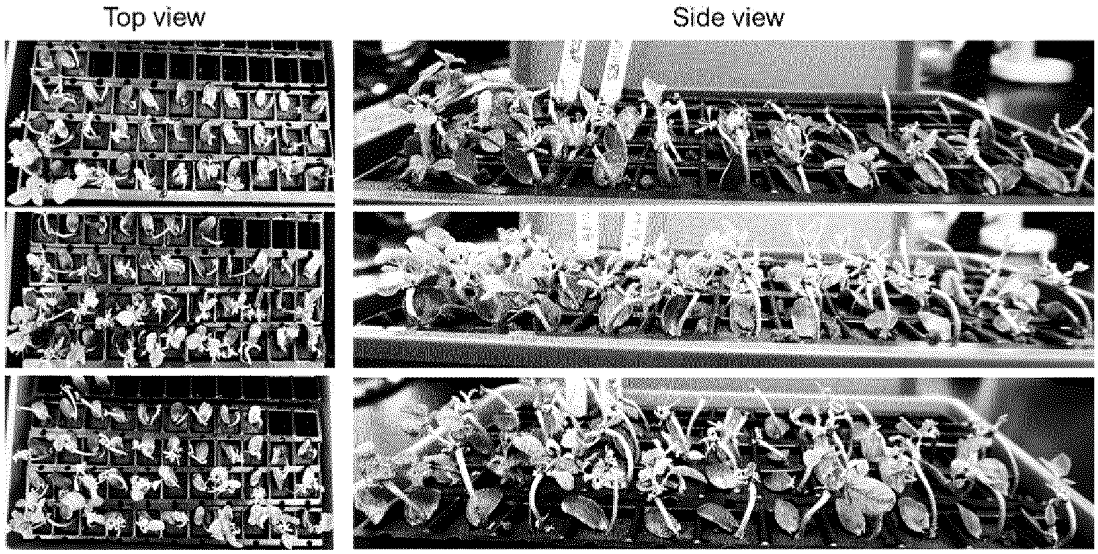

FIG. 13: Shoot formation on soybean explants transformed with and without GRF5 variants. Pictures taken from top and side view from one repetition is shown for the three treatments (constructs). Shoot growth is more pronounced in the explants transformed with AtGRF5 (middle panel) and GmGRF5 (below panel) vs. the DsRed control (upper panel).

Figure 14:
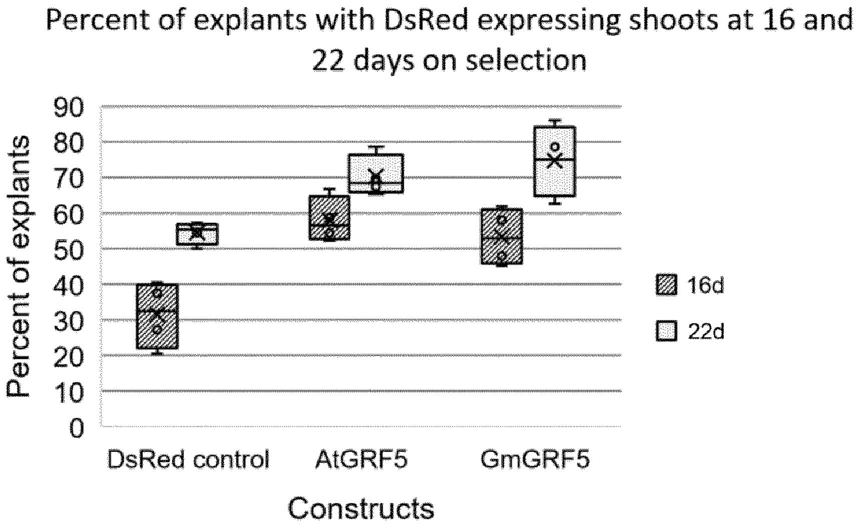

FIG. 14: A box-and-whisker plot visualizing the significant increase in regeneration of transgenic shoots in explants transformed with either AtGRF5 or GmGRF5 at 16 and 22 days on selection.

Figure 15:
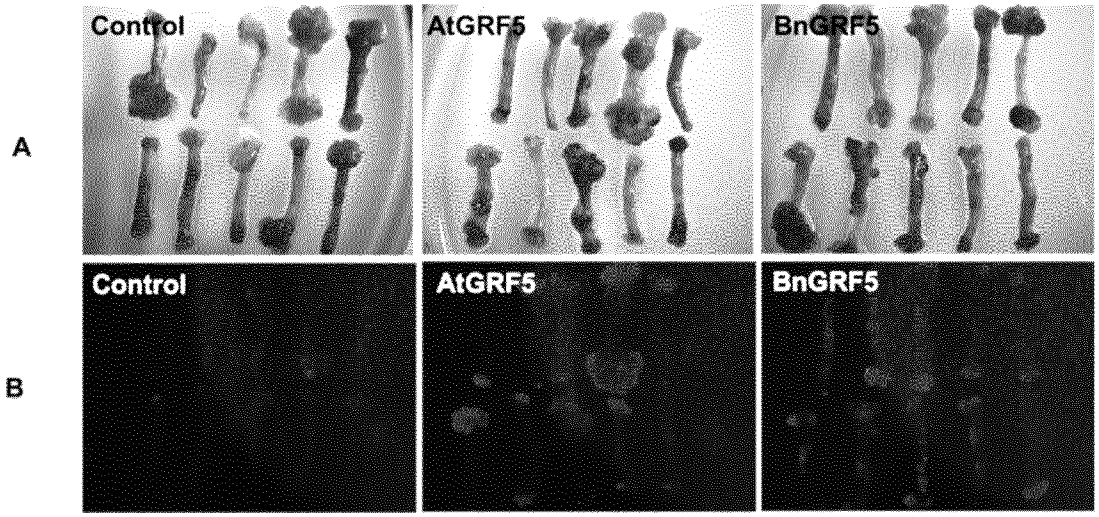

FIG. 15: Shoot development and DsRed fluorescence of shoots on canola explants 21 days after transformation. Representative pictures of explants from DsRed control, AtGRF5, and BnGRF5 showing (A) callus development at the hypocotyl segments and (B) DsRed fluorescence on explants.

Figure 16:
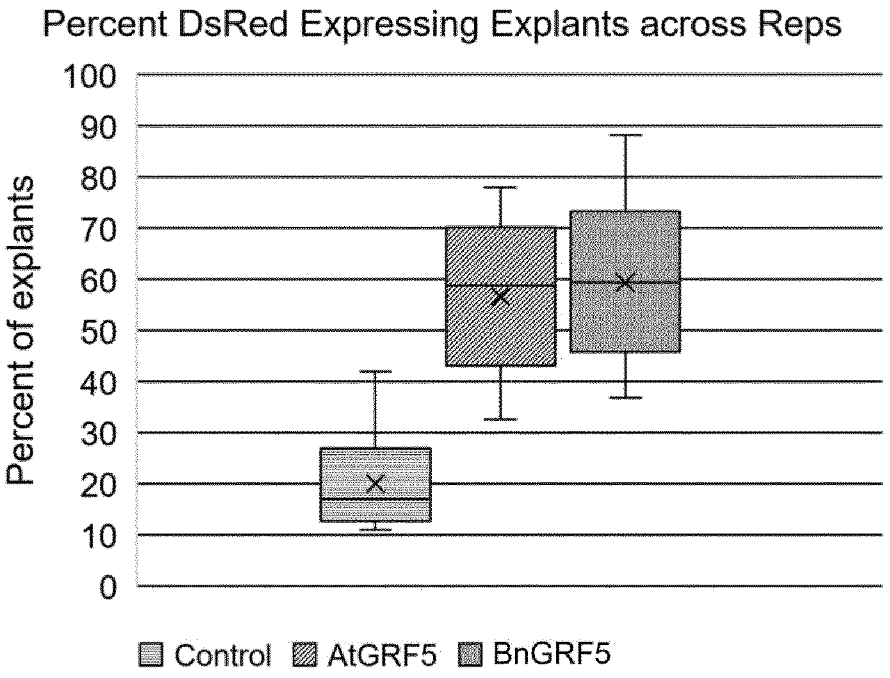

FIG. 16: The percent of DsRed expressing explants across five *Brassica napus* experiments transformed with AtGRF5, BnGRF5, and DsRed control are depicted in a box-and-whisker plot. The percent of explants expressing DsRed are significantly greater in AtGRF5 and BnGRF5 compared to control constructs, with nearly a 3-fold increase in the mean.

Figure 17:
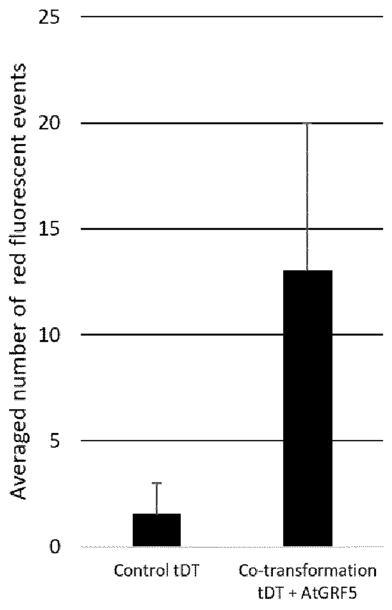

FIG. 17: Co-transformation of sugar beet callus with the control construct 70S-tDT and the 70S-AtGRF5. The inoculation of callus in the co-transformation experiments was done with a mixture 1:1 of the *Agrobacterium* strains harboring each construct individually.

EXAMPLES

1. *Beta vulgaris* Experiments

Production of the Binary Plasmid:

The binary vector pZFN-nptII-GRF5 was produced by following standard cloning procedures. Within the T-DNA of this vector, the cDNA encoding GRF5 (At3g13960) was cloned between the double CaMV 35S promoter and the nopaline synthase (NOS) terminator to ensure high ectopic expression levels of the GRF5 protein. The T-DNA also contains the neomycin phosphotransferase II (nptII) gene that confers resistance to a range of aminoglycoside antibiotics such as kanamycin or paromomycin and was used for the selection of transgenic plant cells and tissues. The NOS promoter and the pAG7 terminator flank the nptII gene. The backbone of the binary vector contains the colE1 and the pVS1 origins for plasmid replication in *Escherichia coli* and *Agrobacterium tumefaciens*, respectively; and the aadA gene that confers streptomycin/spectinomycin resistance for bacteria selection. The pZFN-nptII-GRF5 plasmid was transformed into AGL-1 *Agrobacterium* strain by a standard procedure.

Transformation of Micropropagated Shoots:

Shoots of sugar beets were transformed by different methods:

a) *Agrobacterium* mediated transformation based on Kischenko et al., 2005 Cell Biology International:

1. Micropropagated shoots of the genotype S706 were used as starting material. Shoots were multiplied in MS salts supplemented with 30 g/l sucrose and 0.25 mg/l benzyladenine (BAP).
2. To induce friable callus, leaf explants were incubated in MS salts including 15 g/l sucrose and 2 mg/l BAP at around 30° C. for several weeks.
3. Friable calli were harvested.
4. *Agrobacterium* AGL-1 harbouring the vector pZFN-nptII-GRF5 was grown in suitable medium supplemented with the appropriate antibiotics.
5. Calli were inoculated with *Agrobacterium* suspension. The co-culture of the callus tissue and the *Agrobacterium* was done in medium containing 440 mg/l $CaCl_2 \times 2H_2O$, 170 mg/l $KH_2PO_4$, 1900 mg/l $KNO_3$, 370 mg/l $MgSO_4$, 1650 mg/l $NH_4NO_3$, 2 mg/l BAP, 40 μg/l Acetosyringone, 20 g/l sucrose and 2 g/l glucose for at least 2 days.
6. Calli were subcultured to MS salts supplemented with 30 g/l sucrose, 1 mg/l GA3, 1 mg/l TDZ and 500 mg/l Timentin and incubated in the dark, for c. 1 week.
7. For the selection of transgenic cells, calli were transferred to the medium of step 6 supplemented with 100 mg/l paromomycin and incubated in the light for several weeks.
8. Transgenic calli were selected and subcultured for several times in the same medium and conditions.
9. Regenerating shoots were isolated and propagated in MS salts including 30 g/l sucrose, 0.25 mg/l BAP and 100 mg/l kanamycin.
10. Green shoots were transferred to MS salts supplemented with 30 g/l sucrose, 0.1 mg/l BAP, 250 mg/l Timentin and 200 mg/l paromomycin in order to finish the selection phase and were multiplied regularly for several times in this media.

11. Leaf explants were isolated from the green growing shoots for DNA extraction and PCR analysis, in order to confirm the putative transgenic lines.
12. Selected shoots were rooted in MS salts supplemented with 0.5 mg/l IBA, 100 mg/l cefotaxime and 10 mg/l PPT and transferred to the green house for seed production.

b) Particle bombardment of sugar beet callus

1. Friable calli were produced as previously described in the method of 2.1.
2. An osmotic treatment was carried out for several hours.
3. Preparation and DNA coating of the gold particles was done by standard procedures, as describe in the PDS-1000/He instruction manual. The plasmids pZFN-nptII-GRF5 and pUbi4-tDT (containing a red fluorescent reporter) were coprecipitated with gold particles. As control, gold particles were coated with pUbi4tDT and pABM70STurboYFP (containing a yellow fluorescent reporter).
4. Calli were bombarded with a PDS-1000/He unit (Bio-Rad), using 30 ng gold particles coated with 500 ng DNA per shot.
5. To evaluate the effect of the transient expression of GRF5 in the shoot regeneration frequency, bombarded calli were incubated in MS salts supplemented with 30 g/l sucrose, 1 mg/l GA3 and 1 mg/l Thidiazuron in light conditions for c. 2 weeks. Shoot number was scored by using a standard binocular.

Results:

The *Agrobacterium tumefaciens*-mediated transformation of calli derived from micropropagated shoots of sugar beet with the construct pZFN-nptII-GRF5 increases the number of regenerated shoots at the end of the selection step significantly (Table 2). As control, the construct pZFN-tdT-nptII (Control) containing a red fluorescent reporter has been used. The five independent experiments show an increase of the on average transformation frequency from 5.0% to 33.9%. Further the number of transgenic events confirmed by PCR has been increased on average from 4.8 events to 25.4 events per transformation experiment.

TABLE 2

Transformation frequency of 5 independent experiments performed by the transformation method of a), either with a control construct or with the pZFN-nptII-GRF5. The total number of shoots at the end of the selection phase and total number of transgenic events confirmed by PCR are also shown. On average number of developing shoots, transgenic events and transformation frequency are indicated in bold.

| Experiment Name | # shoots at the end of selection | # confirmed transgenic lines | Transformation frequency (%) |
|---|---|---|---|
| Control_Rep01 | 9 | 3 | 5.5 |
| Control_Rep02 | 8 | 5 | 8.5 |
| Control_Rep03 | 11 | 5 | 3.3 |
| Control_Rep04 | 9 | 4 | 3.1 |
| Control_Rep05 | 13 | 7 | 4.7 |
| **Control average** | **10** | **4.8** | **5.0** |
| GRF5_Rep01 | 108 | 23 | 11.5 |
| GRF5_Rep02 | 61 | 28 | 35.0 |
| GRF5_Rep03 | 27 | 13 | 21.7 |
| GRF5_Rep04 | 167 | 35 | 38.9 |
| GRF5_Rep05 | 86 | 28 | 62.2 |
| **GRF5 average** | **89.8** | **25.4** | **33.9** |

In the callus transformation experiments the regeneration of shoots has been determined also for each individual selection step. The Quantification of regenerating shoots in each selection step shows that the overexpression of the GRF5 in calli of sugar beet accelerates the shoot organogenesis (Table 3, FIGS. 1 and 2). In another callus transformation experiment the regeneration of shoots has been determined for two recalcitrant sugar beet genotypes (FIG. 8): The transformation with construct pZFN-tdT-nptII (control) results in no transgenic shoot for genotype A and in only on average 0.3 shoots per callus for genotype B. Using AtGRF5 overexpression under the 70S promoter the average number of transgenic shoots is increased from 0 to 1.67 transgenic shoots for genotype A and from 0.3 to 4.82 shoots per callus for genotype B. This demonstrate impressively the potential of AtGRF5 and opens up the possibility to work genotype-independently with standard transformation methods.

Further experiments demonstrated that the number of transgenic events per inoculated callus could be increased by factor 9 by use of a construct for overexpression of AtGRF5 in *Beta vulgaris* calli (FIG. 9). As control, the construct pZFN-tdT-nptII (Control) containing a red fluorescent reporter has been used. The GRF gene as well as the reporter gene were under the control of the constitutive 70S promoter (double enhanced constitutive 35S promoter from Cauliflower mosaic virus).

The expression level of GRF5 has been determined in eleven, randomly chosen independent transgenic events of sugar beet. The expression analysis was performed with primers binding to the 3'-UTR of the NOS terminator. In all analyzed transgenic events a high level of GRF5 expression have been detected (see FIG. 4).

TABLE 3

Quantification of regenerating shoots in each selection step of 5 independent callus transformation experiments done either with pZFN-tdT-nptII (Ctrl) or pZFN-nptII-GRF5 (RB). Total number of developing shoots in each step are indicated in bold.

| | | SELECTION STEPS | | | |
|---|---|---|---|---|---|
| Experiment ID | Overexpressed gene | S1 | S2 | S3 | S4 |
| Ctrl-1 | tdTomato | 0 | 0 | 3 | 6 |
| Ctrl-2 | tdTomato | 0 | 1 | 3 | 4 |
| Ctrl-3 | tdTomato | 0 | 0 | 0 | 11 |
| Ctrl-4 | tdTomato | 0 | 0 | 4 | 5 |
| Ctrl-5 | tdTomato | 0 | 0 | 7 | 6 |
| **Ctrl-Total** | **tdTomato** | **0** | **1** | **17** | **32** |
| RB-1 | GRF5 | 0 | 40 | 41 | 27 |
| RB-2 | GRF5 | 0 | 11 | 20 | 30 |
| RB-3 | GRF5 | 0 | 9 | 11 | 7 |
| RB-4 | GRF5 | 0 | 65 | 77 | 25 |
| RB-5 | GRF5 | 2 | 27 | 23 | 34 |
| **RB-Total** | **GRF5** | **2** | **152** | **172** | **123** |

In a further experiment of callus regeneration five different transgenic events overexpressing AtGRF5 in sugar beet have been analyzed. As control, on the one hand two non-transgenic sugar beet lines (WT1 and WT2) and on the other hand a transgenic line overexpressing the tdT reporter protein were used. FIG. 9 A shows that the average callus formation frequency in the control lines and the transgenic AtGRF5 events were almost comparable, perhaps slightly enhanced in the transgenic events. In FIG. 9B the average number of transgenic shoots is presented. Four of the five AtGRF5 events show a significant increase in shoot formation compared the two controls. From FIG. 9C is becomes apparently that the positive effect on shoot formation is related to the expression level of AtGRF5 in the transgenic events.

In co-transformation experiments with the control construct 70S-tDT and the 70S-AtGRF5 has been stably integrated in the genome of sugar beet callus cells. The inoculation of callus in the co-transformation experiments was done with a mixture 1:1 of the *Agrobacterium* strains harboring each construct individually. The average co-transformation frequency was 31.5%. As shown in FIG. 17, the number of red fluorescent (tDT positive) events is around 8 times higher in the co-transformation than in the single transformation experiments.

The transformation via particle bombardment according to method of 2.2 showed that even the transient (over) expression of GRF5 results in a significant increase of transformation frequency. Bombarded calli show an improved regeneration capability. FIG. 3 shows that calli biolistically transformed with construct pZFN-nptII-GRF5 exhibit an increased number of regenerating shoots compared to calli with the control construct.

In additional callus transformation experiments the transformation frequency in sugar beet has been determined also using the construct pZFN-nptII-AtGRF5 compared with the same construct but expressing the GRF homolog from *Beta vulgaris* (BvGRF5). As control, the construct pZFN-tdT-nptII (Control) containing a red fluorescent reporter has been used. The GRF genes as well as the reporter gene were under the control of a constitutive 70S promoter. The experiments shown in FIG. 6 were stopped at an early selection phase. That explains why transformation efficiency of the tDT construct is 0%. For the construct AtGRF5 on average transformation frequency of 70% and for construct BvGRF5 on average transformation frequency of 32.5% could be achieved.

2. *Oryza sativa* Experiments

Constructs Used in the Binary Plasmid:

The binary vectors were produced by standard cloning procedures. Within the T-DNA of this vector, the cDNA encoding GRF5 (At3g13960) was cloned between a suitable promoter and terminator ensuring sufficient ectopic expression levels of the GRF5 protein in rice (=single constructs). The T-DNA also contains the GFP gene that was used for the selection of transgenic plant cells and tissues. Additionally, binary vectors were produced which carrying beside the cDNA encoding GRF5 (At3g13960) including the suitable promoter and terminator ensuring sufficient ectopic expression levels of the GRF5 protein in rice and a further gene of interest under the control of a promoter and terminator (=double (stack) constructs).

Seed Sterilization and Sowing:

Wild type green seeds have been incubated in 70% ethanol and shaked for approximately 1 minute. After removal of ethanol the seeds have been washed once with sterile mQ water. Then 30 ml of 6% sodium hypochlorite solution has been added and the seeds have been shaked for 40-60 minutes. After removal of the sodium hypochlorite solution seeds have been washed 3 to 5 times with sterile mQ.

After finishing sterilization (0-3 hours) the seeds have been dried on sterile filter paper and placed onto the surface of the induction medium R001. The incubation took place under continuous light (3000 lux) at 32° C. for 6 days.

Transformation & Co-Cultivation:

For explant preparation swollen embryo's (scutellum derived calli) from the wild type seeds suitable for transformation has been selected and transferred to liquid infection medium (R002) containing *Agrobacterium tumefaciens* transformed with the plasmid being incorporated into the plant cells for 1.5 minutes and then to the cocultivation plates (R003). The plates have been incubated for 3 days at 25° C. in darkness. Selection of resistant tissue Selection:

After 3 days on cocultivation the calli have been removed from the seeds, washed several times with sterile mQ water and once with sterile mQ water containing 250 mg/l cefotaxime and transferred to R004 selection medium. Incubation has been performed under continuous light (3000 lux) at 32° C. for 2 weeks.

Microcalli Isolation & Regeneration

By means of sterile forceps the microcalli have been transferred to R005 and incubated under continuous light (3000 lux) at 32° C. for 1 week. Thereafter GFP used as selection marker has been checked in the dark room. Healthy calli positive for GFP have been transfer to R006 and further incubated under continuous light (3000 lux) at 32° C. for 1 week. For continuous regeneration, the calli have been transferred to R007 for 3 weeks under continuous light (3000 lux) at 32° C. With sterile forceps, healthy plantlets have been pulled out and transferred to R008 for 2 weeks under continuous light (3000 lux) at 32° C. before the plantlets have been brought to the greenhouse.

TABLE 4

Composition of media R001 to R008.

| ingredients | supplier/stock code | final concentration | 1.00 l |
|---|---|---|---|
| R001 (solid) Induction medium | | | |
| N6 salts | Sigma - C1416 | | 4.00 g |
| N6 vitamins | Duchefa - C0401 | 1x | 1.00 ml |
| L-Proline | Sigma -P5607 | 2878 mg/l | 2.88 g |
| CasaminoAcids | BD - 223050 | 300 mg/l | 0.30 g |
| Sucrose | Duchefa - S0809 | 30 g/l | 30.00 g |
| pH | | | 5.80 |
| Gelrite | Duchefa - G1101.5 | 4 g/l | 4.00 g |
| 2,4-D (1 mg/ml) | Sigma - D7299 | 2 mg/l | 2000.00 µl |
| R002 (liquid) Infection medium (filter sterilized) | | | |
| N6 salts | Sigma - C1416 | 1x | 4.00 g |
| N6 vitamins | Duchefa - C0401 | 1x | 1.00 ml |
| CasaminoAcids | BD - 223050 | 300 mg/l | 0.30 g |

TABLE 4-continued

| Composition of media R001 to R008. | | | |
|---|---|---|---|
| ingredients | supplier/stock code | final concentration | 1.00 l |
| Sucrose | Duchefa - S0809 | 68.5 g/l | 68.50 g |
| D+-Glucose-Monohydrat | VWR - MERC1.08342.1000 | 36 g/l | 36.00 g |
| pH | | | 5.20 |
| acetosyringone (2M) | Sigma Aldrich 2478-38-8 | 100 µM | 66.00 µl |
| preparation of acetosyringone: 2M = 392 mg in 1 ml DMSO dus: 0.04 g in 100 µl DMSO | | | |
| R003 (solid) Co cultivation medium | | | |
| N6 salts | Sigma - C1416 | | 4.00 g |
| N6 vitamins | Duchefa - C0401 | 1x | 1.00 ml |
| CasaminoAcids | BD - 223050 | 300 mg/l | 0.30 g |
| Sucrose | Duchefa - S0809 | 30 g/l | 30.00 g |
| D+-Glucose-Monohydrat | VWR - MERC1.08342.1000 | 10 g/l | 10.00 g |
| pH | | | 5.20 |
| Gelrite | Duchefa - G1101.5 | 4 g/l | 4.00 g |
| acetosyringone (2M) | Sigma Aldrich 2478-38-8 | 100 µM | 66.00 µl |
| 2,4-D (1 mg/ml) | Sigma - D7299 | 2 mg/l | 2000.00 µl |
| preparation of acetosyringone: 2M = 392 mg in 1 ml DMSO dus: 0.04 g in 100 µl DMSO | | | |
| R004 selection medium (LBA nptII) | | | |
| N6 salts | Sigma - C1416 | | 4.00 g |
| N6 vitamins | Duchefa - C0401 | 1x | 1.00 ml |
| L-Proline | Duchefa - P0717 | 2878 mg/l | 2.88 g |
| CasaminoAcids | BD - 223050 | 300 mg/l | 0.30 g |
| Sucrose | Duchefa - S0809 | 30 g/l | 30.00 g |
| pH | | | 5.80 |
| agarose type 1 | Sigma - A6013 | 7 g/l | 7.00 g |
| 2,4-D (1 mg/ml) | Sigma - D7299 | 2 mg/l | 2000.00 µl |
| Cefotaxime (200 mg/ml) | Duchefa -C0111 | 100 mg/l | 500.00 µl |
| Vancomycin (100 mg/ml) | Duchefa - V0155 | 100 mg/l | 1000.00 µl |
| G418 disulfate (100 mg/ml) | Sigma - G1279 | 35 mg/l | 350.00 ul |
| R005 Pre-regeneration medium | | | |
| N6 salts | Sigma - C1416 | | 4.00 g |
| N6 vitamins | Duchefa - C0401 | 1x | 1.00 ml |
| L-Proline | Duchefa - P0717 | 500 mg/l | 0.50 g |
| CasaminoAcids | BD - 223050 | 300 mg/l | 0.30 g |
| Sucrose | Duchefa - S0809 | 30 g/l | 30.00 g |
| pH | | | 5.80 |
| agarose type 1 | Sigma - A6013 | 7 g/l | 7.00 g |
| Kinetin (1 mg/ml) | Sigma - K0753 | 2 mg/l | 2000.00 µl |
| NAA (1 mg/ml) | Duchefa - N0903 | 1 mg/l | 1000.00 µl |
| ABA | Sigma - A1049 | 5 mg/ml | 1000.00 µl |
| Cefotaxime (200 mg/ml) | Duchefa - C0111 | 100 mg/l | 500.00 µl |
| Vancomycin (100 mg/ml) | Duchefa - V0155 | 100 mg/l | 1000.00 µl |
| G418 disulfate (100 mg/ml) | Sigma - G1279 | 35 mg/l | 350.00 µl |
| R006 Regeneration medium with 10 g/l agarose | | | |
| MS salts | Duchefa - M0221 | 1x | 4.30 g |
| MS vitamins | Duchefa - 1000x/M0409 | 1x | 1.00 ml |
| CasaminoAcids | BD - 223050 | 2000 mg/l | 2.00 g |
| Sucrose | Duchefa - S0809 | 30 g/l | 30.00 g |
| Sorbitol | Duchefa S0807 | 30 g/l | 30.00 g |
| pH | | | 5.80 |
| agarose type 1 | Sigma - A6013 | 10 g/l | 10.00 g |
| Kinetin (1 mg/ml) | Sigma - K0753 | 2 mg/l | 2000.00 µl |
| NAA (1 mg/ml) | Duchefa - N0903 | 0.02 mg/l | 20.00 µl |
| Cefotaxime (200 mg/ml) | Duchefa - C0111 | 100 mg/l | 500.00 µl |
| Vancomycin (100 mg/ml) | Duchefa - V0155 | 100 mg/l | 1000.00 µl |
| G418 disulfate (100 mg/ml) | Sigma - G1279 | 20 mg/l | 200.00 µl |
| R007 Regeneration medium | | | |
| MS salts | Duchefa - M0221 | 1x | 4.30 g |
| MS vitamins | Duchefa - 1000x/M0409 | 1x | 1.00 ml |
| Sucrose | Duchefa - S0809 | 30 g/l | 30.00 g |
| pH | | | 5.80 |
| agarose type 1 | Sigma - A6013 | 7 g/l | 7.00 g |
| Cefotaxime (200 mg/ml) | Duchefa - C0111 | 100 mg/l | 500.00 µl |
| Vancomycin (100 mg/ml) | Duchefa - V0155 | 100 mg/l | 1000.00 µl |
| G418 disulfate (100 mg/ml) | Sigma - G1279 | 20 mg/l | 200.00 µl |

TABLE 4-continued

| Composition of media R001 to R008. | | | |
|---|---|---|---|
| ingredients | supplier/stock code | final concentration | 1.00 l |
| R008 Development medium | | | |
| MS salts | Duchefa - M0221 | 2.151045 g/l | 2.15 g |
| B5 vitamins (1000x stock) | Duchefa - G0415 | 0.5x | 0.50 ml |
| Sucrose | Duchefa - S0809 | 10 g/l | 10.00 g |
| NAA | Duchefa - N0903 | 0.05 mg/l | 50.00 μl |
| MgCl2.6H2O | VWR - MERC1 | 0.75 g/l | 0.75 g |
| pH | | | 5.80 |
| Gelrite | Duchefa - G1101.5 | 2.5 g/l | 2.50 g |

Results:

The *Agrobacterium tumefaciens*-mediated transformation of calli derived from immature embryos of rice with the different constructs containing GRF5 leads to a significant increase of the on average transformation frequency. As control or as comparison the transformation efficiency observed for 28 randomly selected other constructs without GRF5 has been used that shows a on average transformation efficiency of 63%. For 'single' constructs the transformation efficiency could be increased on average from 63% to 78%, for 'double' construct seven from 63% to 84% (Table 5).

TABLE 5

Transformation frequency of independent experiments, either with a single construct with GRF5 or with GRF5 in a stack with another gene XY in Rice. In total, 12 different genes in the stack with GRF5 from Arabidopsis thaliana ("GRF5", nucleotide sequence as set forth in SEQ ID NO: 1, amino acid sequence of SEQ ID NO: 2) have been tested, whereby 3 experiments have been repeated two times (indicated by Rep01 and Rep02). Also, GRF5 from Sorghum bicolor ("GRF5-Sorghum", nucleotide sequence as set forth in SEQ ID NO: 17, amino acid sequence of SEQ ID NO: 18) was tested alone and in a stack. On average transformation frequency are indicated in bold.

| Single/Stack | Gene #1 | Gene #2 | Transformation frequency [%] |
|---|---|---|---|
| Single | GRF5 | | 72 |
| Single | GRF5 | | 62 |
| Single | GRF5 | | 73 |
| Single | GRF5 | | 88 |
| Single | GRF5 | | 93 |
| | | **Average:** | **78** |
| Double | GRF5 | Gene XY-01 | 77 |
| Double | GRF5 | Gene XY-02 | 86 |
| Double | GRF5 | Gene XY-03_Rep01 | 91 |
| Double | GRF5 | Gene XY-03_Rep02 | 92 |
| Double | GRF5 | Gene XY-04 | 92 |
| Double | GRF5 | Gene XY-05_Rep01 | 75 |
| Double | GRF5 | Gene XY-05_Rep02 | 100 |
| Double | GRF5 | Gene XY-06 | 79 |
| Double | GRF5 | Gene XY-07 | 89 |
| Double | GRF5 | Gene XY-08 | 79 |
| Double | GRF5 | Gene XY-09 | 81 |
| Double | GRF5 | Gene XY-10_Rep01 | 80 |
| Double | GRF5 | Gene XY-10_Rep02 | 82 |
| Double | GRF5 | Gene XY-11 | 76 |
| Double | GRF5 | Gene XY-12 | 77 |
| | | **Average:** | **84** |
| Single | GRF5-Sorghum | | 67 |
| | | **Average:** | **67** |
| Double | GRF5-Sorghum | Gene XY-13 | 78 |
| | | **Average:** | **78** |
| Control: | | **Average:** | **63** |

3. *Zea mays* Experiments

Constructs Used in the Binary Plasmid:

The binary vectors were produced by standard cloning procedures. Within the T-DNA of these vectors, a) the cDNA encoding AtGRF5 (SEQ ID NO: 1), b) the synthetic DNA encoding ZmGRF5 (version A) (SEQ ID NO: 208), and c) the synthetic DNA encoding ZmGRF5 (version B) SEQ ID NO: 210) were cloned between a suitable promoter (e.g. BdEF1 promoter) and terminator ensuring sufficient ectopic expression levels of the GRF5 proteins in corn. As control a construct containing the tDT reporter gene under control of the 70S promoter with the ZmUbi Intron has been used.

Transformation:

The *Agrobacterium tumefaciens*-mediated transformation has been conducted by standard method of transforming monocotyledon by using scutellum of immature embryo (e.g., WO 95/06722).

Results:

As shown in FIG. 10 the *Agrobacterium tumefaciens*-mediated transformation of immature embryos with construct containing the GRF derived from *Arabidopsis thaliana* leads to a significant increase of the on average transformation frequency, from 8% to 14%. In contrast thereto, the use of the both ZmGRF5 versions derived from different *Zea mays* genotypes boosted the transformation efficiency much stronger. For version A of ZmGRF5 the efficiency is increased from 8% to 52%, and for version B of ZmGRF5 from 8% to 48%.

4. *Glycine max* (Soybean) Experiments

Soybean Transformation:

*Glycine max* transformation was performed using *Agrobacterium rhizogenes* for T-DNA delivery into the epicotyl's axillary meristem cells located at the primary-node of soybean seedlings of cultivar Jake (according to Olhoft P. M., Bernal L. M., Grist L. B., Hill D. S., Mankin S. L., Shen Y., Kalogerakis M., Wiley H., Toren E., Song H.-S., Hillebrand H., and Jones T. 2007, A novel *Agrobacterium rhizogenes*-mediated transformation method soybean [*Glycine max* (L.) Merrill] using primary-node explants from seedlings, In Vitro Cell. Dev. Biol.-Plant 43:536-549; US 2014237688, WO 2006024509, WO 2005121345).

Production of Binary Plasmids:

Three binary plasmids were produced by following standard cloning procedures. The first binary plasmid was the control plasmid used for the experiments (referred to the DsRed control) and is the base vector used for the other vectors. It contains within the T-DNA a DsRed gene that was used for phenotypic scoring of transgenic plant cells and tissues and the AtAHAS gene that was used for preferential selection of transgenic cells. Both genes were cloned with suitable promoter and terminators that ensure sufficient ectopic expression to serve abovementioned purposes. The second binary plasmid contains the base vector with the cDNA encoding AtGRF5 (SEQ ID NO. 2) cloned between a suitable promoter and terminator ensuring sufficient ectopic expression levels of the GRF5 protein in soybean. The third binary plasmid contains the base vector with the cDNA encoding GmGRF5 (SEQ ID NO. 106) cloned between a suitable promoter and terminator ensuring sufficient ectopic expression levels of the GRF5 protein in soybean.

Seed Sterilization and Germination:

Soybean seeds of 'Jake' cultivar were sterilized in a chamber with a chlorine gas produced by adding 3.5 ml 12N HCl into 100 ml bleach. After sterilization, approximately 65 seeds were plated on solid germination medium (1×B5 salts and vitamins, 2% sucrose, 0.8% Noble agar (A5431 Sigma-Aldrich®); pH 5.8) in PlantCons™. The seedlings were germinated in the light (150 $\mu m^{-2}s^{-2}$) at 26° C. for 7 days and used as explant material for transformation.

*Agrobacterium* Preparation:

*Agrobacterium rhizogenes* (WO 2006024509) was transformed with one of the following vectors containing: (1) pSUPER:DsRed and pPcUBI:AHAS selectable marker as a control, or the control vector plus either (2) pPcUbi-AtGRF5 or (3) pPcUBI-GmGRF5. *A. rhizogenes* was grown and resuspended in 50 ml liquid inoculation medium ($1/10^{th}$ B5 salts (G768 Phytotech), 3% sucrose, 20 mM MES, 1× Gamborg's vitamins, 200 μM acetosyringone, 1.44 μM gibberellic acid, 5.0 μM Kinetin; pH 5.4.) in a Falcon tube to an $OD_{600}$ of 1.5. The *Agrobacterium* suspension was then placed in a deep petri dish for receiving prepared explants.

Explant Preparation and Transformation:

Seedling explants were prepared from the 8-day-old seedlings by removing the roots and majority of the hypocotyl, one cotyledon, the axillary tissue growth at cotyledonary node, and the epicotyl above primary-node including all preformed leaves. After preparing the explants, approximately 45-50 explants were incubated with the *Agrobacterium* suspension in the petri dish for 30 minutes. Explants were then placed in petri dishes on a wet filter paper containing co-cultivation medium ($1/10^{th}$ B5 salts (G768 Phytotech), 3% sucrose, 20 mM MES, 0.5% Noble agar (A5431 Sigma-Aldrich®), 1× Gamborg's vitamins, 200 μM acetosyringone, 1.44 μM gibberellic acid, 5.0 μM kinetin, 4.1 mM L-cysteine, 0.5 mM dithiothrietol, 0.5 mM sodium thiosulfate; pH 5.4), and sealed in a container for 5 days at room temperature.

Shoot Development and Selection:

After 5 days, explants were transferred to selection medium (1×B5 salts and vitamins (G398 Phytotech), 3% sucrose, 3 mM MES, 1 μM 6-benzyl-aminopurine, 5 μM Kinetin, 250 mg/l Timentin STK, 3 μM imazapyr, 0.8% Noble agar (A5431 Sigma-Aldrich®); pH 5.6) five per plate and cultivated at 26° C. The explants had significant growth at the primary-node axillary meristem after 16 days on selection and were first scored for shoot development (regeneration). After 22 days on selection (the end of selection), the explants were removed from the solid media and placed on Oasis® growing media prior to scoring for (1) quality of shoot formation and (2) DsRed fluorescence on shoots developing at the primary-node.

Experimental Design and Results:

One experiment was conducted across four researchers and three constructs (Table 6). Soybean primary-node axillary meristems were transformed with DsRed control, AtGRF5, and GmGRF5. In total, 524 seedling explants were transformed and scored after 16 days on selection (21 days after transformation) and 22 days on selection (27 days after transformation). After 16 days on selection, shoots were rapidly growing at the primary-node and were a combination of small, compact shoot pads and larger, elongating shoots (FIG. 11). Regeneration [(number of explants with shoots)/total explants*100] at the target tissue, the primary-node, was between 80-100% for all constructs, and was fixed at 16 days on selection. Between 16 and 22 days, the shoots on the explants continued to grow rapidly. For both timepoints, the explants were subjectively scored for the presence of healthy, elongated shoot growth with a morphology ('good') that is predictive of successful formation of a rooted, transgenic plant (FIG. 12). There was an increase in 'good' shoot formation on explants transformed with all three constructs from the two timepoints, especially for explants transformed with AtGRF5 and GmGRF5. Across the four replicates, the explants transformed with either form of GRF5 tended to have more advanced shoot formation (larger shoots, more elongated) when compared to the DsRed control (FIG. 13).

To get an early measurement of transformation efficiencies, the explants were scored at 16 and 22 days on selection for the presence or absence of DsRed fluorescing shoots at the primary-node, which is due to transgenic cells expressing the DsRed protein. The DsRed expression was markedly more intense in the constructs containing AtGRF5 or GmGRF5 than the DsRed control at both timepoints; however more so at 16 days on selection (FIG. 11). The explants that were characterized as having 'good' shoot morphology generally had shoots that had DsRed expression (FIG. 11). The percent of explants with DsRed expressing shoots was significantly greater (at $\alpha$=0.05) in explants that were transformed with either AtGRF5 or GmGRF5 than compared to explants transformed with the DsRed control at both timepoints (Table 6; FIG. 14). Of the explants transformed with the DsRed control construct, 54.5% showed DsRed expressing shoots compared to 70.2% and 74.6% for AtGRF5 and GmGRF5, respectively, after 22 days on selection (Table 6). The data indicate that at 27 days after transformation, soybean explants transformed with either AtGRF5 or GmGRF5 have significantly more transgenic shoots regenerating at the primary-node than explants not transformed with either form of GRF5.

TABLE 6

Regeneration of transformed shoots was significantly increased in explants transformed with either AtGRF5 or GmGRF5 at 16 days and 22 days on selection. The mean and the range in regeneration and DsRed fluorescing shoots are shown.

| | | Regeneration (%)[1] | | Explants (%) with DsRed shoots[2] | | | |
|---|---|---|---|---|---|---|---|
| | | 16 d on selection | | 16 d on selection | | 22 d on selection | |
| Construct | n | Mean | Range (%) | Mean | Range (%) | Mean | Range (%) |
| DsRed control | 162 | 89.8 a | 81.8-95.2 | 31.4 a | 20.5-40.5 | 54.5 a | 50.0-57.1 |
| AtGRF5 | 180 | 88.4 a | 82.6-91.3 | 58.0 b | 52.2-66.7 | 70.2 b | 65.2-78.6 |
| GmGRF5 | 182 | 94.6 a | 85.4-100 | 53.3 b | 45.2-61.9 | 74.6 b | 62.5-86.0 |

Constructs that were significantly different (at $\alpha$ = 0.05) are followed with different letters;

[1]= [(number of explants with shoots at primary-node/total number {n} of explants inoculated) x 100];

[2]= [(number of explants with DsRed shoots at primary-node/total number {n} of explants inoculated) x 100]

5. *Brassica napus* (Canola) Experiments

Canola Transformation:

*Brassica napus* transformation was performed using *Agrobacterium rhizogenes* for T-DNA delivery into hypocotyl segments of *B. napus* seedlings of genotype BNS3.

Seed Sterilization and Germination:

Seeds were surface sterilized by placing 200-300 seeds for 2 minutes in 70% ethanol in a 50-mL Falcon tube. After gently shaking for 2 minutes, the ethanol was removed and 40 to 50 ml 30% Clorox bleach with 1 drop Tween was added. The seeds were incubated for 10 minutes with occasional mixing. The liquid was removed, then the seeds rinsed with sterile water three times before placing seeds on germination medium (½×MS salts/vitamins, 10 g $l^{-1}$ sucrose, Phyto Agar 7g $l^{-1}$; pH 5.8) in PlantCon boxes. The boxes were placed in a chamber for 4 to 5 days in the dark at 23° C.

*Agrobacterium* Preparation:

*Agrobacterium rhizogenes* was transformed with one of the following vectors: (1) pSUPER:DsRed and PcUBI:AHAS selectable marker as a control, or the control vector plus either (2) PcUbi-AtGRF5 or (3) PcUBI-BnGRF5 (SEQ ID NO. 108). *Agrobacterium rhizogenes* was grown to $OD_{600}$ of 1.0 and subsequently diluted to 0.1 with liquid infection medium (1×MS salts/vitamins, 30 g $l^{-1}$ sucrose; pH 5.8). The *Agrobacterium* suspension was then placed in a dish for receiving prepared hypocotyl explants.

Explant Preparation and Transformation:

Hypocotyl explants were prepared from the four to five-day etiolated seedlings by removing from germination box and placing on sterile filter paper wetted with infection medium without *Agrobacterium* to keep seedlings turgid. Hypocotyl segments 7 to 10 mm in length were prepared by after removing the root, cotyledon and epicotyl. After cutting, the explant was dipped in the *Agrobacterium* suspension, blotted on dry, sterile filter paper, and finally placed on filter paper on top of co-culture medium (1×MS salts/vitamins, 30 g $l^{-1}$ sucrose, 0.6 g $l^{-1}$ MES, 18 g I-mannitol, 7 g $l^{-1}$ Phyto Agar, 1 mg $l^{-1}$ 2,4-D, 100 mg $l^{-1}$ acetosyringone, 200 mg $l^{-1}$ L-cysteine; pH 5.6) in plates. Once~50 explants were plated, the plates were sealed with micropore tape and cultivated in the light at 23° C. at a 16 h light/8 h dark photoperiod for 3 days.

Callus Development and Shoot Initiation:

After 3 days, all explants were transferred to recovery medium (1×MS salts/vitamins, 30 g $l^{-1}$ sucrose, 0.6 g $l^{-1}$ MES, 18 g $l^{-1}$ mannitol, 7 g $l^{-1}$ Phyto Agar, 1 mg $l^{-1}$ 2,4-D, 300 mg $l^{-1}$ Timentin; pH 5.6), sealed with micropore tape, and cultivated at 23° C. for 7 days. Explants were transferred to selection medium #1 (1×MS salts/vitamins, 30 g $l^{-1}$ sucrose, 0.5 g $l^{-1}$ MES, 7 g $l^{-1}$ Phyto Agar, 3 mg $l^{-1}$ BAP, 0.1 mg $l^{-1}$ NAA, 0.1 mg $l^{-1}$ $GA_3$, 2.5 mg $l^{-1}$ $AgNO_3$, 100 nM imazethapyr, 300 mg $l^{-1}$ Timentin; pH 5.8) after one week, and cultivated for 14 days at 23° C. under 16 h light/8 h dark photoperiod. After two weeks of selection, the explants were transferred to Selection Medium 2 (1×MS salts/vitamins, 30 g $l^{-1}$ sucrose, 0.5 g $l^{-1}$ MES, 7 g $l^{-1}$ Phyto Agar, 0.5 mg $l^{-1}$ BAP, 0.1 mg $l^{-1}$ $GA_3$, 2.5 mg $l^{-1}$ $AgNO_3$, 100 nM imazethapyr, 300 mg $l^{-1}$ Timentin; pH 5.8).

Experimental Design and Results:

Five experiments over time were conducted across 3 researchers with a minimum of one replicate per researcher (Table Canola-1). In experiment 1, *Brassica napus* hypocotyls were transformed with DsRed control and BnGRF5 constructs for experiment 1 only; in the other experiments, explants were transformed with DsRed control, AtGRF5, and BnGRF5 constructs. In total, 3,156 explants were inoculated and scored for DsRed fluorescence after 16 to 22 days. At this point in time, explants were rapidly developing callus, especially on the cut ends of the hypocotyl. The explants were scored for presence or absence of DsRed fluorescence on explants, regardless of size, intensity, and frequency on a single explant. The frequency of DsRed expressing sectors is an early indicator of transformation efficiency for a treatment.

The DsRed expression was markedly more intense in the constructs containing AtGRF5 or BnGRF5 than the DsRed control (FIG. 15). The percent of explants with DsRed expressing shoots was significantly greater in explants that were transformed with either AtGRF5 or BnGRF5 than compared to explants transformed with the DsRed control (Table 7; FIG. 16). Of the explants transformed with the DsRed control construct, 20.1% showed DsRed expressing shoots compared to 56.6% and 58.5% for AtGRF5 and GmGRF5, respectively. The data indicate that at 21 days after transformation, *B. napus* explants transformed with either AtGRF5 or BnGRF5 have nearly 3-fold more transgenic callus sectors than explants not transformed with either form of GRF5 (statistically significant α=0.05). Significant differences between researchers and experiments was not detected across the treatments (constructs).

TABLE 7

Transformed callus was significantly increased on explants transformed with either AtGRF5 or BnGRF5 at 21 days after inoculation. The mean and the range in regeneration and DsRed fluorescing callus are shown.

| Construct | Exp. | Researchers | Replicates | Explants inoculated | Explants (%) with DsRed[1] Mean | Range |
|---|---|---|---|---|---|---|
| Control | 5 | 3 | 20 | 1202 | 20.1 a | 13-28.7 |
| AtGRF5 | 4 | 3 | 15 | 822 | 56.6 b | 40.8-70.3 |
| BnGRF5 | 5 | 3 | 20 | 1132 | 58.5 b | 44.0-78.4 |

Constructs that were significantly different (at α = 0.05) are followed with different letters;
[1]= [(number of explants with DsRed callus/total number {n} of explants inoculated) × 100].

The invention claimed is:

1. A method for transforming a plant cell, comprising (a) transforming a plant cell in parallel or sequentially with i. at least one nucleotide sequence of interest; and ii. an expression cassette comprising a polynucleotide encoding a Growth-Regulating Factor 5 (GRF5) polypeptide, wherein the at least one nucleotide sequence of interest is stably transformed into the plant cell and wherein the expression cassette comprising the polynucleotide encoding the GRF5 polypeptide is transiently transformed into the cell; and (b) cultivating the plant cell or a plant cell derived from the plant cell as in vitro tissue culture under conditions where in the plant cell the GRF5 polypeptide is expressed from the expression cassette, wherein the GRF5 polypeptide comprises the motif [D]-[PL]-[E]-[P]-[G]-[R]-[C]-[R]-[R]-[T]-[D]-[G]-[K]-[K]-[W]-[R]-[C]-[SA]-[RK]-[ED]-[A]-[YH]-[P]-[D]-[S]-[K]-[Y]-[C]-[E]-[KR]-[H]-[M]-[H]-[R]-[G]-[RK]-[N]-[R] (SEQ ID NO: 177) with a maximum number of three mismatches, and wherein the at least one nucleotide of interest encodes at least one phenotypic trait selected from the group consisting of resistance/tolerance to biotic stress, resistance/tolerance to abiotic stress, and modification of a further agronomic trait of interest.

2. A method of producing a transgenic plant, comprising the steps (a) transforming a plant cell according to the method of claim 1, and (b) regenerating from the plant cell of (a) or from a plant cell derived from the plant cell of (a) a plant comprising at least one cell which comprises the at least one nucleotide sequence of interest as transgene.

3. The method of claim 1, wherein the GRF5 polypeptide comprises a PFAM domain PF08880 and a PFAM domain PF08879.

4. The method of claim 3, wherein both the PFAM domain PF08880 and the PFAM domain PF08879 are located in the N-terminal half of the GRF5 polypeptide.

5. The method of claim 1, wherein the GRF5 polypeptide comprises an amino acid sequence comprising SEQ ID NO: 2, 4, 6, 8, 10, 12, 14, 16, 18, 20, 22, 24, 26, 28, 30, 32, 106, 108, 110, 112 or 209.

6. The method of claim 1, wherein the polynucleotide encoding the GRF5 polypeptide comprises a nucleotide sequence comprising SEQ ID NO: 1, 3, 5, 7, 9, 11, 13, 15, 17, 19, 21, 23, 25, 27, 29, 31, 105, 107, 109, 111, 207, 208 or 210.

7. The method of claim 1, wherein the polynucleotide encoding the GRF5 polypeptide is in operative linkage to at least one regulatory sequence suitable for expression of the GRF5 polypeptide in a plant cell.

8. The method of claim 1, wherein the plant cell of step (a) is a cell of a somatic tissue, callus tissue, a meristematic tissue or an embryonic tissue, or a protoplast.

9. A plant obtained or obtainable by the method of claim 2, or a progeny plant thereof, wherein the plant or progeny plant thereof comprises the at least one nucleotide sequence of interest and the expression cassette comprising a polynucleotide encoding a GRF5 polypeptide.

10. The method of claim 3, wherein the PFAM domain PF08880 finds a match of at least 90% coverage at or near the N-terminus of the GRF5 polypeptide and the PFAM domain PF08879 finds a match of at least 90% C-terminally located to the PFAM domain PF08880 in the GRF5 polypeptide.

11. The method of claim 4, wherein the PFAM domain PF08880 is located in the N-terminal quarter of the GRF5 polypeptide.

12. The method of claim 1, wherein the motif consists of any of the amino acid sequences SEQ ID NO: 41 to SEQ ID NO: 104 or SEQ ID NO: 113 to SEQ ID NO: 176 and/or wherein the motif contains a sub-region of amino acid stretch matching PFAM domain PF08879.

13. The method of claim 1, wherein the phenotypic trait is resistance/tolerance to biotic stress, and wherein the resistance/tolerance to biotic stress is pathogen resistance/tolerance.

14. The method of claim 13, wherein the pathogen resistance/tolerance is viral resistance/tolerance, bacterial resistance/tolerance, fungal resistance/tolerance, or animal pathogen resistance/tolerance.

15. The method of claim 1, wherein the phenotypic trait is resistance/tolerance to abiotic stress selected from the group consisting of chilling resistance/tolerance, drought stress resistance/tolerance, osmotic resistance/tolerance, heat stress resistance/tolerance, cold stress resistance/tolerance, frost stress resistance/tolerance, oxidative stress resistance/tolerance, heavy metal stress resistance/tolerance, salt stress resistance/tolerance, water logging resistance/tolerance, lodging resistance/tolerance, shattering resistance/tolerance, and resistance/tolerance against one or more herbicides.

16. The method of claim 1, wherein the phenotypic trait is modification of a further agronomic trait of interest selected from the group consisting of yield increase, flowering time modification, seed color modification, endosperm composition modification, nutritional content modification, and metabolic engineering of a pathway of interest.

* * * * *

SEQUENCE LISTING

```
<160> NUMBER OF SEQ ID NOS: 210

<210> SEQ ID NO 1
<211> LENGTH: 1194
<212> TYPE: DNA
```

<213> ORGANISM: Artificial Sequence
<220> FEATURE:
<223> OTHER INFORMATION: cDNA of AtGRF5

<400> SEQUENCE: 1

```
atgatgagtc taagtggaag tagcgggaga acaataggaa ggcctccatt tacaccaaca      60
caatgggaag aactggaaca tcaagcccta atctacaagt acatggtctc tggtgttcct     120
gtcccacctg agctcatctt ctccattaga agaagcttgg acacttcctt ggtctctaga     180
ctccttcctc accaatccct tggatggggg tgttaccaga tgggatttgg gagaaaacca     240
gatccagagc caggaagatg cagaagaaca gatggtaaga aatggagatg ctcaagagaa     300
gcttacccag attcgaagta ctgtgaaaaa cacatgcaca gaggaagaaa ccgtgccaga     360
aaatctcttg atcagaatca gacaacaaca actcctttaa catcaccatc tctctcattc     420
accaacaaca acaacccaag tcccaccttg tcttcttctt cttcctctaa ttcctcttct     480
actacttatt ctgcttcttc ttcttcaatg gatgcctaca gtaacagtaa taggtttggg     540
cttggtggaa gtagtagtaa cactagaggt tatttcaaca gccattctct tgattatcct     600
tatccttcta cttcacccaa acaacaacaa caaactcttc atcatgcttc cgctttgtca     660
cttcatcaaa atactaattc tacttctcag ttcaatgtct tagcctctgc tactgaccac     720
aaagacttca ggtactttca agggattggg gagagagttg gaggagttgg ggagagaacg     780
ttctttccag aagcatctag aagctttcaa gattctccat accatcatca ccaacaaccg     840
ttagcaacag tgatgaatga tccgtaccac cactgtagta ctgatcataa taagattgat     900
catcatcaca catactcatc ctcatcatca tctcaacatc ttcatcatga tcatgatcat     960
agacagcaac agtgttttgt tttgggcgcc gacatgttca acaaacctac aagaagtgtc    1020
cttgcaaact catcaagaca agatcaaaat caagaagaag atgagaaaga ttcatcagag    1080
tcgtccaaga agtctctaca tcacttcttt ggtgaggact gggcacagaa caagaacagt    1140
tcagattctt ggcttgacct ttcttcccac tcaagactcg acactggtag ctaa          1194
```

<210> SEQ ID NO 2
<211> LENGTH: 397
<212> TYPE: PRT
<213> ORGANISM: Arabidopsis thaliana

<400> SEQUENCE: 2

```
Met Met Ser Leu Ser Gly Ser Ser Gly Arg Thr Ile Gly Arg Pro Pro
1               5                   10                  15

Phe Thr Pro Thr Gln Trp Glu Glu Leu Glu His Gln Ala Leu Ile Tyr
            20                  25                  30

Lys Tyr Met Val Ser Gly Val Pro Val Pro Pro Glu Leu Ile Phe Ser
        35                  40                  45

Ile Arg Arg Ser Leu Asp Thr Ser Leu Val Ser Arg Leu Leu Pro His
    50                  55                  60

Gln Ser Leu Gly Trp Gly Cys Tyr Gln Met Gly Phe Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala Tyr Pro Asp Ser Lys Tyr Cys Glu Lys His Met
            100                 105                 110

His Arg Gly Arg Asn Arg Ala Arg Lys Ser Leu Asp Gln Asn Gln Thr
        115                 120                 125

Thr Thr Thr Pro Leu Thr Ser Pro Ser Leu Ser Phe Thr Asn Asn Asn
```

```
    130                 135                 140

Asn Pro Ser Pro Thr Leu Ser Ser Ser Ser Ser Ser Asn Ser Ser Ser
145                 150                 155                 160

Thr Thr Tyr Ser Ala Ser Ser Ser Ser Met Asp Ala Tyr Ser Asn Ser
                165                 170                 175

Asn Arg Phe Gly Leu Gly Gly Ser Ser Ser Asn Thr Arg Gly Tyr Phe
            180                 185                 190

Asn Ser His Ser Leu Asp Tyr Pro Tyr Pro Ser Thr Ser Pro Lys Gln
        195                 200                 205

Gln Gln Gln Thr Leu His His Ala Ser Ala Leu Ser Leu His Gln Asn
    210                 215                 220

Thr Asn Ser Thr Ser Gln Phe Asn Val Leu Ala Ser Ala Thr Asp His
225                 230                 235                 240

Lys Asp Phe Arg Tyr Phe Gln Gly Ile Gly Glu Arg Val Gly Gly Val
                245                 250                 255

Gly Glu Arg Thr Phe Phe Pro Glu Ala Ser Arg Ser Phe Gln Asp Ser
            260                 265                 270

Pro Tyr His His His Gln Gln Pro Leu Ala Thr Val Met Asn Asp Pro
        275                 280                 285

Tyr His His Cys Ser Thr Asp His Asn Lys Ile Asp His His His Thr
    290                 295                 300

Tyr Ser Ser Ser Ser Ser Ser Gln His Leu His His Asp His Asp His
305                 310                 315                 320

Arg Gln Gln Gln Cys Phe Val Leu Gly Ala Asp Met Phe Asn Lys Pro
                325                 330                 335

Thr Arg Ser Val Leu Ala Asn Ser Ser Arg Gln Asp Gln Asn Gln Glu
            340                 345                 350

Glu Asp Glu Lys Asp Ser Ser Glu Ser Ser Lys Lys Ser Leu His His
        355                 360                 365

Phe Phe Gly Glu Asp Trp Ala Gln Asn Lys Asn Ser Ser Asp Ser Trp
    370                 375                 380

Leu Asp Leu Ser Ser His Ser Arg Leu Asp Thr Gly Ser
385                 390                 395
```

<210> SEQ ID NO 3
<211> LENGTH: 1143
<212> TYPE: DNA
<213> ORGANISM: Artificial Sequence
<220> FEATURE:
<223> OTHER INFORMATION: cDNA of BvGRF5

<400> SEQUENCE: 3

```
atgagcactg ctacagcaac agtaggaggt ggtggtggtg gaggaagaag taaattccca     60

tttacagcaa cacaatggca agaacttgaa catcaagctc taatttataa gtatatggct    120

gctggtgttc ctattcctcc tgatcttctt ttcaccatca aacgtagtct tgactcttct    180

ctctcctcca agctctttcc ttaccaacct tctcctttgg gatggaaccc atatcaaatg    240

gggtatggaa aaaagataga cccagaacca ggaaggtgca gaagaacaga tgggaaaaaa    300

tggaggtgtt caaaagaagc atacccagat tcaaagtact gtgagaggca catgcataga    360

ggcaaaaacc gttcaagaaa gcctgtggaa tcacctttga ctacaacttc aactactgtt    420

tctaataaca acaataataa taataataat aataattctg ctgcaaattc atcactgaca    480

gtagcagctg ctgctgctgc agcatctttg accaatcaat cactgcttaa taagaatcct    540

tcttctgttt caacttctct cttttctctt ccttcctctg attcctcttg taattctcac    600
```

```
ctcctttatc cccattcttc ttacaatcac aaggactata gggaaaggta ttatcaagga    660

ttaaaagagg aggtgggaga gcatgcattt ttcacagaga gctcaggatc aagtatgaga    720

ggtttttcag gttcatccat ggatgaaagt tggcaaattg gtggtggaag taacatagat    780

catcatcaac aacaacaaca acaatcaaaa caaagtggtg ggtaccctaa ttacttgcag    840

cagcttcaaa gtaatagtac aactagtaat aatggtacat cagcaaagca ggagaagcaa    900

tgctacattt ggggaagaga ttttaactgt gatttatcaa tgaaggttga agaagaaaga    960

gaaaactttc atgaaaaaac cacccaccat ttctttgatg aatggcctat taaaagtggt   1020

ggaagaggag gaagagattc ttcatggcat gattcttctt caactactca actttccata   1080

tccattcctt cttctacttc tcatcatcat gactttttcc tcacaaattc tagggactcc   1140

taa                                                                 1143
```

<210> SEQ ID NO 4
<211> LENGTH: 380
<212> TYPE: PRT
<213> ORGANISM: Beta vulgaris

<400> SEQUENCE: 4

```
Met Ser Thr Ala Thr Ala Thr Val Gly Gly Gly Gly Gly Gly Gly Arg
1               5                   10                  15

Ser Lys Phe Pro Phe Thr Ala Thr Gln Trp Gln Glu Leu Glu His Gln
            20                  25                  30

Ala Leu Ile Tyr Lys Tyr Met Ala Ala Gly Val Pro Ile Pro Pro Asp
        35                  40                  45

Leu Leu Phe Thr Ile Lys Arg Ser Leu Asp Ser Ser Leu Ser Ser Lys
    50                  55                  60

Leu Phe Pro Tyr Gln Pro Ser Pro Leu Gly Trp Asn Pro Tyr Gln Met
65                  70                  75                  80

Gly Tyr Gly Lys Lys Ile Asp Pro Glu Pro Gly Arg Cys Arg Arg Thr
                85                  90                  95

Asp Gly Lys Lys Trp Arg Cys Ser Lys Glu Ala Tyr Pro Asp Ser Lys
            100                 105                 110

Tyr Cys Glu Arg His Met His Arg Gly Lys Asn Arg Ser Arg Lys Pro
        115                 120                 125

Val Glu Ser Pro Leu Thr Thr Thr Ser Thr Thr Val Ser Asn Asn Asn
    130                 135                 140

Asn Asn Asn Asn Asn Asn Asn Asn Ser Ala Ala Asn Ser Ser Leu Thr
145                 150                 155                 160

Val Ala Ala Ala Ala Ala Ala Ala Ser Leu Thr Asn Gln Ser Leu Leu
                165                 170                 175

Asn Lys Asn Pro Ser Ser Val Ser Thr Ser Leu Phe Ser Leu Pro Ser
            180                 185                 190

Ser Asp Ser Ser Cys Asn Ser His Leu Leu Tyr Pro His Ser Ser Tyr
        195                 200                 205

Asn His Lys Asp Tyr Arg Glu Arg Tyr Tyr Gln Gly Leu Lys Glu Glu
    210                 215                 220

Val Gly Glu His Ala Phe Phe Thr Glu Ser Ser Gly Ser Ser Met Arg
225                 230                 235                 240

Gly Phe Ser Gly Ser Ser Met Asp Glu Ser Trp Gln Ile Gly Gly Gly
                245                 250                 255

Ser Asn Ile Asp His His Gln Gln Gln Gln Gln Gln Ser Lys Gln Ser
            260                 265                 270
```

```
Gly Gly Tyr Pro Asn Tyr Leu Gln Gln Leu Gln Ser Asn Ser Thr Thr
        275                 280                 285

Ser Asn Asn Gly Thr Ser Ala Lys Gln Glu Lys Gln Cys Tyr Ile Trp
    290                 295                 300

Gly Arg Asp Phe Asn Cys Asp Leu Ser Met Lys Val Glu Glu Glu Arg
305                 310                 315                 320

Glu Asn Phe His Glu Lys Thr Thr His His Phe Phe Asp Glu Trp Pro
                325                 330                 335

Ile Lys Ser Gly Gly Arg Gly Gly Arg Asp Ser Ser Trp His Asp Ser
            340                 345                 350

Ser Ser Thr Thr Gln Leu Ser Ile Ser Ile Pro Ser Ser Thr Ser His
        355                 360                 365

His His Asp Phe Phe Leu Thr Asn Ser Arg Asp Ser
    370                 375                 380


<210> SEQ ID NO 5
<211> LENGTH: 1197
<212> TYPE: DNA
<213> ORGANISM: Artificial Sequence
<220> FEATURE:
<223> OTHER INFORMATION: cDNA of ZmGRF5

<400> SEQUENCE: 5

atgatgatga tgagcagcgg ccgggcgggc ggcggggcca ccgcggggcg gtacccgttc      60

acggcgtcgc agtggcagga gctggagcac caggcgctca tctacaagtg cctggcgtcc     120

ggcaagccca tcccttccta cctcatgccg ccgctccgcc gcatcctcga ctccgccctc     180

gccacgtcgc cgtccctcgc ctacccgccg caaccctcac tgggctgggg ctgcttcggg     240

atgggcttca cccggaaggc cgacgaggac ccggagcccg ggcggtgccg gcgcacggac     300

ggcaagaagt ggcgctgctc caaggaggcg tacccggact ccaagtactg cgagaagcac     360

atgcaccggg gcaagaaccg ttcaagaaag cctgtggaaa tgtccttggc cacgccggcc     420

ccggcgccgg cccccgccgc cgccacaacc gccaccgcca cctcatcccc ggcgccgtcc     480

taccaccgcc cggcccacga cgccacgccg tctccgtacc acgcgctgta tggaggcggc     540

ggcggcggcg gcggtagccc ttactcggcg tcggcacgcc caggagcaac cggaggcggc     600

ggcgcgtacc accacgcgca gcatgtgagc cccttccacc tccacctcga gaccacccac     660

ccgcacccgc cgccgcccta caactactcc gccgaccaga gggactacgc gtacgggcac     720

gcggccgcca aggaggtcgg cgagcacgcc ttcttctcgg acggcgcggg cgagcgggtc     780

gaccggcagg ccgcggcggg gcagtggcag ttcaggcagc tcggggtgga gacgaagccg     840

ggccccacgc cgctgttccc cgtcgccggg tacgggcacg gcgcggcgtc gccgtacggc     900

gtggagatgg gcaaggacga cgacgagcag gaggagaggc gccgccagca ctgcttcgtt     960

cttggagccg acctgcggct ggagcggccg tcgtcgggcc atggccatgg ccatgaccat    1020

gacgacgccg ccgccgcgca gaagccgctc cggccccttct tcgacgagtg gccgcaccag    1080

aagggggaca aggccgggtc gtggatgggg ctcgacggcg agacgcagct ctccatgtcc    1140

atccccatgg ccgccaccga cctccccgtc acctcccgct tccgtaacga cgagtga       1197


<210> SEQ ID NO 6
<211> LENGTH: 398
<212> TYPE: PRT
<213> ORGANISM: Zea mays

<400> SEQUENCE: 6
```

```
Met Met Met Met Ser Ser Gly Arg Ala Gly Gly Gly Ala Thr Ala Gly
1               5                   10                  15

Arg Tyr Pro Phe Thr Ala Ser Gln Trp Gln Glu Leu Glu His Gln Ala
            20                  25                  30

Leu Ile Tyr Lys Cys Leu Ala Ser Gly Lys Pro Ile Pro Ser Tyr Leu
        35                  40                  45

Met Pro Pro Leu Arg Arg Ile Leu Asp Ser Ala Leu Ala Thr Ser Pro
    50                  55                  60

Ser Leu Ala Tyr Pro Pro Gln Pro Ser Leu Gly Trp Gly Cys Phe Gly
65                  70                  75                  80

Met Gly Phe Thr Arg Lys Ala Asp Glu Asp Pro Glu Pro Gly Arg Cys
                85                  90                  95

Arg Arg Thr Asp Gly Lys Lys Trp Arg Cys Ser Lys Glu Ala Tyr Pro
            100                 105                 110

Asp Ser Lys Tyr Cys Glu Lys His Met His Arg Gly Lys Asn Arg Ser
        115                 120                 125

Arg Lys Pro Val Glu Met Ser Leu Ala Thr Pro Ala Pro Ala Pro Ala
    130                 135                 140

Pro Ala Ala Ala Thr Thr Ala Thr Ala Thr Ser Ser Pro Ala Pro Ser
145                 150                 155                 160

Tyr His Arg Pro Ala His Asp Ala Thr Pro Ser Pro Tyr His Ala Leu
                165                 170                 175

Tyr Gly Gly Gly Gly Gly Gly Gly Gly Ser Pro Tyr Ser Ala Ser Ala
            180                 185                 190

Arg Pro Gly Ala Thr Gly Gly Gly Gly Ala Tyr His His Ala Gln His
        195                 200                 205

Val Ser Pro Phe His Leu His Leu Glu Thr Thr His Pro His Pro Pro
    210                 215                 220

Pro Pro Tyr Asn Tyr Ser Ala Asp Gln Arg Asp Tyr Ala Tyr Gly His
225                 230                 235                 240

Ala Ala Ala Lys Glu Val Gly Glu His Ala Phe Phe Ser Asp Gly Ala
                245                 250                 255

Gly Glu Arg Val Asp Arg Gln Ala Ala Ala Gly Gln Trp Gln Phe Arg
            260                 265                 270

Gln Leu Gly Val Glu Thr Lys Pro Gly Pro Thr Pro Leu Phe Pro Val
        275                 280                 285

Ala Gly Tyr Gly His Gly Ala Ala Ser Pro Tyr Gly Val Glu Met Gly
    290                 295                 300

Lys Asp Asp Asp Glu Gln Glu Glu Arg Arg Arg Gln His Cys Phe Val
305                 310                 315                 320

Leu Gly Ala Asp Leu Arg Leu Glu Arg Pro Ser Ser Gly His Gly His
                325                 330                 335

Gly His Asp His Asp Asp Ala Ala Ala Ala Gln Lys Pro Leu Arg Pro
            340                 345                 350

Phe Phe Asp Glu Trp Pro His Gln Lys Gly Asp Lys Ala Gly Ser Trp
        355                 360                 365

Met Gly Leu Asp Gly Glu Thr Gln Leu Ser Met Ser Ile Pro Met Ala
    370                 375                 380

Ala Thr Asp Leu Pro Val Thr Ser Arg Phe Arg Asn Asp Glu
385                 390                 395
```

<210> SEQ ID NO 7
<211> LENGTH: 1245

<212> TYPE: DNA
<213> ORGANISM: Artificial Sequence
<220> FEATURE:
<223> OTHER INFORMATION: cDNA of TaGRF5

<400> SEQUENCE: 7

```
atgatgatga tgggtggtcg cgcgggggcc ggcggcgtcg gggcaggcgg ggggcggtgc      60

ccgttcacgg cgacgcagtg gcaggagctt gagcaccagg cactcatcta caagtacatg     120

gcctccggcg tgcccatccc ctccgacctc ctcctcccgc tccgccgcag cttcctcctc     180

gactccgccc tcgccacctc cccctccctc gccttccctc cccaggccgc acttggctgg     240

ggttgctttg gcatggggtt cggccggaag gcggaggacc cggagccggg gcggtgccgg     300

cggacggacg gcaagaagtg gcgctgctcc aaggaggcgt acccggactc caagtactgc     360

gagaagcaca tgcaccgcgg caagaaccgt tcaagaaagc ctgtggaaat gtccttggcc     420

acgcccccgc cgccgccttc ctcctcggcc tcctcctcct cctccaacgt ccactccgcc     480

gtcaacgtcg ccaccaccac ctcctccccc gcgccgtcct accaccgcca cgccgccgcg     540

actcacgaca cgacgcccta ccacgcgctc tacggcggcc cctactcctc cgccggccgc     600

cagcagcacg ctagcgccta ccaccacgcc gcgcaggtca gcccgttcca cctgcacctc     660

gacaccaccc acccgcaccc gccgccgtcc tactactcca gcatggacca cagcaaggac     720

agctacgcct acgggcacag cgtcaaggag gtgcacggcg gcggcgagca cgccttcttc     780

tcctccgacg tcaccaccga cagggaccat caccaccacc accatcagca ccaacaccac     840

gctagcgccg gcggcaacgg ccagtggcag ttcaagcagc tcggcggcat ggagccgaag     900

cagcataacc caacgtcgct cttccccggc tgcggcggct acggcaacaa cgcggcctac     960

gccatcgacc tgtccagcaa agaagaggac gaggagaagg agaggcggca gcagcagcag    1020

cactgcttcc tgctgggcgc cgacctgagg ctcgacaagc cgtcgtcggg gcacggcgac    1080

tccgccgacc agaagcctct ccggcccttc ttcgacgagt ggccgcacga gaagaccggg    1140

agcaaggggt cgtggatggg gctcgagggg gagacgcagc tctccatctc catcgccaac    1200

gaactcccca tcaccaccac ctcccgctac caccatggtg aatga                    1245
```

<210> SEQ ID NO 8
<211> LENGTH: 414
<212> TYPE: PRT
<213> ORGANISM: Triticum aestivum

<400> SEQUENCE: 8

```
Met Met Met Met Gly Gly Arg Ala Gly Ala Gly Gly Val Gly Ala Gly
1               5                   10                  15

Gly Gly Arg Cys Pro Phe Thr Ala Thr Gln Trp Gln Glu Leu Glu His
            20                  25                  30

Gln Ala Leu Ile Tyr Lys Tyr Met Ala Ser Gly Val Pro Ile Pro Ser
        35                  40                  45

Asp Leu Leu Leu Pro Leu Arg Arg Ser Phe Leu Leu Asp Ser Ala Leu
    50                  55                  60

Ala Thr Ser Pro Ser Leu Ala Phe Pro Pro Gln Ala Ala Leu Gly Trp
65                  70                  75                  80

Gly Cys Phe Gly Met Gly Phe Gly Arg Lys Ala Glu Asp Pro Glu Pro
                85                  90                  95

Gly Arg Cys Arg Arg Thr Asp Gly Lys Lys Trp Arg Cys Ser Lys Glu
            100                 105                 110

Ala Tyr Pro Asp Ser Lys Tyr Cys Glu Lys His Met His Arg Gly Lys
```

-continued

```
        115                 120                 125

Asn Arg Ser Arg Lys Pro Val Glu Met Ser Leu Ala Thr Pro Pro Pro
    130                 135                 140

Pro Pro Ser Ser Ser Ala Ser Ser Ser Ser Ser Asn Val His Ser Ala
145                 150                 155                 160

Val Asn Val Ala Thr Thr Thr Ser Ser Pro Ala Pro Ser Tyr His Arg
                165                 170                 175

His Ala Ala Ala Thr His Asp Thr Thr Pro Tyr His Ala Leu Tyr Gly
            180                 185                 190

Gly Pro Tyr Ser Ser Ala Gly Arg Gln Gln His Ala Ser Ala Tyr His
        195                 200                 205

His Ala Ala Gln Val Ser Pro Phe His Leu His Leu Asp Thr Thr His
    210                 215                 220

Pro His Pro Pro Pro Ser Tyr Tyr Ser Ser Met Asp His Ser Lys Asp
225                 230                 235                 240

Ser Tyr Ala Tyr Gly His Ser Val Lys Glu Val His Gly Gly Gly Glu
                245                 250                 255

His Ala Phe Phe Ser Ser Asp Val Thr Thr Asp Arg Asp His His His
            260                 265                 270

His His His Gln His Gln His His Ala Ser Ala Gly Gly Asn Gly Gln
        275                 280                 285

Trp Gln Phe Lys Gln Leu Gly Gly Met Glu Pro Lys Gln His Asn Pro
    290                 295                 300

Thr Ser Leu Phe Pro Gly Cys Gly Gly Tyr Gly Asn Asn Ala Ala Tyr
305                 310                 315                 320

Ala Ile Asp Leu Ser Ser Lys Glu Glu Asp Glu Glu Lys Glu Arg Arg
                325                 330                 335

Gln Gln Gln Gln His Cys Phe Leu Leu Gly Ala Asp Leu Arg Leu Asp
            340                 345                 350

Lys Pro Ser Ser Gly His Gly Asp Ser Ala Asp Gln Lys Pro Leu Arg
        355                 360                 365

Pro Phe Phe Asp Glu Trp Pro His Glu Lys Thr Gly Ser Lys Gly Ser
    370                 375                 380

Trp Met Gly Leu Glu Gly Glu Thr Gln Leu Ser Ile Ser Ile Ala Asn
385                 390                 395                 400

Glu Leu Pro Ile Thr Thr Thr Ser Arg Tyr His His Gly Glu
                405                 410


<210> SEQ ID NO 9
<211> LENGTH: 1170
<212> TYPE: DNA
<213> ORGANISM: Artificial Sequence
<220> FEATURE:
<223> OTHER INFORMATION: cDNA of BnGRF5

<400> SEQUENCE: 9

atgatgagtc taagtggaaa tggtgggaga acaatagaga ggcctccatt tacaccaaca      60

caatggcaag aactggagaa tcaagcccta atttacaagt acatggtctc aggagttcct     120

gtcccacctg agctcatctt ctccattaga agaagcttgg actcttcctt ggtctctaga     180

ctcctccctc accaatccat tgggtgggga tgctatcaga tggggtttgg tagaaaacca     240

gatccagaac caggaaggtg cagaagaaca gatggtaaga aatggagatg ctcaagagaa     300

gcatacccag attcaaagta ctgtgaaaaa cacatgcaca gaggaaggaa ccgtgccaga     360

aaatctattg atcagaatca gacaactgct cctttaacat caccatctct ctctttcccc     420
```

```
aacaacaaca acccaagccc taccttgtct tcttcctcct ctacttattc agctgcttct    480

tcatctcctt ccattgatgc ttacagtaat atcaataggc ttggtgttgg tagtagtaac    540

agtagaggtt acttcaacaa ccattccctt gactatcctt atcctttgtc ctcacctaaa    600

cagcaacaac aacagactct tcatcatgct tctgctttgt ctcttcacca aaacacatct    660

actgattctc agttcaatgc cttagcttct gcaactgacc ataaagactt cagatacttt    720

caagggattg gggagagagc tggagttgga gctggggaga ggactttttt tccagaagct    780

tctagaagct ttcaagattc tccataccat caccaacgac cgttagcaac agtaatgaat    840

gacccgtacc actctggtac tgatcataag gttgatcatc atcatcacac atactcatcc    900

gtatcatcat catctcagca tgatcaagat catcatcgac aacaacagca gcaatgtttt    960

gttatgggcg ctgacatgtt caacaaaccc acaagaactg tcttcgcaaa cacatcgagg   1020

caagatcatc aagaagagga ggagaaagat tcatcagaaa caaagaagtc tctacatcat   1080

ttctttggtg aggactgggc gcagaacaaa aacaattcag attcttggct tgacctttct   1140

tcccattcaa gactcgacac tggtagttga                                     1170


<210> SEQ ID NO 10
<211> LENGTH: 389
<212> TYPE: PRT
<213> ORGANISM: Brassica napus

<400> SEQUENCE: 10

Met Met Ser Leu Ser Gly Asn Gly Gly Arg Thr Ile Glu Arg Pro Pro
1               5                   10                  15

Phe Thr Pro Thr Gln Trp Gln Glu Leu Glu Asn Gln Ala Leu Ile Tyr
            20                  25                  30

Lys Tyr Met Val Ser Gly Val Pro Val Pro Pro Glu Leu Ile Phe Ser
        35                  40                  45

Ile Arg Arg Ser Leu Asp Ser Ser Leu Val Ser Arg Leu Leu Pro His
    50                  55                  60

Gln Ser Ile Gly Trp Gly Cys Tyr Gln Met Gly Phe Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala Tyr Pro Asp Ser Lys Tyr Cys Glu Lys His Met
            100                 105                 110

His Arg Gly Arg Asn Arg Ala Arg Lys Ser Ile Asp Gln Asn Gln Thr
        115                 120                 125

Thr Ala Pro Leu Thr Ser Pro Ser Leu Ser Phe Pro Asn Asn Asn Asn
    130                 135                 140

Pro Ser Pro Thr Leu Ser Ser Ser Ser Ser Thr Tyr Ser Ala Ala Ser
145                 150                 155                 160

Ser Ser Pro Ser Ile Asp Ala Tyr Ser Asn Ile Asn Arg Leu Gly Val
                165                 170                 175

Gly Ser Ser Asn Ser Arg Gly Tyr Phe Asn Asn His Ser Leu Asp Tyr
            180                 185                 190

Pro Tyr Pro Leu Ser Ser Pro Lys Gln Gln Gln Gln Gln Thr Leu His
        195                 200                 205

His Ala Ser Ala Leu Ser Leu His Gln Asn Thr Ser Thr Asp Ser Gln
    210                 215                 220

Phe Asn Ala Leu Ala Ser Ala Thr Asp His Lys Asp Phe Arg Tyr Phe
225                 230                 235                 240
```

```
Gln Gly Ile Gly Glu Arg Ala Gly Val Gly Ala Gly Glu Arg Thr Phe
                245                 250                 255

Phe Pro Glu Ala Ser Arg Ser Phe Gln Asp Ser Pro Tyr His His Gln
            260                 265                 270

Arg Pro Leu Ala Thr Val Met Asn Asp Pro Tyr His Ser Gly Thr Asp
        275                 280                 285

His Lys Val Asp His His His His Thr Tyr Ser Ser Val Ser Ser Ser
    290                 295                 300

Ser Gln His Asp Gln Asp His His Arg Gln Gln Gln Gln Gln Cys Phe
305                 310                 315                 320

Val Met Gly Ala Asp Met Phe Asn Lys Pro Thr Arg Thr Val Phe Ala
                325                 330                 335

Asn Thr Ser Arg Gln Asp His Gln Glu Glu Glu Glu Lys Asp Ser Ser
            340                 345                 350

Glu Thr Lys Lys Ser Leu His His Phe Phe Gly Glu Asp Trp Ala Gln
        355                 360                 365

Asn Lys Asn Asn Ser Asp Ser Trp Leu Asp Leu Ser Ser His Ser Arg
    370                 375                 380

Leu Asp Thr Gly Ser
385


<210> SEQ ID NO 11
<211> LENGTH: 1173
<212> TYPE: DNA
<213> ORGANISM: Artificial Sequence
<220> FEATURE:
<223> OTHER INFORMATION: cDNA of BrGRF5

<400> SEQUENCE: 11

atgatgagtc taagtggaaa tggtgggaga acaatagaga ggcctccatt tacaccaaca     60

caatggcaag aactggagaa tcaagcccta atttacaagt acatggtctc aggagttcct    120

gtcccacctg agctcatctt ctccattaga agaagcttgg actcttcctt ggtctctaga    180

ctcctccctc accaatccat tgggtgggga tgctatcaga tggggtttgg tagaaaacca    240

gatccagaac caggaaggtg cagaagaaca gatggtaaga aatggagatg ctcaagagaa    300

gcacatccag attctaagta ctgtgaaaaa cacatgcaca gaggaaggaa ccgtgccaga    360

aaatctattg atcagaatca gacaactgct cctttaacat caccatctct ctctttcccc    420

aacaacaaca acccaagccc taccttgtct tcttcctcct ctacttattc agcttcttct    480

tcatctcctt ccattgatgc ttacagtaat atcaataggc ttggtgttgg taatagtaac    540

agtagaggtt acttcaacaa ccattccctt gactatcctt atcctttgtc ctcacctaaa    600

cagcaacaac aacaacagac tcttcatcat gcttctgctt tgtctcttca ccaaaacgca    660

tctactgctt ctcagttcaa tgccttagct tctgcaactg accataaaga cttcagatac    720

tttcaaggga ttggggagag agttggagtt ggagctgggg agaggacttt ttttccagaa    780

gcttctagaa gctttcaaga ttctccatac catcaccaac aaccgttagc tacagtaatg    840

aatgacccgt tccactctgg tactgatcat aaggttgatc atcagcatca cacatactca    900

tccgtatcat catcatctca gcatgatcaa gatcatcatc gacaacaaca gcagcaatgt    960

tttgttatgg gcgctgacat gttcaacaaa cccacaagaa ctgtcttcgc aaactcatct   1020

agacaagatc atcaagaaga ggaggagaaa gattcatcag aaacaaagaa gtctctacat   1080

catttctttg gtgaggactg ggcacagaac aaaaacagtt cagattcttg gcttgacctt   1140
```

```
tcttcccatt caagactgga cactggtagt tga                                  1173


<210> SEQ ID NO 12
<211> LENGTH: 390
<212> TYPE: PRT
<213> ORGANISM: Brassica rapa

<400> SEQUENCE: 12

Met Met Ser Leu Ser Gly Asn Gly Gly Arg Thr Ile Glu Arg Pro Pro
1               5                   10                  15

Phe Thr Pro Thr Gln Trp Gln Glu Leu Glu Asn Gln Ala Leu Ile Tyr
            20                  25                  30

Lys Tyr Met Val Ser Gly Val Pro Val Pro Pro Glu Leu Ile Phe Ser
        35                  40                  45

Ile Arg Arg Ser Leu Asp Ser Ser Leu Val Ser Arg Leu Leu Pro His
    50                  55                  60

Gln Ser Ile Gly Trp Gly Cys Tyr Gln Met Gly Phe Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala His Pro Asp Ser Lys Tyr Cys Glu Lys His Met
            100                 105                 110

His Arg Gly Arg Asn Arg Ala Arg Lys Ser Ile Asp Gln Asn Gln Thr
        115                 120                 125

Thr Ala Pro Leu Thr Ser Pro Ser Leu Ser Phe Pro Asn Asn Asn Asn
    130                 135                 140

Pro Ser Pro Thr Leu Ser Ser Ser Ser Ser Thr Tyr Ser Ala Ser Ser
145                 150                 155                 160

Ser Ser Pro Ser Ile Asp Ala Tyr Ser Asn Ile Asn Arg Leu Gly Val
                165                 170                 175

Gly Asn Ser Asn Ser Arg Gly Tyr Phe Asn Asn His Ser Leu Asp Tyr
            180                 185                 190

Pro Tyr Pro Leu Ser Ser Pro Lys Gln Gln Gln Gln Gln Gln Thr Leu
        195                 200                 205

His His Ala Ser Ala Leu Ser Leu His Gln Asn Ala Ser Thr Ala Ser
    210                 215                 220

Gln Phe Asn Ala Leu Ala Ser Ala Thr Asp His Lys Asp Phe Arg Tyr
225                 230                 235                 240

Phe Gln Gly Ile Gly Glu Arg Val Gly Val Gly Ala Gly Glu Arg Thr
                245                 250                 255

Phe Phe Pro Glu Ala Ser Arg Ser Phe Gln Asp Ser Pro Tyr His His
            260                 265                 270

Gln Gln Pro Leu Ala Thr Val Met Asn Asp Pro Phe His Ser Gly Thr
        275                 280                 285

Asp His Lys Val Asp His Gln His His Thr Tyr Ser Ser Val Ser Ser
    290                 295                 300

Ser Ser Gln His Asp Gln Asp His His Arg Gln Gln Gln Gln Gln Cys
305                 310                 315                 320

Phe Val Met Gly Ala Asp Met Phe Asn Lys Pro Thr Arg Thr Val Phe
                325                 330                 335

Ala Asn Ser Ser Arg Gln Asp His Gln Glu Glu Glu Glu Lys Asp Ser
            340                 345                 350

Ser Glu Thr Lys Lys Ser Leu His His Phe Phe Gly Glu Asp Trp Ala
        355                 360                 365
```

```
Gln Asn Lys Asn Ser Ser Asp Ser Trp Leu Asp Leu Ser Ser His Ser
    370                 375                 380

Arg Leu Asp Thr Gly Ser
385                 390


<210> SEQ ID NO 13
<211> LENGTH: 1173
<212> TYPE: DNA
<213> ORGANISM: Artificial Sequence
<220> FEATURE:
<223> OTHER INFORMATION: cDNA of BoGRF5

<400> SEQUENCE: 13

atgatgagtc taagtggaaa tggtgggaga acaatagaga ggcctccatt tacaccaaca     60

caatggcaag aactggagaa tcaagcccta atttacaagt acatggtctc aggagttcct    120

gtcccacctg agctcatctt ctccattaga agaagcttgg actcttcctt ggtctctaga    180

ctcctccctc accaatccat tgggtgggga tgctatcaga tggggtttgg tagaaaacca    240

gatccagaac caggaaggtg cagaagaaca gatggtaaga aatggagatg ctcaagagaa    300

gcataccctg attcaaagta ctgtgaaaaa cacatgcaca gaggaaggaa ccgtgccaga    360

aaatctattg atcagaatca gacaactgct cctctaactt caccatctct ctctttcccc    420

aacaacaaca acccaagccc taccttgtcc tcttcctcct ctacttattc agcttcttct    480

tcatctcctt ccattgatgc ttacagtaat atcaataggc ttggtgttgg tagtagtaac    540

agtagaggtt acttcaacaa ccattccctt gagtatcctt atcctttgtc ctcacctaaa    600

cagcaacaac aacaacagac tcttcatcat gcttctgctt tgtctcttca ccaaaacaca    660

tctactgctt ctcagttcaa tgccttagct tctgcaaccg accataaaga cttcagatat    720

tttcaaggga ttggggagag agttggagtt ggagctgggg agagaacttt ttttccagaa    780

gcttctagaa gctttcaaga ttctccatac catcaccaac aaccgttagc aacagtaatg    840

agtgacccgt accactctgg tactgatcat aaggttgatc atcatcctca cacatactca    900

tccgtatcat catcatctca gcatgatcaa gatcatcatc gacaacaaca gcagcaatgt    960

tttgttatgg gcgctgacat gttcaacaaa ccccacaagaa ctggcttcgc aaacacatcg   1020

aggcaagatc atcaagaaga ggaggagaaa gattcatcag aaacaaagaa gtctctacat   1080

catttctttg gtgaggactg ggcgcagaac aaaaacaatt cagattcttg gcttgacctt   1140

tcttcccatt caagactcga cactggtagt tga                                 1173


<210> SEQ ID NO 14
<211> LENGTH: 390
<212> TYPE: PRT
<213> ORGANISM: Brassica oleracea

<400> SEQUENCE: 14

Met Met Ser Leu Ser Gly Asn Gly Gly Arg Thr Ile Glu Arg Pro Pro
1               5                   10                  15

Phe Thr Pro Thr Gln Trp Gln Glu Leu Glu Asn Gln Ala Leu Ile Tyr
            20                  25                  30

Lys Tyr Met Val Ser Gly Val Pro Val Pro Pro Glu Leu Ile Phe Ser
        35                  40                  45

Ile Arg Arg Ser Leu Asp Ser Ser Leu Val Ser Arg Leu Leu Pro His
    50                  55                  60

Gln Ser Ile Gly Trp Gly Cys Tyr Gln Met Gly Phe Gly Arg Lys Pro
65                  70                  75                  80
```

```
Asp Pro Glu Pro Gly Arg Cys Arg Arg Thr Asp Gly Lys Lys Trp Arg
                85                  90                  95

Cys Ser Arg Glu Ala Tyr Pro Asp Ser Lys Tyr Cys Glu Lys His Met
            100                 105                 110

His Arg Gly Arg Asn Arg Ala Arg Lys Ser Ile Asp Gln Asn Gln Thr
        115                 120                 125

Thr Ala Pro Leu Thr Ser Pro Ser Leu Ser Phe Pro Asn Asn Asn Asn
    130                 135                 140

Pro Ser Pro Thr Leu Ser Ser Ser Ser Ser Thr Tyr Ser Ala Ser Ser
145                 150                 155                 160

Ser Ser Pro Ser Ile Asp Ala Tyr Ser Asn Ile Asn Arg Leu Gly Val
                165                 170                 175

Gly Ser Ser Asn Ser Arg Gly Tyr Phe Asn Asn His Ser Leu Glu Tyr
            180                 185                 190

Pro Tyr Pro Leu Ser Ser Pro Lys Gln Gln Gln Gln Gln Gln Thr Leu
        195                 200                 205

His His Ala Ser Ala Leu Ser Leu His Gln Asn Thr Ser Thr Ala Ser
    210                 215                 220

Gln Phe Asn Ala Leu Ala Ser Ala Thr Asp His Lys Asp Phe Arg Tyr
225                 230                 235                 240

Phe Gln Gly Ile Gly Glu Arg Val Gly Val Gly Ala Gly Glu Arg Thr
                245                 250                 255

Phe Phe Pro Glu Ala Ser Arg Ser Phe Gln Asp Ser Pro Tyr His His
            260                 265                 270

Gln Gln Pro Leu Ala Thr Val Met Ser Asp Pro Tyr His Ser Gly Thr
        275                 280                 285

Asp His Lys Val Asp His His Pro His Thr Tyr Ser Ser Val Ser Ser
    290                 295                 300

Ser Ser Gln His Asp Gln Asp His His Arg Gln Gln Gln Gln Gln Cys
305                 310                 315                 320

Phe Val Met Gly Ala Asp Met Phe Asn Lys Pro Thr Arg Thr Gly Phe
                325                 330                 335

Ala Asn Thr Ser Arg Gln Asp His Gln Glu Glu Glu Glu Lys Asp Ser
            340                 345                 350

Ser Glu Thr Lys Lys Ser Leu His His Phe Phe Gly Glu Asp Trp Ala
        355                 360                 365

Gln Asn Lys Asn Asn Ser Asp Ser Trp Leu Asp Leu Ser Ser His Ser
    370                 375                 380

Arg Leu Asp Thr Gly Ser
385                 390
```

<210> SEQ ID NO 15
<211> LENGTH: 1197
<212> TYPE: DNA
<213> ORGANISM: Artificial Sequence
<220> FEATURE:
<223> OTHER INFORMATION: cDNA of RsGRF5

<400> SEQUENCE: 15

```
atgatgagtc taagtggaaa tggtgggaga acaatagaga ggcctccatt tacaccaaca     60

caatggcaag aactggagag tcaagcccta atttacaagt acatggtctc aggggttcct    120

gtcccacctg agctcatctt ctccattaga agaagcttgg actcttcctt ggtctctaga    180

ctcctccctc accaatctct tggctgggga tgctatcaga tgggatttgg tagaaaacca    240

gatccggaac caggaaggtg cagaagaaca gatggtaaga aatggagatg ctcaagagaa    300
```

```
gcatacccag attcaaagta ctgtgaaaaa cacatgcaca gaggaaggaa ccgtgccagg    360

aaatctattg atcagaatca gacaactgct cctttgacat caccatctct ctctttcccc    420

aacaacccaa gccctacctt gtcttcttct tcttctgcct ctacttattc tgctgcatct    480

tcatctcctt ctattgatgc tttcagtaat atcaataggc ctggtgttgg tagtagcatc    540

agcagaggtt acttcaacaa ccattccctt gactatcctt atcctttgtc ctcacctaaa    600

caacaacagc aacaacagac tcttcatcat gcttctgctt tgtcacttca ccaaaacaca    660

tctactgctt ctcagttcaa tgtcttagcc tcttcaactg accataaaga cttcagatac    720

tttcaaggga ttggggagag agttggagtt ggagttgggg agagaacatt ttttccagaa    780

gcttctagaa gctttcaaga ttctccatac catcaccaac aaccgttggc aacagtaatg    840

aatgacccgt accactgtag tactgatcac aaggttgatc atcatcacac atactcatcc    900

gcatcatcat cgtctcaaca tcaacatgat caagatcatg agcatagaca acaacagcag    960

caatgtttcg ttatgggtgc tgacatgttc aacaaaccca cacgaactgt cttcgcaaac   1020

acatcgagac aagatcaaga agaggaggag aaagattcat ctgaaaccaa gaagtctcta   1080

catcatttct ttggtgagga ctgggcgcag aacaagaaca gttcagattc ttggcttgat   1140

ctttcttccc actcaagact cgaccctggt agtaacctac attctgatct atgctaa      1197


<210> SEQ ID NO 16
<211> LENGTH: 398
<212> TYPE: PRT
<213> ORGANISM: Raphanus sativus

<400> SEQUENCE: 16

Met Met Ser Leu Ser Gly Asn Gly Gly Arg Thr Ile Glu Arg Pro Pro
1               5                   10                  15

Phe Thr Pro Thr Gln Trp Gln Glu Leu Glu Ser Gln Ala Leu Ile Tyr
            20                  25                  30

Lys Tyr Met Val Ser Gly Val Pro Val Pro Pro Glu Leu Ile Phe Ser
        35                  40                  45

Ile Arg Arg Ser Leu Asp Ser Ser Leu Val Ser Arg Leu Leu Pro His
    50                  55                  60

Gln Ser Leu Gly Trp Gly Cys Tyr Gln Met Gly Phe Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala Tyr Pro Asp Ser Lys Tyr Cys Glu Lys His Met
            100                 105                 110

His Arg Gly Arg Asn Arg Ala Arg Lys Ser Ile Asp Gln Asn Gln Thr
        115                 120                 125

Thr Ala Pro Leu Thr Ser Pro Ser Leu Ser Phe Pro Asn Asn Pro Ser
    130                 135                 140

Pro Thr Leu Ser Ser Ser Ser Ser Ala Ser Thr Tyr Ser Ala Ala Ser
145                 150                 155                 160

Ser Ser Pro Ser Ile Asp Ala Phe Ser Asn Ile Asn Arg Pro Gly Val
                165                 170                 175

Gly Ser Ser Ile Ser Arg Gly Tyr Phe Asn Asn His Ser Leu Asp Tyr
            180                 185                 190

Pro Tyr Pro Leu Ser Ser Pro Lys Gln Gln Gln Gln Gln Gln Thr Leu
        195                 200                 205

His His Ala Ser Ala Leu Ser Leu His Gln Asn Thr Ser Thr Ala Ser
```

```
    210                 215                 220

Gln Phe Asn Val Leu Ala Ser Ser Thr Asp His Lys Asp Phe Arg Tyr
225                 230                 235                 240

Phe Gln Gly Ile Gly Glu Arg Val Gly Val Gly Val Gly Glu Arg Thr
                245                 250                 255

Phe Phe Pro Glu Ala Ser Arg Ser Phe Gln Asp Ser Pro Tyr His His
            260                 265                 270

Gln Gln Pro Leu Ala Thr Val Met Asn Asp Pro Tyr His Cys Ser Thr
        275                 280                 285

Asp His Lys Val Asp His His His Thr Tyr Ser Ser Ala Ser Ser Ser
    290                 295                 300

Ser Gln His Gln His Asp Gln Asp His Glu His Arg Gln Gln Gln Gln
305                 310                 315                 320

Gln Cys Phe Val Met Gly Ala Asp Met Phe Asn Lys Pro Thr Arg Thr
                325                 330                 335

Val Phe Ala Asn Thr Ser Arg Gln Asp Gln Glu Glu Glu Glu Lys Asp
            340                 345                 350

Ser Ser Glu Thr Lys Lys Ser Leu His His Phe Phe Gly Glu Asp Trp
        355                 360                 365

Ala Gln Asn Lys Asn Ser Ser Asp Ser Trp Leu Asp Leu Ser Ser His
    370                 375                 380

Ser Arg Leu Asp Pro Gly Ser Asn Leu His Ser Asp Leu Cys
385                 390                 395


<210> SEQ ID NO 17
<211> LENGTH: 1182
<212> TYPE: DNA
<213> ORGANISM: Artificial Sequence
<220> FEATURE:
<223> OTHER INFORMATION: cDNA of SbGRF5

<400> SEQUENCE: 17

atgatgatga tgagcggtcg agcgggcggc ggcgccaccg cggggcggta cccgttcacg      60

gcgtcgcagt ggcaggagct ggagcaccag gcgctcatct acaagtgcct ggcgtctggc     120

aagcccatcc cgtcctacct catgccgccg ctccgccgca tcctcgactc cgccctcgcc     180

acgtcgccgt ccctcgcctt cccgccgcaa ccctcgttgg ggtggggctg tttcgggatg     240

ggcttcagca ggaagcccga cgaggacccg gagcccggcc ggtgccggcg gacggacggc     300

aagaagtggc gctgctccaa ggaggcgtac ccggactcca agtactgcga gaagcacatg     360

caccggggca agaaccgttc aagaaagcct gtggaaatgt ccttggccac accggcgccg     420

gcctctgcgg tgtcctccgc cacaagcgcc acagccgccg ccgccgccgc caccaccacc     480

acctcgtcgc cagcaccgtc ctaccgccca gcgcccacct cgcacgacgc ctcgccgtac     540

cacgcgctgt acggcggcgg cagtccgtac tcggcgtcgg cgcgtcccgc cggtggcccc     600

ggcccgtacc atcatcccgc gcaggtgagc cccttccacc tccacctcga gaccacccac     660

ccgcacccgc cgccgtccta ctactccgta gaccagcggg actacgcgta cgggcacgcc     720

accaaggagg tcgtcggcga gcacgccttc ttctccgatg gcgcggccga gcgggaccgc     780

cagcatgccg ccggccagtg gcagttcaag cagctcggga tggacacgaa gccgagcccc     840

acgtctctgt tccccgtcgc cgggtacggc aacggcgctg gtgcgtcgcc gtacggcgtt     900

gatctgggag ccaaggaaga cgacgaggaa gaaaggcggc gccagcagca gcagcactgc     960

ttcgttcttg gtgccgacct gcggctggag cggccgtcgt cgggccatga cgccgccacc    1020
```

```
gcgcagaagc cgctccggcc cttctttgac gagtggccgc acgagaaggg aaacaagggt   1080

gggtcatgga tggggcttga cggcgagacg cagctctcca tgtccatccc catggccgcc   1140

agcgacctcc ccgtcacctc ccgctaccgt aatgatgagt ga                      1182


<210> SEQ ID NO 18
<211> LENGTH: 393
<212> TYPE: PRT
<213> ORGANISM: Sorghum bicolor

<400> SEQUENCE: 18

Met Met Met Met Ser Gly Arg Ala Gly Gly Gly Ala Thr Ala Gly Arg
1               5                   10                  15

Tyr Pro Phe Thr Ala Ser Gln Trp Gln Glu Leu Glu His Gln Ala Leu
            20                  25                  30

Ile Tyr Lys Cys Leu Ala Ser Gly Lys Pro Ile Pro Ser Tyr Leu Met
        35                  40                  45

Pro Pro Leu Arg Arg Ile Leu Asp Ser Ala Leu Ala Thr Ser Pro Ser
    50                  55                  60

Leu Ala Phe Pro Pro Gln Pro Ser Leu Gly Trp Gly Cys Phe Gly Met
65                  70                  75                  80

Gly Phe Ser Arg Lys Pro Asp Glu Asp Pro Glu Pro Gly Arg Cys Arg
                85                  90                  95

Arg Thr Asp Gly Lys Lys Trp Arg Cys Ser Lys Glu Ala Tyr Pro Asp
            100                 105                 110

Ser Lys Tyr Cys Glu Lys His Met His Arg Gly Lys Asn Arg Ser Arg
        115                 120                 125

Lys Pro Val Glu Met Ser Leu Ala Thr Pro Ala Pro Ala Ser Ala Val
    130                 135                 140

Ser Ser Ala Thr Ser Ala Thr Ala Ala Ala Ala Ala Ala Thr Thr Thr
145                 150                 155                 160

Thr Ser Ser Pro Ala Pro Ser Tyr Arg Pro Ala Pro Thr Ser His Asp
                165                 170                 175

Ala Ser Pro Tyr His Ala Leu Tyr Gly Gly Gly Ser Pro Tyr Ser Ala
            180                 185                 190

Ser Ala Arg Pro Ala Gly Gly Pro Gly Pro Tyr His His Pro Ala Gln
        195                 200                 205

Val Ser Pro Phe His Leu His Leu Glu Thr Thr His Pro His Pro Pro
    210                 215                 220

Pro Ser Tyr Tyr Ser Val Asp Gln Arg Asp Tyr Ala Tyr Gly His Ala
225                 230                 235                 240

Thr Lys Glu Val Val Gly Glu His Ala Phe Phe Ser Asp Gly Ala Ala
                245                 250                 255

Glu Arg Asp Arg Gln His Ala Ala Gly Gln Trp Gln Phe Lys Gln Leu
            260                 265                 270

Gly Met Asp Thr Lys Pro Ser Pro Thr Ser Leu Phe Pro Val Ala Gly
        275                 280                 285

Tyr Gly Asn Gly Ala Gly Ala Ser Pro Tyr Gly Val Asp Leu Gly Ala
    290                 295                 300

Lys Glu Asp Asp Glu Glu Glu Arg Arg Arg Gln Gln Gln Gln His Cys
305                 310                 315                 320

Phe Val Leu Gly Ala Asp Leu Arg Leu Glu Arg Pro Ser Ser Gly His
                325                 330                 335

Asp Ala Ala Thr Ala Gln Lys Pro Leu Arg Pro Phe Phe Asp Glu Trp
            340                 345                 350
```

Pro His Glu Lys Gly Asn Lys Gly Gly Ser Trp Met Gly Leu Asp Gly
355 360 365

Glu Thr Gln Leu Ser Met Ser Ile Pro Met Ala Ala Ser Asp Leu Pro
370 375 380

Val Thr Ser Arg Tyr Arg Asn Asp Glu
385 390

<210> SEQ ID NO 19
<211> LENGTH: 1002
<212> TYPE: DNA
<213> ORGANISM: Artificial Sequence
<220> FEATURE:
<223> OTHER INFORMATION: cDNA of HaGRF5

<400> SEQUENCE: 19
atgatgagta caacagcagg tgaaggtgta aggaatcata gtggaaggta tcccttcaca 60
gccactcaat ggcaagaact tgaacatcaa gcacttgttt acaaatacat gatctctggt 120
atgcctatcc cccctgatct gcttttcacc atcaaaacaa gtctagattc ttctacaaag 180
ctcctccttc accaccagcc acctcatccc tcctcaattg gatggaactg cttccagatg 240
ggatttggga gaaaaataga tccagaacca ggaagatgca gaagaacaga tggtaagaaa 300
tggaggtgtt caaaagaagc ctatcctgat tcaaaatact gtgaaaggca catgcacaga 360
ggcagaaacc gttcaagaaa gcctgtggaa gtcaacatgt cgtcaacacc aacacccaaa 420
acaccaccaa ccgccattcc aatgatccca tcttccatct gtaccaaatc cccaaattac 480
ccttctccca attcacatcc actctcttct tcttcttctg actattacca taataataac 540
accacccacc ttccatctta ttctagacct tcttctaatg ttttcacaca agaccacttc 600
ttgttggatt ctagcccata catgagaaag ggtatggga tgaaagaggt gatagatgag 660
cactcatttt tctcagaatc ttctggaacc atcaagactg attcttggca attggaacca 720
ctggctatga acaattcatc ctcaaagcaa acaacttttt ctgattatca tcaaaacaga 780
tactcatatc aacaacagca agatccaggc tattatgatc aacaactggc tttgaaaatt 840
gacagaaatg atgaacccca gaaagtaatg caccatttct ttgatgaatg gccaccaaat 900
gatgataata acaaagattc ttcttccact actcagctct caatatccat ccccagttct 960
gctcgtgatt tcttcctctc acataatgct ggtgataaat ga 1002

<210> SEQ ID NO 20
<211> LENGTH: 333
<212> TYPE: PRT
<213> ORGANISM: Helianthus annuus

<400> SEQUENCE: 20

Met Met Ser Thr Thr Ala Gly Glu Gly Val Arg Asn His Ser Gly Arg
1 5 10 15

Tyr Pro Phe Thr Ala Thr Gln Trp Gln Glu Leu Glu His Gln Ala Leu
20 25 30

Val Tyr Lys Tyr Met Ile Ser Gly Met Pro Ile Pro Pro Asp Leu Leu
35 40 45

Phe Thr Ile Lys Thr Ser Leu Asp Ser Ser Thr Lys Leu Leu Leu His
50 55 60

His Gln Pro Pro His Pro Ser Ser Ile Gly Trp Asn Cys Phe Gln Met
65 70 75 80

Gly Phe Gly Arg Lys Ile Asp Pro Glu Pro Gly Arg Cys Arg Arg Thr
85 90 95

```
Asp Gly Lys Lys Trp Arg Cys Ser Lys Glu Ala Tyr Pro Asp Ser Lys
            100                 105                 110

Tyr Cys Glu Arg His Met His Arg Gly Arg Asn Arg Ser Arg Lys Pro
        115                 120                 125

Val Glu Val Asn Met Ser Ser Thr Pro Thr Pro Lys Thr Pro Pro Thr
    130                 135                 140

Ala Ile Pro Met Ile Pro Ser Ser Ile Cys Thr Lys Ser Pro Asn Tyr
145                 150                 155                 160

Pro Ser Pro Asn Ser His Pro Leu Ser Ser Ser Ser Ser Asp Tyr Tyr
                165                 170                 175

His Asn Asn Asn Thr Thr His Leu Pro Ser Tyr Ser Arg Pro Ser Ser
            180                 185                 190

Asn Val Phe Thr Gln Asp His Phe Leu Leu Asp Ser Ser Pro Tyr Met
        195                 200                 205

Arg Lys Gly Tyr Gly Met Lys Glu Val Ile Asp Glu His Ser Phe Phe
    210                 215                 220

Ser Glu Ser Ser Gly Thr Ile Lys Thr Asp Ser Trp Gln Leu Glu Pro
225                 230                 235                 240

Leu Ala Met Asn Asn Ser Ser Ser Lys Gln Thr Thr Phe Ser Asp Tyr
                245                 250                 255

His Gln Asn Arg Tyr Ser Tyr Gln Gln Gln Gln Asp Pro Gly Tyr Tyr
            260                 265                 270

Asp Gln Gln Leu Ala Leu Lys Ile Asp Arg Asn Asp Glu Pro Gln Lys
        275                 280                 285

Val Met His His Phe Phe Asp Glu Trp Pro Pro Asn Asp Asp Asn Asn
    290                 295                 300

Lys Asp Ser Ser Ser Thr Thr Gln Leu Ser Ile Ser Ile Pro Ser Ser
305                 310                 315                 320

Ala Arg Asp Phe Phe Leu Ser His Asn Ala Gly Asp Lys
                325                 330
```

<210> SEQ ID NO 21
<211> LENGTH: 1053
<212> TYPE: DNA
<213> ORGANISM: Artificial Sequence
<220> FEATURE:
<223> OTHER INFORMATION: cDNA of StGRF5

<400> SEQUENCE: 21

```
atggcggcgg agaatgggta cagaccgccg ttcacggcgg tgcagtggca ggaattggag     60

catcaagcaa tgatatataa gtatttggtg gcgggtattc cggtgccggc cgaccttgtt    120

gtacctatac gacgtagctt tgaacccatt tcagcgaggt tctttcatca tcctagcttg    180

ggttattgct cctattatgg gaagaagttt gatcctgagc caggaaggtg tagaaggaca    240

gatggaaaga agtggaggtg cgccaaagat gcatatcctg actcaaagta ttgcgagcgg    300

cacatgcatc gaggccgcaa ccgttcaaga aagcatgtgg aatctcaatc gactgcccag    360

tccttgttga ctagtatgtc acataatact actgggagca gcaaaacaag tggaaacttc    420

caacgtagca gtagtggcaa tttccaacgt agcagcagtg aaagcttcca gaacacgcca    480

ctatattctg ctgctaatac tgaaggacca agttatggaa gtgccacaac aaagatgcag    540

atggagcctg ccacctatgc agtagatagc aaggggtatt tccatggaat gactgctgat    600

gctgatgagc agaatttctc tctcgaagct tcggcaggca cgagaagttt agggatggga    660

tctaacacag acagcatgtg gtgtctgatg cctcctccac aacttccctc aagccccatg    720
```

```
gtgaaaccaa aaaatgattc acagttgcta gatagctcgc gacatatccg aatgcctaat    780

ccattcgagc ctatgaatga tacaactatt tcgggacaac accaacattg ctttttcagc    840

agtgacatag gctctcccgg gacagtaaag caggagcaac gttcaatgcg ccctttcttt    900

gacgaatggc ctacaactaa ggaatcatgg tccaatcttg atgatgaggg atccaacaaa    960

aataatttct ccactactca gctgtccata tccattccta tggctccttc tgacttctct   1020

tcaaggagtt cttgttcccc aaacgatgct tga                                1053


<210> SEQ ID NO 22
<211> LENGTH: 350
<212> TYPE: PRT
<213> ORGANISM: Solanum tuberosum

<400> SEQUENCE: 22

Met Ala Ala Glu Asn Gly Tyr Arg Pro Pro Phe Thr Ala Val Gln Trp
1               5                   10                  15

Gln Glu Leu Glu His Gln Ala Met Ile Tyr Lys Tyr Leu Val Ala Gly
            20                  25                  30

Ile Pro Val Pro Ala Asp Leu Val Val Pro Ile Arg Arg Ser Phe Glu
        35                  40                  45

Pro Ile Ser Ala Arg Phe Phe His His Pro Ser Leu Gly Tyr Cys Ser
    50                  55                  60

Tyr Tyr Gly Lys Lys Phe Asp Pro Glu Pro Gly Arg Cys Arg Arg Thr
65                  70                  75                  80

Asp Gly Lys Lys Trp Arg Cys Ala Lys Asp Ala Tyr Pro Asp Ser Lys
                85                  90                  95

Tyr Cys Glu Arg His Met His Arg Gly Arg Asn Arg Ser Arg Lys His
            100                 105                 110

Val Glu Ser Gln Ser Thr Ala Gln Ser Leu Leu Thr Ser Met Ser His
        115                 120                 125

Asn Thr Thr Gly Ser Ser Lys Thr Ser Gly Asn Phe Gln Arg Ser Ser
    130                 135                 140

Ser Gly Asn Phe Gln Arg Ser Ser Ser Glu Ser Phe Gln Asn Thr Pro
145                 150                 155                 160

Leu Tyr Ser Ala Ala Asn Thr Glu Gly Pro Ser Tyr Gly Ser Ala Thr
                165                 170                 175

Thr Lys Met Gln Met Glu Pro Ala Thr Tyr Ala Val Asp Ser Lys Gly
            180                 185                 190

Tyr Phe His Gly Met Thr Ala Asp Ala Asp Glu Gln Asn Phe Ser Leu
        195                 200                 205

Glu Ala Ser Ala Gly Thr Arg Ser Leu Gly Met Gly Ser Asn Thr Asp
    210                 215                 220

Ser Met Trp Cys Leu Met Pro Pro Pro Gln Leu Pro Ser Ser Pro Met
225                 230                 235                 240

Val Lys Pro Lys Asn Asp Ser Gln Leu Leu Asp Ser Ser Arg His Ile
                245                 250                 255

Arg Met Pro Asn Pro Phe Glu Pro Met Asn Asp Thr Thr Ile Ser Gly
            260                 265                 270

Gln His Gln His Cys Phe Phe Ser Ser Asp Ile Gly Ser Pro Gly Thr
        275                 280                 285

Val Lys Gln Glu Gln Arg Ser Met Arg Pro Phe Phe Asp Glu Trp Pro
    290                 295                 300

Thr Thr Lys Glu Ser Trp Ser Asn Leu Asp Asp Glu Gly Ser Asn Lys
```

305 310 315 320

Asn Asn Phe Ser Thr Thr Gln Leu Ser Ile Ser Ile Pro Met Ala Pro
325 330 335

Ser Asp Phe Ser Ser Arg Ser Ser Cys Ser Pro Asn Asp Ala
340 345 350

<210> SEQ ID NO 23
<211> LENGTH: 1242
<212> TYPE: DNA
<213> ORGANISM: Artificial Sequence
<220> FEATURE:
<223> OTHER INFORMATION: cDNA of HvGRF5

<400> SEQUENCE: 23
atgatgatga tgggcggtcg cgcgggggcc ggcggcgtgg gggcaggcgg ggggcggtgc 60
ccgttcacgg cgacgcagtg gcaggagctg gagcaccagg cgctcatcta caagtacatg 120
gcctccggcg tgcctatccc ctccgacctc ctcctcccgc tccgccgcag cttcctcctc 180
gactccgccc tcgccacctc cccctccctc gccttccctc cgcaggccac actgggctgg 240
ggttgcttcg ggatggggtt cggccggaag ccggaggacc cggagccggg gcggtgccgg 300
cggacggacg gcaagaagtg gcgctgctcc agggaggcgt acccagactc caagtactgc 360
gagaagcaca tgcaccgcgg caagaaccgt tcaagaaagc ctgtggaaat gtccttggcc 420
acgcccccgc cgccgccttc ctcctcggcc tcctcctcct cctccaacgt ccactccgcc 480
gtcaccgtcg ccaccaccac cacctccccc gcgccgtcct accaccgcca cgccgccacg 540
actcacgacg cggcacccta ccacgcgctc tacggcggcc cctacgcctc cgccggccgc 600
cagcagcacg ggagcgccta ccaccacgcc gcgcaggtca gcccgttcca cctgcacctc 660
gacaccaccc acccgcaccc gccgccgtcc tactactcca ccatggacca cagcaaggac 720
agctacgcct acgggcacag cgtcaaggag gtgcacggcg gcggcgagca cgccttcttc 780
tcctccgacg tcaccaccga cagggaccac cagcaccacc aacaccacgg cagcgccggc 840
ggccacggcc agtggcagtt caagcagctc ggcggcatgg agccgaagca gcacaacccc 900
acgtcgctct tccccgggtg cggcggctac ggcaacaacg cagcgtacgc catcgacctg 960
tccggcaaag aagaggccga ggagaaggag aggcggcagc agcagcagca ctgcttcctg 1020
ctgggcgctg acctgaggct cgacaagccg tcgtcggggc acggcgactc cgccgaccag 1080
aagcctctcc ggccgttctt cgacgagtgg ccgcacgaga agaccgggaa caaggggtca 1140
tggatggggc tcgagggcga gacccagctc tccatctcca tccccatgac cgccaacgac 1200
ctccccatca ccaccacctc ccgttaccac cacggtgaat ga 1242

<210> SEQ ID NO 24
<211> LENGTH: 413
<212> TYPE: PRT
<213> ORGANISM: Hordeum vulgare

<400> SEQUENCE: 24

Met Met Met Met Gly Gly Arg Ala Gly Ala Gly Gly Val Gly Ala Gly
1 5 10 15

Gly Gly Arg Cys Pro Phe Thr Ala Thr Gln Trp Gln Glu Leu Glu His
20 25 30

Gln Ala Leu Ile Tyr Lys Tyr Met Ala Ser Gly Val Pro Ile Pro Ser
35 40 45

Asp Leu Leu Leu Pro Leu Arg Arg Ser Phe Leu Leu Asp Ser Ala Leu
50 55 60

```
Ala Thr Ser Pro Ser Leu Ala Phe Pro Pro Gln Ala Thr Leu Gly Trp
65                  70                  75                  80

Gly Cys Phe Gly Met Gly Phe Gly Arg Lys Pro Glu Asp Pro Glu Pro
                85                  90                  95

Gly Arg Cys Arg Arg Thr Asp Gly Lys Lys Trp Arg Cys Ser Arg Glu
            100                 105                 110

Ala Tyr Pro Asp Ser Lys Tyr Cys Glu Lys His Met His Arg Gly Lys
        115                 120                 125

Asn Arg Ser Arg Lys Pro Val Glu Met Ser Leu Ala Thr Pro Pro Pro
    130                 135                 140

Pro Pro Ser Ser Ser Ala Ser Ser Ser Ser Ser Asn Val His Ser Ala
145                 150                 155                 160

Val Thr Val Ala Thr Thr Thr Thr Ser Pro Ala Pro Ser Tyr His Arg
                165                 170                 175

His Ala Ala Thr Thr His Asp Ala Ala Pro Tyr His Ala Leu Tyr Gly
            180                 185                 190

Gly Pro Tyr Ala Ser Ala Gly Arg Gln Gln His Gly Ser Ala Tyr His
        195                 200                 205

His Ala Ala Gln Val Ser Pro Phe His Leu His Leu Asp Thr Thr His
    210                 215                 220

Pro His Pro Pro Pro Ser Tyr Tyr Ser Thr Met Asp His Ser Lys Asp
225                 230                 235                 240

Ser Tyr Ala Tyr Gly His Ser Val Lys Glu Val His Gly Gly Gly Glu
                245                 250                 255

His Ala Phe Phe Ser Ser Asp Val Thr Thr Asp Arg Asp His Gln His
            260                 265                 270

His Gln His His Gly Ser Ala Gly Gly His Gly Gln Trp Gln Phe Lys
        275                 280                 285

Gln Leu Gly Gly Met Glu Pro Lys Gln His Asn Pro Thr Ser Leu Phe
    290                 295                 300

Pro Gly Cys Gly Gly Tyr Gly Asn Asn Ala Ala Tyr Ala Ile Asp Leu
305                 310                 315                 320

Ser Gly Lys Glu Glu Ala Glu Glu Lys Glu Arg Arg Gln Gln Gln Gln
                325                 330                 335

His Cys Phe Leu Leu Gly Ala Asp Leu Arg Leu Asp Lys Pro Ser Ser
            340                 345                 350

Gly His Gly Asp Ser Ala Asp Gln Lys Pro Leu Arg Pro Phe Phe Asp
        355                 360                 365

Glu Trp Pro His Glu Lys Thr Gly Asn Lys Gly Ser Trp Met Gly Leu
    370                 375                 380

Glu Gly Glu Thr Gln Leu Ser Ile Ser Ile Pro Met Thr Ala Asn Asp
385                 390                 395                 400

Leu Pro Ile Thr Thr Thr Ser Arg Tyr His His Gly Glu
                405                 410
```

<210> SEQ ID NO 25
<211> LENGTH: 1236
<212> TYPE: DNA
<213> ORGANISM: Artificial Sequence
<220> FEATURE:
<223> OTHER INFORMATION: cDNA of ScGRF5

<400> SEQUENCE: 25

```
atgatgatga tgggcggtcg cgcgggggcc ggcggcgtcg gggcaggcgg gggccggtgc      60
```

```
ccgttcacgg cgacgcagtg gcaggagctg gagcaccagg cgctcatcta caagtacatg    120

gcctccggcg tgcccatccc ctccgacctc ctcctcccgc tccgccgcag cttcctcctc    180

gactccgccc tcgccacctc cccctccctc gccttccctc cccaggccgc acttggatgg    240

ggctgcttcg ggatggggtt cggccggaag gcggaggacc cggagccggg gcggtgccgg    300

cggacggacg gcaagaagtg gcgctgctcc aaggaggcgt acccggactc caagtactgc    360

gagaagcaca tgcaccgcgg caagaaccgt tcaagaaagc ctgtggaaat gtccttggcc    420

acgcccccgc cgccgccttc ctcctcggcc tcctcctcct cctccaacgt ccactccgcc    480

gtcaacgtcg ccaccaccac ctcctccccc gcgccatcct accaccgcca cgccgccgcg    540

actcacgaca cgacgcccta ccacgcgctc tacggcggcc cctacgcctc tgccggccgc    600

cagcagcacg ccagcgccta ccaccacgcc gcgcaggtca gcccgttcca cctgcacctc    660

gacaccaccc acccgcaccc gccgccgtcc tactactcca ccatggacca cagcaaggac    720

agctacgcct acgggcacag cgtcaaggag gtgcacggcg gcggcgagca cgccttcttc    780

gcctccgacg tcgccaccga cagggaccac caccaccacc accaacacca cgccggcgcc    840

ggcggcaacg gccaatggca gttcaagcag ctcggcggca tggagcccaa gcagcataac    900

cccacgtcgc tcttccccgg ctgcggcggc tacggcaaca acgcggcgta cgccatcgac    960

ctgtccagca aagaagagga cgaggagaag gagaggcggc agcagcagca gcactgcttc   1020

ctgctgggcg ccgacctgag gctcgacaag ccgtcgtcgg ggcacggcga ctccgccgac   1080

cagaagcccc tccggccgtt cttcgacgag tggccgcacg agaaggccgg gagcaagggg   1140

tcgtggatgg ggctcgaggg ggagacgcag ctctccatct ccatcgccaa cgaactcccc   1200

atcaccacca cctcccgcta ccaccatggt gaatga                             1236
```

<210> SEQ ID NO 26
<211> LENGTH: 411
<212> TYPE: PRT
<213> ORGANISM: Secale cereale

<400> SEQUENCE: 26

```
Met Met Met Met Gly Gly Arg Ala Gly Ala Gly Gly Val Gly Ala Gly
1               5                   10                  15

Gly Gly Arg Cys Pro Phe Thr Ala Thr Gln Trp Gln Glu Leu Glu His
            20                  25                  30

Gln Ala Leu Ile Tyr Lys Tyr Met Ala Ser Gly Val Pro Ile Pro Ser
        35                  40                  45

Asp Leu Leu Leu Pro Leu Arg Arg Ser Phe Leu Leu Asp Ser Ala Leu
    50                  55                  60

Ala Thr Ser Pro Ser Leu Ala Phe Pro Pro Gln Ala Ala Leu Gly Trp
65                  70                  75                  80

Gly Cys Phe Gly Met Gly Phe Gly Arg Lys Ala Glu Asp Pro Glu Pro
                85                  90                  95

Gly Arg Cys Arg Arg Thr Asp Gly Lys Lys Trp Arg Cys Ser Lys Glu
            100                 105                 110

Ala Tyr Pro Asp Ser Lys Tyr Cys Glu Lys His Met His Arg Gly Lys
        115                 120                 125

Asn Arg Ser Arg Lys Pro Val Glu Met Ser Leu Ala Thr Pro Pro Pro
    130                 135                 140

Pro Pro Ser Ser Ser Ala Ser Ser Ser Ser Ser Asn Val His Ser Ala
145                 150                 155                 160

Val Asn Val Ala Thr Thr Thr Ser Ser Pro Ala Pro Ser Tyr His Arg
```

```
                165                 170                 175

His Ala Ala Ala Thr His Asp Thr Thr Pro Tyr His Ala Leu Tyr Gly
            180                 185                 190

Gly Pro Tyr Ala Ser Ala Gly Arg Gln Gln His Ala Ser Ala Tyr His
        195                 200                 205

His Ala Ala Gln Val Ser Pro Phe His Leu His Leu Asp Thr Thr His
    210                 215                 220

Pro His Pro Pro Pro Ser Tyr Tyr Ser Thr Met Asp His Ser Lys Asp
225                 230                 235                 240

Ser Tyr Ala Tyr Gly His Ser Val Lys Glu Val His Gly Gly Gly Glu
                245                 250                 255

His Ala Phe Phe Ala Ser Asp Val Ala Thr Asp Arg Asp His His His
            260                 265                 270

His His Gln His His Ala Gly Ala Gly Gly Asn Gly Gln Trp Gln Phe
        275                 280                 285

Lys Gln Leu Gly Gly Met Glu Pro Lys Gln His Asn Pro Thr Ser Leu
    290                 295                 300

Phe Pro Gly Cys Gly Gly Tyr Gly Asn Asn Ala Ala Tyr Ala Ile Asp
305                 310                 315                 320

Leu Ser Ser Lys Glu Glu Asp Glu Glu Lys Glu Arg Arg Gln Gln Gln
                325                 330                 335

Gln His Cys Phe Leu Leu Gly Ala Asp Leu Arg Leu Asp Lys Pro Ser
            340                 345                 350

Ser Gly His Gly Asp Ser Ala Asp Gln Lys Pro Leu Arg Pro Phe Phe
        355                 360                 365

Asp Glu Trp Pro His Glu Lys Ala Gly Ser Lys Gly Ser Trp Met Gly
    370                 375                 380

Leu Glu Gly Glu Thr Gln Leu Ser Ile Ser Ile Ala Asn Glu Leu Pro
385                 390                 395                 400

Ile Thr Thr Thr Ser Arg Tyr His His Gly Glu
                405                 410
```

<210> SEQ ID NO 27
<211> LENGTH: 1083
<212> TYPE: DNA
<213> ORGANISM: Artificial Sequence
<220> FEATURE:
<223> OTHER INFORMATION: cDNA of GmGRF5

<400> SEQUENCE: 27

```
atgatgagtg caagtgcagg tgcaagaaat aggtctccgt tcacacaaat tcagtggcaa     60

gagcttgagc aacaagctct tgtttttaag tacatggtta caggaacacc tatcccacca    120

gatctcatct actctattaa aagaagtcta gacacttcaa tttcttcaag gctcttccca    180

catcatccaa ttgggtgggg atgttttgaa atgggatttg gcagaaaagt agacccagag    240

ccagggaggt gcagaagaac agatggcaag aaatggagat gttcaaagga ggcatatcca    300

gactcaaagt actgtgaaag acacatgcac agaggcagaa accgttcaag aaagcctgtg    360

gaagtttctt cagcaacaag caccgccaca aacacctccc aaacaatccc atcatcttat    420

accagaaacc tttccttgac caataacagt aaccccaaca taacaccacc accaccaccc    480

tcttctttcc ctttctctca tttgccctct tctatgccta ttgatcagtc ccaacccttt    540

tcccaatcct accaaaactc ttctctcaat cccttcttct actcccaatc aacctcctct    600

agacccccag atgctgattt tccaccccaa gatgccacca cccaccacct attcatggac    660
```

-continued

```
tctgctggct cttattctca tgatgaaaag aattatagca ggcatgttca tggaataagg    720

gaagatgtgg atgagagagc tttcttccca gaagcatcag gatcagctag gagctataca    780

gactcgtacc aacaactatc aatgagctcc tacaagtcct attcaaactc caactttcag    840

aacattaata atgatgccac caccaaccca agacagcaag agcagcaact acaacaacaa    900

caacactgtt ttgttttagg gacagacttc aaatcaacaa ggccaagcaa agagaaagaa    960

gctgagacaa caacaggtca gagacccctt caccgtttct ttggggagtg gccaccaaag   1020

aacacaacaa cagattcctg gctagatctt gcttccaact ccagaatcca aaccgatgaa   1080

tga                                                                 1083
```

<210> SEQ ID NO 28
<211> LENGTH: 360
<212> TYPE: PRT
<213> ORGANISM: Glycine max

<400> SEQUENCE: 28

```
Met Met Ser Ala Ser Ala Gly Ala Arg Asn Arg Ser Pro Phe Thr Gln
1               5                   10                  15

Ile Gln Trp Gln Glu Leu Glu Gln Gln Ala Leu Val Phe Lys Tyr Met
            20                  25                  30

Val Thr Gly Thr Pro Ile Pro Pro Asp Leu Ile Tyr Ser Ile Lys Arg
        35                  40                  45

Ser Leu Asp Thr Ser Ile Ser Ser Arg Leu Phe Pro His His Pro Ile
    50                  55                  60

Gly Trp Gly Cys Phe Glu Met Gly Phe Gly Arg Lys Val Asp Pro Glu
65                  70                  75                  80

Pro Gly Arg Cys Arg Arg Thr Asp Gly Lys Lys Trp Arg Cys Ser Lys
                85                  90                  95

Glu Ala Tyr Pro Asp Ser Lys Tyr Cys Glu Arg His Met His Arg Gly
            100                 105                 110

Arg Asn Arg Ser Arg Lys Pro Val Glu Val Ser Ser Ala Thr Ser Thr
        115                 120                 125

Ala Thr Asn Thr Ser Gln Thr Ile Pro Ser Ser Tyr Thr Arg Asn Leu
    130                 135                 140

Ser Leu Thr Asn Asn Ser Asn Pro Asn Ile Thr Pro Pro Pro Pro Pro
145                 150                 155                 160

Ser Ser Phe Pro Phe Ser His Leu Pro Ser Ser Met Pro Ile Asp Gln
                165                 170                 175

Ser Gln Pro Phe Ser Gln Ser Tyr Gln Asn Ser Ser Leu Asn Pro Phe
            180                 185                 190

Phe Tyr Ser Gln Ser Thr Ser Ser Arg Pro Pro Asp Ala Asp Phe Pro
        195                 200                 205

Pro Gln Asp Ala Thr Thr His His Leu Phe Met Asp Ser Ala Gly Ser
    210                 215                 220

Tyr Ser His Asp Glu Lys Asn Tyr Ser Arg His Val His Gly Ile Arg
225                 230                 235                 240

Glu Asp Val Asp Glu Arg Ala Phe Phe Pro Glu Ala Ser Gly Ser Ala
                245                 250                 255

Arg Ser Tyr Thr Asp Ser Tyr Gln Gln Leu Ser Met Ser Ser Tyr Lys
            260                 265                 270

Ser Tyr Ser Asn Ser Asn Phe Gln Asn Ile Asn Asn Asp Ala Thr Thr
        275                 280                 285

Asn Pro Arg Gln Gln Glu Gln Gln Leu Gln Gln Gln Gln His Cys Phe
```

```
    290                 295                 300

Val Leu Gly Thr Asp Phe Lys Ser Thr Arg Pro Ser Lys Glu Lys Glu
305                 310                 315                 320

Ala Glu Thr Thr Thr Gly Gln Arg Pro Leu His Arg Phe Phe Gly Glu
                325                 330                 335

Trp Pro Pro Lys Asn Thr Thr Thr Asp Ser Trp Leu Asp Leu Ala Ser
            340                 345                 350

Asn Ser Arg Ile Gln Thr Asp Glu
        355                 360


<210> SEQ ID NO 29
<211> LENGTH: 945
<212> TYPE: DNA
<213> ORGANISM: Artificial Sequence
<220> FEATURE:
<223> OTHER INFORMATION: cDNA of GhGRF5

<400> SEQUENCE: 29

atgattagtg ccagaaataa gtaccttttc actccaaatc aatggcaaga gcttgaacac      60

caagctctca tcttcaaata catggtttca ggagttccta tcccacctca actcctttat     120

tctgtcaaaa caagctttga ttcttctttg gcttcacacc tcttccctca ccaacccaca     180

gggtggggct gttttcaggt gggttttggc agaaaaccag acccagagcc ggggaggtgc     240

aggagaactg atggaaaaaa atggagatgc tccaaagaag cttacccaga ctccaagtac     300

tgtgagaggc acatgcatag aggcaggaac cgttcaagaa agcctgtgga agctaattca     360

tcatcatcaa cagcaccacc agcaccacca acaacagcag cagcttccat cctttcacca     420

tctttcccat caatcaacag taaccttccc acttcaagtt cttctctctc tttttctcct     480

atggctactg aaaacttcac ccatttcgac ccctttcttt attctcattc ttctacgaga     540

cttcatggtt caggcttatc agttccatct catcatttcc tagactctgg aactggaatt     600

gattaccctc agactgataa actttacagg tatgttcatg gaacaaggga aggtgttgat     660

gaaagatctt tcttccccga agcttcagcg agtgtaagag ttgtatctga ttcttatcag     720

ccactgacaa tggtccaaag ctttggtgac aacaatggtt caaagcaggg gcagcaatgc     780

ttcgttttag gtactgatat caagtcagct aagccaatca agttagaaaa ggatgaagga     840

actcaaaaac cagtccacca atttttaggg gattggacac aagggaacaa caatggttct     900

tggcttgatc ttgcatccaa ttccagggtc caatcagata gttga                    945


<210> SEQ ID NO 30
<211> LENGTH: 314
<212> TYPE: PRT
<213> ORGANISM: Gossypium hirsutum

<400> SEQUENCE: 30

Met Ile Ser Ala Arg Asn Lys Tyr Leu Phe Thr Pro Asn Gln Trp Gln
1               5                   10                  15

Glu Leu Glu His Gln Ala Leu Ile Phe Lys Tyr Met Val Ser Gly Val
            20                  25                  30

Pro Ile Pro Pro Gln Leu Leu Tyr Ser Val Lys Thr Ser Phe Asp Ser
        35                  40                  45

Ser Leu Ala Ser His Leu Phe Pro His Gln Pro Thr Gly Trp Gly Cys
    50                  55                  60

Phe Gln Val Gly Phe Gly Arg Lys Pro Asp Pro Glu Pro Gly Arg Cys
65                  70                  75                  80
```

-continued

```
Arg Arg Thr Asp Gly Lys Lys Trp Arg Cys Ser Lys Glu Ala Tyr Pro
                85                  90                  95

Asp Ser Lys Tyr Cys Glu Arg His Met His Arg Gly Arg Asn Arg Ser
            100                 105                 110

Arg Lys Pro Val Glu Ala Asn Ser Ser Ser Ser Thr Ala Pro Pro Ala
        115                 120                 125

Pro Pro Thr Thr Ala Ala Ala Ser Ile Leu Ser Pro Ser Phe Pro Ser
    130                 135                 140

Ile Asn Ser Asn Leu Pro Thr Ser Ser Ser Ser Leu Ser Phe Ser Pro
145                 150                 155                 160

Met Ala Thr Glu Asn Phe Thr His Phe Asp Pro Phe Leu Tyr Ser His
                165                 170                 175

Ser Ser Thr Arg Leu His Gly Ser Gly Leu Ser Val Pro Ser His His
            180                 185                 190

Phe Leu Asp Ser Gly Thr Gly Ile Asp Tyr Pro Gln Thr Asp Lys Leu
        195                 200                 205

Tyr Arg Tyr Val His Gly Thr Arg Glu Gly Val Asp Glu Arg Ser Phe
    210                 215                 220

Phe Pro Glu Ala Ser Ala Ser Val Arg Val Val Ser Asp Ser Tyr Gln
225                 230                 235                 240

Pro Leu Thr Met Val Gln Ser Phe Gly Asp Asn Asn Gly Ser Lys Gln
                245                 250                 255

Gly Gln Gln Cys Phe Val Leu Gly Thr Asp Ile Lys Ser Ala Lys Pro
            260                 265                 270

Ile Lys Leu Glu Lys Asp Glu Gly Thr Gln Lys Pro Val His Gln Phe
        275                 280                 285

Leu Gly Asp Trp Thr Gln Gly Asn Asn Asn Gly Ser Trp Leu Asp Leu
    290                 295                 300

Ala Ser Asn Ser Arg Val Gln Ser Asp Ser
305                 310
```

<210> SEQ ID NO 31
<211> LENGTH: 1194
<212> TYPE: DNA
<213> ORGANISM: Artificial Sequence
<220> FEATURE:
<223> OTHER INFORMATION: cDNA of OsGRF5

<400> SEQUENCE: 31

```
atgatgatga tgagcggtcg cccgagcggc ggcgccggcg gaggtcggta cccgttcacg     60

gcgtcgcagt ggcaggagct ggagcaccag gcgctcatct acaagtacat ggcgtccggg    120

actcccatcc cctccgacct catcctcccc ctccgccgca gcttcctcct cgactccgcc    180

ctcgccacct cccccttccct cgccttccct ccccaacctt cactggggtg gggttgcttt    240

ggcatggggt ttgggcggaa ggcggaggac ccggagccag ggcgatgccg gcgtacggac    300

ggcaagaagt ggcggtgctc caaggaggcg tacccggact ccaagtactg cgagaagcac    360

atgcaccgtg gcaagaaccg ttcaagaaag cctgtggaaa tgtccttggc cacgccgccg    420

ccgccgtcct cctccgccac ctccgccgcg tcgaacacct ccgccggcgt cgccccccacc    480

accaccacca cctcctcccc ggcgccctcc tacagccgcc cggcgccgca cgacgcggcg    540

ccgtaccagg cgctctacgg cgggccctac gccgcggcca ccgcgcgcac ccccgccgcc    600

gcggcgtacc acgcgcaggt gagcccgttc cacctccagc tcgacaccac ccacccgcac    660

ccgccgccgt cctactactc catggaccac aaggagtacg cgtacgggca cgccaccaag    720
```

```
gaggtgcacg gcgagcacgc cttcttctcc gatggcaccg agagggagca ccaccacgcc    780

gccgccgggc acggccagtg gcagttcaag cagctcggca tggagcccaa gcagagcacc    840

acgcctctct tcccgggcgc cggctacggc cacaccgcgg cgtcgccgta cgccattgat    900

ctttcaaaag aggacgacga tgagaaagag aggcggcaac agcagcagca gcagcagcag    960

cagcactgct tcctcctggg cgccgacctc cgtctggaga agccggcggg ccacgaccac   1020

gcggcggcgg cgcagaaacc tctccgccac ttcttcgacg agtggccgca tgagaagaac   1080

agcaagggct cctggatggg gctcgaaggc gagacgcagc tgtccatgtc catccccatg   1140

gccgccaacg acctcccgat caccaccacc tcccgctacc acaatgatga ttaa         1194
```

```
<210> SEQ ID NO 32
<211> LENGTH: 397
<212> TYPE: PRT
<213> ORGANISM: Oryza sativa

<400> SEQUENCE: 32

Met Met Met Met Ser Gly Arg Pro Ser Gly Gly Ala Gly Gly Gly Arg
1               5                   10                  15

Tyr Pro Phe Thr Ala Ser Gln Trp Gln Glu Leu Glu His Gln Ala Leu
            20                  25                  30

Ile Tyr Lys Tyr Met Ala Ser Gly Thr Pro Ile Pro Ser Asp Leu Ile
        35                  40                  45

Leu Pro Leu Arg Arg Ser Phe Leu Leu Asp Ser Ala Leu Ala Thr Ser
    50                  55                  60

Pro Ser Leu Ala Phe Pro Pro Gln Pro Ser Leu Gly Trp Gly Cys Phe
65                  70                  75                  80

Gly Met Gly Phe Gly Arg Lys Ala Glu Asp Pro Glu Pro Gly Arg Cys
                85                  90                  95

Arg Arg Thr Asp Gly Lys Lys Trp Arg Cys Ser Lys Glu Ala Tyr Pro
            100                 105                 110

Asp Ser Lys Tyr Cys Glu Lys His Met His Arg Gly Lys Asn Arg Ser
        115                 120                 125

Arg Lys Pro Val Glu Met Ser Leu Ala Thr Pro Pro Pro Pro Ser Ser
    130                 135                 140

Ser Ala Thr Ser Ala Ala Ser Asn Thr Ser Ala Gly Val Ala Pro Thr
145                 150                 155                 160

Thr Thr Thr Thr Ser Ser Pro Ala Pro Ser Tyr Ser Arg Pro Ala Pro
                165                 170                 175

His Asp Ala Ala Pro Tyr Gln Ala Leu Tyr Gly Gly Pro Tyr Ala Ala
            180                 185                 190

Ala Thr Ala Arg Thr Pro Ala Ala Ala Ala Tyr His Ala Gln Val Ser
        195                 200                 205

Pro Phe His Leu Gln Leu Asp Thr Thr His Pro His Pro Pro Pro Ser
    210                 215                 220

Tyr Tyr Ser Met Asp His Lys Glu Tyr Ala Tyr Gly His Ala Thr Lys
225                 230                 235                 240

Glu Val His Gly Glu His Ala Phe Phe Ser Asp Gly Thr Glu Arg Glu
                245                 250                 255

His His His Ala Ala Ala Gly His Gly Gln Trp Gln Phe Lys Gln Leu
            260                 265                 270

Gly Met Glu Pro Lys Gln Ser Thr Thr Pro Leu Phe Pro Gly Ala Gly
        275                 280                 285

Tyr Gly His Thr Ala Ala Ser Pro Tyr Ala Ile Asp Leu Ser Lys Glu
```

```
    290                 295                 300

Asp Asp Asp Glu Lys Glu Arg Arg Gln Gln Gln Gln Gln Gln Gln Gln
305                 310                 315                 320

Gln His Cys Phe Leu Leu Gly Ala Asp Leu Arg Leu Glu Lys Pro Ala
                325                 330                 335

Gly His Asp His Ala Ala Ala Ala Gln Lys Pro Leu Arg His Phe Phe
            340                 345                 350

Asp Glu Trp Pro His Glu Lys Asn Ser Lys Gly Ser Trp Met Gly Leu
        355                 360                 365

Glu Gly Glu Thr Gln Leu Ser Met Ser Ile Pro Met Ala Ala Asn Asp
    370                 375                 380

Leu Pro Ile Thr Thr Thr Ser Arg Tyr His Asn Asp Asp
385                 390                 395


<210> SEQ ID NO 33
<211> LENGTH: 530
<212> TYPE: PRT
<213> ORGANISM: Arabidopsis thaliana

<400> SEQUENCE: 33

Met Asp Leu Gly Val Arg Val Ser Gly His Glu Thr Val Ser Ser Pro
1               5                   10                  15

Gly Gln Thr Glu Leu Gly Ser Gly Phe Ser Asn Lys Gln Glu Arg Ser
            20                  25                  30

Gly Phe Asp Gly Glu Asp Cys Trp Arg Ser Ser Lys Leu Ser Arg Thr
        35                  40                  45

Ser Thr Asp Gly Phe Ser Ser Ser Pro Ala Ser Ala Lys Thr Leu Ser
    50                  55                  60

Phe His Gln Gly Ile Pro Leu Leu Arg Ser Thr Thr Ile Asn Asp Pro
65                  70                  75                  80

Arg Lys Gly Gln Glu His Met Leu Ser Phe Ser Ser Ala Ser Gly Lys
                85                  90                  95

Ser Asp Val Ser Pro Tyr Leu Gln Tyr Cys Arg Asn Ser Gly Tyr Gly
            100                 105                 110

Leu Gly Gly Met Met Asn Thr Ser Asn Met His Gly Asn Leu Leu Thr
        115                 120                 125

Gly Val Lys Gly Pro Phe Ser Leu Thr Gln Trp Ala Glu Leu Glu Gln
    130                 135                 140

Gln Ala Leu Ile Tyr Lys Tyr Ile Thr Ala Asn Val Pro Val Pro Ser
145                 150                 155                 160

Ser Leu Leu Leu Ser Leu Lys Lys Ser Phe Phe Pro Tyr Gly Ser Leu
                165                 170                 175

Pro Pro Asn Ser Phe Gly Trp Gly Ser Phe His Leu Gly Phe Ser Gly
            180                 185                 190

Gly Asn Met Asp Pro Glu Pro Gly Arg Cys Arg Arg Thr Asp Gly Lys
        195                 200                 205

Lys Trp Arg Cys Ser Arg Asp Ala Val Pro Asp Gln Lys Tyr Cys Glu
    210                 215                 220

Arg His Ile Asn Arg Gly Arg His Arg Ser Arg Lys Pro Val Glu Gly
225                 230                 235                 240

Gln Asn Gly His Asn Thr Asn Ala Ala Ala Ala Ala Ser Ala Ala Ala
                245                 250                 255

Ala Ser Thr Ala Ala Ala Val Ser Lys Ala Ala Ala Gly Thr Ser Ala
            260                 265                 270
```

Val Ala Met Arg Gly Ser Asp Asn Asn Asn Ser Leu Ala Ala Ala Val
        275                 280                 285

Gly Thr Gln His His Thr Asn Asn Gln Ser Thr Asp Ser Leu Ala Asn
    290                 295                 300

Arg Val Gln Asn Ser Arg Gly Ala Ser Val Phe Pro Ala Thr Met Asn
305                 310                 315                 320

Leu Gln Ser Lys Glu Thr His Pro Lys Gln Ser Asn Asn Pro Phe Glu
                325                 330                 335

Phe Gly Leu Ile Ser Ser Asp Ser Leu Leu Asn Pro Ser His Lys Gln
            340                 345                 350

Ala Ser Tyr Ala Thr Ser Ser Lys Gly Phe Gly Ser Tyr Leu Asp Phe
        355                 360                 365

Gly Asn Gln Ala Lys His Ala Gly Asn His Asn Asn Val Asp Ser Trp
    370                 375                 380

Pro Glu Glu Leu Lys Ser Asp Trp Thr Gln Leu Ser Met Ser Ile Pro
385                 390                 395                 400

Met Ala Pro Ser Ser Pro Val Gln Asp Lys Leu Ala Leu Ser Pro Leu
                405                 410                 415

Arg Leu Ser Arg Glu Phe Asp Pro Ala Ile His Met Gly Leu Gly Val
            420                 425                 430

Asn Thr Glu Phe Leu Asp Pro Gly Lys Lys Thr Asn Asn Trp Ile Pro
        435                 440                 445

Ile Ser Trp Gly Asn Asn Asn Ser Met Gly Gly Pro Leu Gly Glu Val
    450                 455                 460

Leu Asn Ser Thr Thr Asn Ser Pro Lys Phe Gly Ser Ser Pro Thr Gly
465                 470                 475                 480

Val Leu Gln Lys Ser Thr Phe Gly Ser Leu Ser Asn Ser Ser Ser Ala
                485                 490                 495

Ser Ser Thr Ile Ile Gly Asp Asn Asn Asn Lys Asn Gly Asp Gly Lys
            500                 505                 510

Asp Pro Leu Gly Pro Thr Thr Leu Met Asn Thr Ser Ala Thr Ala Pro
        515                 520                 525

Ser Leu
    530

<210> SEQ ID NO 34
<211> LENGTH: 535
<212> TYPE: PRT
<213> ORGANISM: Arabidopsis thaliana

<400> SEQUENCE: 34

Met Asp Ile Gly Val His Val Leu Gly Ser Val Thr Ser Asn Glu Asn
1               5                   10                  15

Glu Ser Leu Gly Leu Lys Glu Leu Ile Gly Thr Lys Gln Asp Arg Ser
            20                  25                  30

Gly Phe Ile Gly Glu Asp Cys Leu Gln Arg Ser Leu Lys Leu Ala Arg
        35                  40                  45

Thr Thr Thr Arg Ala Glu Glu Glu Glu Asn Leu Ser Ser Ser Val Ala
    50                  55                  60

Ala Ala Tyr Cys Lys Thr Met Ser Phe His Gln Gly Ile Pro Leu Met
65                  70                  75                  80

Arg Ser Ala Ser Pro Leu Ser Ser Asp Ser Arg Arg Gln Glu Gln Met
                85                  90                  95

Leu Ser Phe Ser Asp Lys Pro Asp Ala Leu Asp Phe Ser Lys Tyr Val
            100                 105                 110

```
Gly Leu Asp Asn Ser Ser Asn Asn Lys Asn Ser Leu Ser Pro Phe Leu
        115                 120                 125

His Gln Ile Pro Pro Pro Ser Tyr Phe Arg Ser Ser Gly Gly Tyr Gly
    130                 135                 140

Ser Gly Gly Met Met Met Asn Met Ser Met Gln Gly Asn Phe Thr Gly
145                 150                 155                 160

Val Lys Gly Pro Phe Thr Leu Thr Gln Trp Ala Glu Leu Glu Gln Gln
                165                 170                 175

Ala Leu Ile Tyr Lys Tyr Ile Thr Ala Asn Val Pro Val Pro Ser Ser
            180                 185                 190

Leu Leu Ile Ser Ile Lys Lys Ser Phe Tyr Pro Tyr Gly Ser Leu Pro
        195                 200                 205

Pro Ser Ser Phe Gly Trp Gly Thr Phe His Leu Gly Phe Ala Gly Gly
    210                 215                 220

Asn Met Asp Pro Glu Pro Gly Arg Cys Arg Arg Thr Asp Gly Lys Lys
225                 230                 235                 240

Trp Arg Cys Ser Arg Asp Ala Val Pro Asp Gln Lys Tyr Cys Glu Arg
                245                 250                 255

His Ile Asn Arg Gly Arg His Arg Ser Arg Lys Pro Val Glu Val Gln
            260                 265                 270

Ser Gly Gln Asn Gln Thr Ala Ala Ala Ala Ser Lys Ala Val Thr Thr
        275                 280                 285

Pro Gln Gln Pro Val Val Ala Gly Asn Thr Asn Arg Ser Asn Ala Arg
    290                 295                 300

Ala Ser Ser Asn Arg Ser Leu Ala Ile Gly Ser Gln Tyr Ile Asn Pro
305                 310                 315                 320

Ser Thr Glu Ser Leu Pro Asn Asn Arg Gly Val Ser Ile Tyr Pro Ser
                325                 330                 335

Thr Val Asn Leu Gln Pro Lys Glu Ser Pro Val Ile His Gln Lys His
            340                 345                 350

Arg Asn Asn Asn Asn Pro Phe Glu Phe Gly His Ile Ser Ser Asp Ser
        355                 360                 365

Leu Leu Asn Pro Asn Thr Ala Lys Thr Tyr Gly Ser Ser Phe Leu Asp
    370                 375                 380

Phe Ser Ser Asn Gln Glu Lys His Ser Gly Asn His Asn His Asn Ser
385                 390                 395                 400

Trp Pro Glu Glu Leu Thr Ser Asp Trp Thr Gln Leu Ser Met Ser Ile
                405                 410                 415

Pro Ile Ala Ser Ser Ser Pro Ser Ser Thr His Asn Asn Asn Asn Ala
            420                 425                 430

Gln Glu Lys Thr Thr Leu Ser Pro Leu Arg Leu Ser Arg Glu Leu Asp
        435                 440                 445

Leu Ser Ile Gln Thr Asp Glu Thr Thr Ile Glu Pro Thr Val Lys Lys
    450                 455                 460

Val Asn Thr Trp Ile Pro Ile Ser Trp Gly Asn Ser Leu Gly Gly Pro
465                 470                 475                 480

Leu Gly Glu Val Leu Asn Ser Thr Thr Asn Ser Pro Thr Phe Gly Ser
                485                 490                 495

Ser Pro Thr Gly Val Leu Gln Lys Ser Thr Phe Cys Ser Leu Ser Asn
            500                 505                 510

Asn Ser Ser Val Ser Ser Pro Ile Ala Glu Asn Asn Arg His Asn Gly
        515                 520                 525
```

```
Asp Tyr Phe His Tyr Thr Thr
    530                 535


<210> SEQ ID NO 35
<211> LENGTH: 398
<212> TYPE: PRT
<213> ORGANISM: Arabidopsis thaliana

<400> SEQUENCE: 35

Met Asp Leu Gln Leu Lys Gln Trp Arg Ser Gln Gln Gln Gln Gln His
1               5                   10                  15

Gln Thr Glu Ser Glu Glu Gln Pro Ser Ala Ala Lys Ile Pro Lys His
            20                  25                  30

Val Phe Asp Gln Ile His Ser His Thr Ala Thr Ser Thr Ala Leu Pro
        35                  40                  45

Leu Phe Thr Pro Glu Pro Thr Ser Ser Lys Leu Ser Ser Leu Ser Pro
    50                  55                  60

Asp Ser Ser Ser Arg Phe Pro Lys Met Gly Ser Phe Phe Ser Trp Ala
65                  70                  75                  80

Gln Trp Gln Glu Leu Glu Leu Gln Ala Leu Ile Tyr Arg Tyr Met Leu
                85                  90                  95

Ala Gly Ala Ala Val Pro Gln Glu Leu Leu Leu Pro Ile Lys Lys Ser
            100                 105                 110

Leu Leu His Leu Ser Pro Ser Tyr Phe Leu His His Pro Leu Gln His
        115                 120                 125

Leu Pro His Tyr Gln Pro Ala Trp Tyr Leu Gly Arg Ala Ala Met Asp
    130                 135                 140

Pro Glu Pro Gly Arg Cys Arg Arg Thr Asp Gly Lys Lys Trp Arg Cys
145                 150                 155                 160

Ser Arg Asp Val Phe Ala Gly His Lys Tyr Cys Glu Arg His Met His
                165                 170                 175

Arg Gly Arg Asn Arg Ser Arg Lys Pro Val Glu Thr Pro Thr Thr Val
            180                 185                 190

Asn Ala Thr Ala Thr Ser Met Ala Ser Ser Val Ala Ala Ala Ala Thr
        195                 200                 205

Thr Thr Thr Ala Thr Thr Thr Ser Thr Phe Ala Phe Gly Gly Gly Gly
    210                 215                 220

Gly Ser Glu Glu Val Val Gly Gln Gly Gly Ser Phe Phe Phe Ser Gly
225                 230                 235                 240

Ser Ser Asn Ser Ser Ser Glu Leu Leu His Leu Ser Gln Ser Cys Ser
                245                 250                 255

Glu Met Lys Gln Glu Ser Asn Asn Met Asn Asn Lys Arg Pro Tyr Glu
            260                 265                 270

Ser His Ile Gly Phe Ser Asn Asn Arg Ser Asp Gly Gly His Ile Leu
        275                 280                 285

Arg Pro Phe Phe Asp Asp Trp Pro Arg Ser Ser Leu Gln Glu Ala Asp
    290                 295                 300

Asn Ser Ser Ser Pro Met Ser Ser Ala Thr Cys Leu Ser Ile Ser Met
305                 310                 315                 320

Pro Gly Asn Ser Ser Ser Asp Val Ser Leu Lys Leu Ser Thr Gly Asn
                325                 330                 335

Glu Glu Gly Ala Arg Ser Asn Asn Asn Gly Arg Asp Gln Gln Asn Met
            340                 345                 350

Ser Trp Trp Ser Gly Gly Gly Ser Asn His His His His Asn Met Gly
        355                 360                 365
```

```
Gly Pro Leu Ala Glu Ala Leu Arg Ser Ser Ser Ser Ser Ser Pro Thr
    370                 375                 380

Ser Val Leu His Gln Leu Gly Val Ser Thr Gln Ala Phe His
385                 390                 395


<210> SEQ ID NO 36
<211> LENGTH: 380
<212> TYPE: PRT
<213> ORGANISM: Arabidopsis thaliana

<400> SEQUENCE: 36

Met Asp Leu Gln Leu Lys Gln Trp Arg Ser Gln Gln Gln Asn Glu Ser
1               5                   10                  15

Glu Glu Gln Gly Ser Ala Ala Thr Lys Ile Ser Asn Phe Phe Phe Asp
            20                  25                  30

Gln Ile Gln Ser Gln Thr Ala Thr Ser Ala Ala Ala Ala Pro Leu Pro
        35                  40                  45

Leu Phe Val Pro Glu Pro Thr Ser Ser Ser Ser Phe Ser Cys Phe Ser
    50                  55                  60

Pro Asp Ser Ser Asn Ser Ser Ser Ser Ser Arg Phe Leu Lys Met Gly
65                  70                  75                  80

Asn Phe Phe Ser Trp Ala Gln Trp Gln Glu Leu Glu Leu Gln Ala Leu
                85                  90                  95

Ile Tyr Arg Tyr Met Leu Ala Gly Ala Ser Val Pro Gln Glu Leu Leu
            100                 105                 110

Leu Pro Ile Lys Lys Ser Leu Leu His Gln Ser Pro Met His Phe Leu
        115                 120                 125

His His Pro Leu Gln His Ser Phe Pro His His Gln Pro Ser Trp Tyr
    130                 135                 140

Trp Gly Arg Gly Ala Met Asp Pro Glu Pro Gly Arg Cys Lys Arg Thr
145                 150                 155                 160

Asp Gly Lys Lys Trp Arg Cys Ser Arg Asp Val Val Ala Gly His Lys
                165                 170                 175

Tyr Cys Asp Arg His Ile His Arg Gly Arg Asn Arg Ser Arg Lys Pro
            180                 185                 190

Val Glu Thr Ala Thr Thr Thr Ile Thr Thr Thr Ala Thr Thr Thr Ala
        195                 200                 205

Ser Ser Phe Val Leu Gly Glu Glu Leu Gly His Gly Pro Asn Asn Asn
    210                 215                 220

His Phe Phe Ser Ser Gly Ser Ser Gln Pro Leu His Leu Ser His Gln
225                 230                 235                 240

Gln Ser Cys Ser Ser Glu Met Lys Gln Glu Ser Asn Asn Asn Lys Arg
                245                 250                 255

Pro Tyr Glu Ala Asn Ser Gly Phe Ser Asn Gly Arg Ser Asp Asp Gly
            260                 265                 270

His Ile Leu Arg His Phe Phe Asp Asp Trp Pro Arg Ser Ser Asp Ser
        275                 280                 285

Thr Ser Ser Pro Met Ser Ser Ser Thr Cys His Leu Ser Ile Ser Met
    290                 295                 300

Pro Gly Asn Asn Thr Ser Ser Asp Val Ser Leu Lys Leu Ser Thr Gly
305                 310                 315                 320

Asn Glu Glu Glu Glu Glu Asn Met Arg Asn Asn Asn Asn Glu Arg Glu
                325                 330                 335

Gln Met Asn Trp Trp Ser Asn Gly Gly Asn His His Asn Asn Met Gly
```

```
            340                 345                 350

Gly Pro Leu Ala Glu Ala Leu Arg Ser Ala Ser Ser Thr Ser Ser Val
        355                 360                 365

Leu His Gln Met Gly Ile Ser Thr Gln Val Phe His
    370                 375                 380


<210> SEQ ID NO 37
<211> LENGTH: 244
<212> TYPE: PRT
<213> ORGANISM: Arabidopsis thaliana

<400> SEQUENCE: 37

Met Ala Thr Arg Ile Pro Phe Thr Glu Ser Gln Trp Glu Glu Leu Glu
1               5                   10                  15

Asn Gln Ala Leu Val Phe Lys Tyr Leu Ala Ala Asn Met Pro Val Pro
            20                  25                  30

Pro His Leu Leu Phe Leu Ile Lys Arg Pro Phe Leu Phe Ser Ser Ser
        35                  40                  45

Ser Ser Ser Ser Ser Ser Ser Ser Phe Phe Ser Pro Thr Leu Ser Pro
    50                  55                  60

His Phe Gly Trp Asn Val Tyr Glu Met Gly Met Gly Arg Lys Ile Asp
65                  70                  75                  80

Ala Glu Pro Gly Arg Cys Arg Arg Thr Asp Gly Lys Lys Trp Arg Cys
                85                  90                  95

Ser Lys Glu Ala Tyr Pro Asp Ser Lys Tyr Cys Glu Arg His Met His
            100                 105                 110

Arg Gly Lys Asn Arg Ser Ser Ser Arg Lys Pro Pro Pro Thr Gln Phe
        115                 120                 125

Thr Pro Asn Leu Phe Leu Asp Ser Ser Ser Arg Arg Arg Arg Ser Gly
    130                 135                 140

Tyr Met Asp Asp Phe Phe Ser Ile Glu Pro Ser Gly Ser Ile Lys Ser
145                 150                 155                 160

Cys Ser Gly Ser Ala Met Glu Asp Asn Asp Asp Gly Ser Cys Arg Gly
                165                 170                 175

Ile Asn Asn Glu Glu Lys Gln Pro Asp Arg His Cys Phe Ile Leu Gly
            180                 185                 190

Thr Asp Leu Arg Thr Arg Glu Arg Pro Leu Met Leu Glu Glu Lys Leu
        195                 200                 205

Lys Gln Arg Asp His Asp Asn Glu Glu Glu Gln Gly Ser Lys Arg Phe
    210                 215                 220

Tyr Arg Phe Leu Asp Glu Trp Pro Ser Ser Lys Ser Ser Val Ser Thr
225                 230                 235                 240

Ser Leu Phe Ile


<210> SEQ ID NO 38
<211> LENGTH: 365
<212> TYPE: PRT
<213> ORGANISM: Arabidopsis thaliana

<400> SEQUENCE: 38

Met Asp Phe Leu Lys Val Ser Asp Lys Thr Thr Ile Pro Tyr Arg Ser
1               5                   10                  15

Asp Ser Leu Phe Ser Leu Asn Gln Gln Gln Tyr Lys Glu Ser Ser Phe
            20                  25                  30

Gly Phe Arg Asp Met Glu Ile His Pro His Pro Thr Pro Tyr Ala Gly
        35                  40                  45
```

```
Asn Gly Leu Leu Gly Cys Tyr Tyr Tyr Tyr Pro Phe Thr Asn Ala Gln
    50                  55                  60

Leu Lys Glu Leu Glu Arg Gln Ala Met Ile Tyr Lys Tyr Met Ile Ala
65                  70                  75                  80

Ser Ile Pro Val Pro Phe Asp Leu Leu Val Ser Ser Pro Ser Ser Ala
                85                  90                  95

Ser Pro Cys Asn Asn Lys Asn Ile Ala Gly Asp Leu Glu Pro Gly Arg
            100                 105                 110

Cys Arg Arg Thr Asp Gly Lys Lys Trp Arg Cys Ala Lys Glu Val Val
        115                 120                 125

Ser Asn His Lys Tyr Cys Glu Lys His Leu His Arg Gly Arg Pro Arg
    130                 135                 140

Ser Arg Lys His Val Glu Pro Pro Tyr Ser Arg Pro Asn Asn Asn Gly
145                 150                 155                 160

Gly Ser Val Lys Asn Arg Asp Leu Lys Lys Leu Pro Gln Lys Leu Ser
                165                 170                 175

Ser Ser Ser Ile Lys Asp Lys Thr Leu Glu Pro Met Glu Val Ser Ser
            180                 185                 190

Ser Ile Ser Asn Tyr Arg Asp Ser Arg Gly Ser Glu Lys Phe Thr Val
        195                 200                 205

Leu Ala Thr Thr Glu Gln Glu Asn Lys Tyr Leu Asn Phe Ile Asp Val
    210                 215                 220

Trp Ser Asp Gly Val Arg Ser Ser Glu Lys Gln Ser Thr Thr Ser Thr
225                 230                 235                 240

Pro Val Ser Ser Ser Asn Gly Asn Leu Ser Leu Tyr Ser Leu Asp Leu
                245                 250                 255

Ser Met Gly Gly Asn Asn Leu Met Gly Gln Asp Glu Met Gly Leu Ile
            260                 265                 270

Gln Met Gly Leu Gly Val Ile Gly Ser Gly Ser Glu Asp His His Gly
        275                 280                 285

Tyr Gly Pro Tyr Gly Val Thr Ser Ser Leu Glu Glu Met Ser Ser Trp
    290                 295                 300

Leu Ala Pro Met Ser Thr Thr Pro Gly Gly Pro Leu Ala Glu Ile Leu
305                 310                 315                 320

Arg Pro Ser Thr Asn Leu Ala Ile Ser Gly Asp Ile Glu Ser Tyr Ser
                325                 330                 335

Leu Met Glu Thr Pro Thr Pro Ser Ser Ser Pro Ser Arg Val Met Lys
            340                 345                 350

Lys Met Thr Ser Ser Val Ser Asp Glu Ser Ser Gln Val
        355                 360                 365
```

<210> SEQ ID NO 39
<211> LENGTH: 493
<212> TYPE: PRT
<213> ORGANISM: Arabidopsis thaliana

<400> SEQUENCE: 39

```
Met Arg Met Leu Leu Gly Ile Pro Tyr Val Asp Lys Ser Val Leu Ser
1               5                   10                  15

Asn Ser Val Leu Glu Arg Gly Lys Gln Asp Lys Ser Lys Leu Leu Leu
            20                  25                  30

Val Asp Lys Cys His Tyr Glu Leu Asp Val Glu Glu Arg Lys Glu Asp
        35                  40                  45

Phe Val Gly Gly Phe Gly Phe Gly Val Val Glu Asn Ser His Lys Asp
```

```
    50                  55                  60

Val Met Val Leu Pro His His His Tyr Tyr Pro Ser Tyr Ser Ser Pro
65                  70                  75                  80

Ser Ser Ser Ser Leu Cys Tyr Cys Ser Ala Gly Val Ser Asp Pro Met
                85                  90                  95

Phe Ser Val Ser Ser Asn Gln Ala Tyr Thr Ser Ser His Ser Gly Met
            100                 105                 110

Phe Thr Pro Ala Gly Ser Gly Ser Ala Ala Val Thr Val Ala Asp Pro
        115                 120                 125

Phe Phe Ser Leu Ser Ser Ser Gly Glu Met Arg Arg Ser Met Asn Glu
    130                 135                 140

Asp Ala Gly Ala Ala Phe Ser Glu Ala Gln Trp His Glu Leu Glu Arg
145                 150                 155                 160

Gln Arg Asn Ile Tyr Lys Tyr Met Met Ala Ser Val Pro Val Pro Pro
                165                 170                 175

Glu Leu Leu Thr Pro Phe Pro Lys Asn His Gln Ser Asn Thr Asn Pro
            180                 185                 190

Asp Val Asp Thr Tyr Arg Ser Gly Met Phe Ser Ile Tyr Ala Asp Tyr
        195                 200                 205

Lys Asn Leu Pro Leu Ser Met Trp Met Thr Val Thr Val Ala Val Ala
    210                 215                 220

Thr Gly Gly Ser Leu Gln Leu Gly Ile Ala Ser Ser Ala Ser Asn Asn
225                 230                 235                 240

Thr Ala Asp Leu Glu Pro Trp Arg Cys Lys Arg Thr Asp Gly Lys Lys
                245                 250                 255

Trp Arg Cys Ser Arg Asn Val Ile Pro Asp Gln Lys Tyr Cys Glu Arg
            260                 265                 270

His Thr His Lys Ser Arg Pro Arg Ser Arg Lys His Val Glu Ser Ser
        275                 280                 285

His Gln Ser Ser His His Asn Asp Ile Arg Thr Ala Lys Asn Asp Thr
    290                 295                 300

Ser Gln Leu Val Arg Thr Tyr Pro Gln Phe Tyr Gly Gln Pro Ile Ser
305                 310                 315                 320

Gln Ile Pro Val Leu Ser Thr Leu Pro Ser Ala Ser Ser Pro Tyr Asp
                325                 330                 335

His His Arg Gly Leu Arg Trp Phe Thr Lys Glu Asp Asp Ala Ile Gly
            340                 345                 350

Thr Leu Asn Pro Glu Thr Gln Glu Ala Val Gln Leu Lys Val Gly Ser
        355                 360                 365

Ser Arg Glu Leu Lys Arg Gly Phe Asp Tyr Asp Leu Asn Phe Arg Gln
    370                 375                 380

Lys Glu Pro Ile Val Asp Gln Ser Phe Gly Ala Leu Gln Gly Leu Leu
385                 390                 395                 400

Ser Leu Asn Gln Thr Pro Gln His Asn Gln Glu Thr Arg Gln Phe Val
                405                 410                 415

Val Glu Gly Lys Gln Asp Glu Ala Met Gly Ser Ser Leu Thr Leu Ser
            420                 425                 430

Met Ala Gly Gly Gly Met Glu Glu Thr Glu Gly Thr Asn Gln His Gln
        435                 440                 445

Trp Val Ser His Glu Gly Pro Ser Trp Leu Tyr Ser Thr Thr Pro Gly
    450                 455                 460

Gly Pro Leu Ala Glu Ala Leu Cys Leu Gly Val Ser Asn Asn Pro Ser
465                 470                 475                 480
```

```
Ser Ser Thr Thr Thr Ser Ser Cys Ser Arg Ser Ser Ser
                485                 490


<210> SEQ ID NO 40
<211> LENGTH: 431
<212> TYPE: PRT
<213> ORGANISM: Arabidopsis thaliana

<400> SEQUENCE: 40

Met Lys Met Gln Ser Pro Lys Met Glu Gln Glu Glu Val Glu Glu Glu
1               5                   10                  15

Arg Met Arg Asn Lys Trp Pro Trp Met Lys Ala Ala Gln Leu Met Glu
            20                  25                  30

Phe Arg Met Gln Ala Leu Val Tyr Arg Tyr Ile Glu Ala Gly Leu Arg
        35                  40                  45

Val Pro His His Leu Val Val Pro Ile Trp Asn Ser Leu Ala Leu Ser
    50                  55                  60

Ser Ser Ser Asn Tyr Asn Tyr His Ser Ser Ser Leu Leu Ser Asn Lys
65                  70                  75                  80

Gly Val Thr His Ile Asp Thr Leu Glu Thr Glu Pro Thr Arg Cys Arg
                85                  90                  95

Arg Thr Asp Gly Lys Lys Trp Arg Cys Ser Asn Thr Val Leu Leu Phe
            100                 105                 110

Glu Lys Tyr Cys Glu Arg His Met His Arg Gly Arg Lys Arg Ser Arg
        115                 120                 125

Lys Leu Val Glu Ser Ser Ser Glu Val Ala Ser Ser Ser Thr Lys Tyr
    130                 135                 140

Asp Asn Thr Tyr Gly Leu Asp Arg Tyr Asn Glu Ser Gln Ser His Leu
145                 150                 155                 160

His Gly Thr Ile Ser Gly Ser Ser Asn Ala Gln Val Val Thr Ile Ala
                165                 170                 175

Ser Leu Pro Ser Ala Arg Ser Cys Glu Asn Val Ile Arg Pro Ser Leu
            180                 185                 190

Val Ile Ser Glu Phe Thr Asn Lys Ser Val Ser His Gly Arg Lys Asn
        195                 200                 205

Met Glu Met Ser Tyr Asp Asp Phe Ile Asn Glu Lys Glu Ala Ser Met
    210                 215                 220

Cys Val Gly Val Val Pro Leu Gln Gly Asp Glu Ser Lys Pro Ser Val
225                 230                 235                 240

Gln Lys Phe Phe Pro Glu Val Ser Asp Lys Cys Leu Glu Ala Ala Lys
                245                 250                 255

Phe Ser Ser Asn Arg Lys Asn Asp Ile Ile Ala Arg Ser Arg Glu Trp
            260                 265                 270

Lys Asn Met Asn Val Asn Gly Gly Leu Phe His Gly Ile His Phe Ser
        275                 280                 285

Pro Asp Thr Val Leu Gln Glu Arg Gly Cys Phe Arg Leu Gln Gly Val
    290                 295                 300

Glu Thr Asp Asn Glu Pro Gly Arg Cys Arg Arg Thr Asp Gly Lys Lys
305                 310                 315                 320

Trp Arg Cys Ser Lys Asp Val Leu Ser Gly Gln Lys Tyr Cys Asp Lys
                325                 330                 335

His Met His Arg Gly Met Lys Lys Lys His Pro Val Asp Thr Thr Asn
            340                 345                 350

Ser His Glu Asn Ala Gly Phe Ser Pro Leu Thr Val Glu Thr Ala Val
```

355 360 365

Arg Ser Val Val Pro Cys Lys Asp Gly Asp Asp Gln Lys His Ser Val
370 375 380

Ser Val Met Gly Ile Thr Leu Pro Arg Val Ser Asp Glu Lys Ser Thr
385 390 395 400

Ser Ser Cys Ser Thr Asp Thr Thr Ile Thr Asp Thr Ala Leu Arg Gly
405 410 415

Glu Asp Asp Asp Glu Glu Tyr Leu Ser Leu Phe Ser Pro Gly Val
420 425 430

<210> SEQ ID NO 41
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 41

Asp Pro Glu Pro Gly Arg Cys Arg Arg Thr Asp Gly Lys Lys Trp Arg
1 5 10 15

Cys Ser Arg Glu Ala Tyr Pro Asp Ser Lys Tyr Cys Glu Lys His Met
20 25 30

His Arg Gly Arg Asn Arg
35

<210> SEQ ID NO 42
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 42

Asp Pro Glu Pro Gly Arg Cys Arg Arg Thr Asp Gly Lys Lys Trp Arg
1 5 10 15

Cys Ala Arg Glu Ala Tyr Pro Asp Ser Lys Tyr Cys Glu Lys His Met
20 25 30

His Arg Gly Arg Asn Arg
35

<210> SEQ ID NO 43
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 43

Asp Pro Glu Pro Gly Arg Cys Arg Arg Thr Asp Gly Lys Lys Trp Arg
1 5 10 15

Cys Ser Lys Glu Ala Tyr Pro Asp Ser Lys Tyr Cys Glu Lys His Met
20 25 30

His Arg Gly Arg Asn Arg
35

<210> SEQ ID NO 44
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 44

Asp Pro Glu Pro Gly Arg Cys Arg Arg Thr Asp Gly Lys Lys Trp Arg
1 5 10 15

Cys Ala Lys Glu Ala Tyr Pro Asp Ser Lys Tyr Cys Glu Lys His Met
20 25 30

His Arg Gly Arg Asn Arg
35

<210> SEQ ID NO 45
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 45

Asp Pro Glu Pro Gly Arg Cys Arg Arg Thr Asp Gly Lys Lys Trp Arg
1 5 10 15

Cys Ser Arg Asp Ala Tyr Pro Asp Ser Lys Tyr Cys Glu Lys His Met
20 25 30

His Arg Gly Arg Asn Arg
35

<210> SEQ ID NO 46
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 46

Asp Pro Glu Pro Gly Arg Cys Arg Arg Thr Asp Gly Lys Lys Trp Arg
1 5 10 15

Cys Ala Arg Asp Ala Tyr Pro Asp Ser Lys Tyr Cys Glu Lys His Met
20 25 30

His Arg Gly Arg Asn Arg
35

<210> SEQ ID NO 47
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 47

Asp Pro Glu Pro Gly Arg Cys Arg Arg Thr Asp Gly Lys Lys Trp Arg
1 5 10 15

Cys Ser Lys Asp Ala Tyr Pro Asp Ser Lys Tyr Cys Glu Lys His Met
20 25 30

His Arg Gly Arg Asn Arg
35

<210> SEQ ID NO 48
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 48

Asp Pro Glu Pro Gly Arg Cys Arg Arg Thr Asp Gly Lys Lys Trp Arg

```
1               5                   10                  15

Cys Ala Lys Asp Ala Tyr Pro Asp Ser Lys Tyr Cys Glu Lys His Met
            20                  25                  30

His Arg Gly Arg Asn Arg
        35


<210> SEQ ID NO 49
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 49

Asp Pro Glu Pro Gly Arg Cys Arg Arg Thr Asp Gly Lys Lys Trp Arg
1               5                   10                  15

Cys Ser Arg Glu Ala His Pro Asp Ser Lys Tyr Cys Glu Lys His Met
            20                  25                  30

His Arg Gly Arg Asn Arg
        35


<210> SEQ ID NO 50
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 50

Asp Pro Glu Pro Gly Arg Cys Arg Arg Thr Asp Gly Lys Lys Trp Arg
1               5                   10                  15

Cys Ala Arg Glu Ala His Pro Asp Ser Lys Tyr Cys Glu Lys His Met
            20                  25                  30

His Arg Gly Arg Asn Arg
        35


<210> SEQ ID NO 51
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 51

Asp Pro Glu Pro Gly Arg Cys Arg Arg Thr Asp Gly Lys Lys Trp Arg
1               5                   10                  15

Cys Ser Lys Glu Ala His Pro Asp Ser Lys Tyr Cys Glu Lys His Met
            20                  25                  30

His Arg Gly Arg Asn Arg
        35


<210> SEQ ID NO 52
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 52

Asp Pro Glu Pro Gly Arg Cys Arg Arg Thr Asp Gly Lys Lys Trp Arg
1               5                   10                  15

Cys Ala Lys Glu Ala His Pro Asp Ser Lys Tyr Cys Glu Lys His Met
```

```
            20                  25                  30

His Arg Gly Arg Asn Arg
        35


<210> SEQ ID NO 53
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 53

Asp Pro Glu Pro Gly Arg Cys Arg Arg Thr Asp Gly Lys Lys Trp Arg
1               5                   10                  15

Cys Ser Arg Asp Ala His Pro Asp Ser Lys Tyr Cys Glu Lys His Met
            20                  25                  30

His Arg Gly Arg Asn Arg
        35


<210> SEQ ID NO 54
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 54

Asp Pro Glu Pro Gly Arg Cys Arg Arg Thr Asp Gly Lys Lys Trp Arg
1               5                   10                  15

Cys Ala Arg Asp Ala His Pro Asp Ser Lys Tyr Cys Glu Lys His Met
            20                  25                  30

His Arg Gly Arg Asn Arg
        35


<210> SEQ ID NO 55
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 55

Asp Pro Glu Pro Gly Arg Cys Arg Arg Thr Asp Gly Lys Lys Trp Arg
1               5                   10                  15

Cys Ser Lys Asp Ala His Pro Asp Ser Lys Tyr Cys Glu Lys His Met
            20                  25                  30

His Arg Gly Arg Asn Arg
        35


<210> SEQ ID NO 56
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 56

Asp Pro Glu Pro Gly Arg Cys Arg Arg Thr Asp Gly Lys Lys Trp Arg
1               5                   10                  15

Cys Ala Lys Asp Ala His Pro Asp Ser Lys Tyr Cys Glu Lys His Met
            20                  25                  30

His Arg Gly Arg Asn Arg
```

35

<210> SEQ ID NO 57
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 57

Asp Pro Glu Pro Gly Arg Cys Arg Arg Thr Asp Gly Lys Lys Trp Arg
1 5 10 15

Cys Ser Arg Glu Ala Tyr Pro Asp Ser Lys Tyr Cys Glu Arg His Met
20 25 30

His Arg Gly Arg Asn Arg
35

<210> SEQ ID NO 58
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 58

Asp Pro Glu Pro Gly Arg Cys Arg Arg Thr Asp Gly Lys Lys Trp Arg
1 5 10 15

Cys Ala Arg Glu Ala Tyr Pro Asp Ser Lys Tyr Cys Glu Arg His Met
20 25 30

His Arg Gly Arg Asn Arg
35

<210> SEQ ID NO 59
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 59

Asp Pro Glu Pro Gly Arg Cys Arg Arg Thr Asp Gly Lys Lys Trp Arg
1 5 10 15

Cys Ser Lys Glu Ala Tyr Pro Asp Ser Lys Tyr Cys Glu Arg His Met
20 25 30

His Arg Gly Arg Asn Arg
35

<210> SEQ ID NO 60
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 60

Asp Pro Glu Pro Gly Arg Cys Arg Arg Thr Asp Gly Lys Lys Trp Arg
1 5 10 15

Cys Ala Lys Glu Ala Tyr Pro Asp Ser Lys Tyr Cys Glu Arg His Met
20 25 30

His Arg Gly Arg Asn Arg
35

<210> SEQ ID NO 61
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 61

Asp Pro Glu Pro Gly Arg Cys Arg Arg Thr Asp Gly Lys Lys Trp Arg
1 5 10 15

Cys Ser Arg Asp Ala Tyr Pro Asp Ser Lys Tyr Cys Glu Arg His Met
20 25 30

His Arg Gly Arg Asn Arg
35

<210> SEQ ID NO 62
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 62

Asp Pro Glu Pro Gly Arg Cys Arg Arg Thr Asp Gly Lys Lys Trp Arg
1 5 10 15

Cys Ala Arg Asp Ala Tyr Pro Asp Ser Lys Tyr Cys Glu Arg His Met
20 25 30

His Arg Gly Arg Asn Arg
35

<210> SEQ ID NO 63
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 63

Asp Pro Glu Pro Gly Arg Cys Arg Arg Thr Asp Gly Lys Lys Trp Arg
1 5 10 15

Cys Ser Lys Asp Ala Tyr Pro Asp Ser Lys Tyr Cys Glu Arg His Met
20 25 30

His Arg Gly Arg Asn Arg
35

<210> SEQ ID NO 64
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 64

Asp Pro Glu Pro Gly Arg Cys Arg Arg Thr Asp Gly Lys Lys Trp Arg
1 5 10 15

Cys Ala Lys Asp Ala Tyr Pro Asp Ser Lys Tyr Cys Glu Arg His Met
20 25 30

His Arg Gly Arg Asn Arg
35

<210> SEQ ID NO 65
<211> LENGTH: 38
<212> TYPE: PRT

<213> ORGANISM: Artificial Sequence
<220> FEATURE:
<223> OTHER INFORMATION: variant of the indicator motif

<400> SEQUENCE: 65

Asp Pro Glu Pro Gly Arg Cys Arg Arg Thr Asp Gly Lys Lys Trp Arg
1 5 10 15

Cys Ser Arg Glu Ala His Pro Asp Ser Lys Tyr Cys Glu Arg His Met
20 25 30

His Arg Gly Arg Asn Arg
35

<210> SEQ ID NO 66
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 66

Asp Pro Glu Pro Gly Arg Cys Arg Arg Thr Asp Gly Lys Lys Trp Arg
1 5 10 15

Cys Ala Arg Glu Ala His Pro Asp Ser Lys Tyr Cys Glu Arg His Met
20 25 30

His Arg Gly Arg Asn Arg
35

<210> SEQ ID NO 67
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 67

Asp Pro Glu Pro Gly Arg Cys Arg Arg Thr Asp Gly Lys Lys Trp Arg
1 5 10 15

Cys Ser Lys Glu Ala His Pro Asp Ser Lys Tyr Cys Glu Arg His Met
20 25 30

His Arg Gly Arg Asn Arg
35

<210> SEQ ID NO 68
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 68

Asp Pro Glu Pro Gly Arg Cys Arg Arg Thr Asp Gly Lys Lys Trp Arg
1 5 10 15

Cys Ala Lys Glu Ala His Pro Asp Ser Lys Tyr Cys Glu Arg His Met
20 25 30

His Arg Gly Arg Asn Arg
35

<210> SEQ ID NO 69
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 69

Asp Pro Glu Pro Gly Arg Cys Arg Arg Thr Asp Gly Lys Lys Trp Arg
1               5                   10                  15

Cys Ser Arg Asp Ala His Pro Asp Ser Lys Tyr Cys Glu Arg His Met
            20                  25                  30

His Arg Gly Arg Asn Arg
        35

<210> SEQ ID NO 70
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 70

Asp Pro Glu Pro Gly Arg Cys Arg Arg Thr Asp Gly Lys Lys Trp Arg
1               5                   10                  15

Cys Ala Arg Asp Ala His Pro Asp Ser Lys Tyr Cys Glu Arg His Met
            20                  25                  30

His Arg Gly Arg Asn Arg
        35

<210> SEQ ID NO 71
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 71

Asp Pro Glu Pro Gly Arg Cys Arg Arg Thr Asp Gly Lys Lys Trp Arg
1               5                   10                  15

Cys Ser Lys Asp Ala His Pro Asp Ser Lys Tyr Cys Glu Arg His Met
            20                  25                  30

His Arg Gly Arg Asn Arg
        35

<210> SEQ ID NO 72
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 72

Asp Pro Glu Pro Gly Arg Cys Arg Arg Thr Asp Gly Lys Lys Trp Arg
1               5                   10                  15

Cys Ala Lys Asp Ala His Pro Asp Ser Lys Tyr Cys Glu Arg His Met
            20                  25                  30

His Arg Gly Arg Asn Arg
        35

<210> SEQ ID NO 73
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 73

```
Asp Pro Glu Pro Gly Arg Cys Arg Arg Thr Asp Gly Lys Lys Trp Arg
1               5                   10                  15

Cys Ser Arg Glu Ala Tyr Pro Asp Ser Lys Tyr Cys Glu Lys His Met
            20                  25                  30

His Arg Gly Lys Asn Arg
        35


<210> SEQ ID NO 74
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 74

Asp Pro Glu Pro Gly Arg Cys Arg Arg Thr Asp Gly Lys Lys Trp Arg
1               5                   10                  15

Cys Ala Arg Glu Ala Tyr Pro Asp Ser Lys Tyr Cys Glu Lys His Met
            20                  25                  30

His Arg Gly Lys Asn Arg
        35


<210> SEQ ID NO 75
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 75

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Lys His Met
            20                  25                  30

His Arg Gly Lys Asn Arg
        35


<210> SEQ ID NO 76
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 76

Asp Pro Glu Pro Gly Arg Cys Arg Arg Thr Asp Gly Lys Lys Trp Arg
1               5                   10                  15

Cys Ala Lys Glu Ala Tyr Pro Asp Ser Lys Tyr Cys Glu Lys His Met
            20                  25                  30

His Arg Gly Lys Asn Arg
        35


<210> SEQ ID NO 77
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 77

Asp Pro Glu Pro Gly Arg Cys Arg Arg Thr Asp Gly Lys Lys Trp Arg
1               5                   10                  15
```

```
Cys Ser Arg Asp Ala Tyr Pro Asp Ser Lys Tyr Cys Glu Lys His Met
            20                  25                  30

His Arg Gly Lys Asn Arg
        35


<210> SEQ ID NO 78
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 78

Asp Pro Glu Pro Gly Arg Cys Arg Arg Thr Asp Gly Lys Lys Trp Arg
1               5                   10                  15

Cys Ala Arg Asp Ala Tyr Pro Asp Ser Lys Tyr Cys Glu Lys His Met
            20                  25                  30

His Arg Gly Lys Asn Arg
        35


<210> SEQ ID NO 79
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 79

Asp Pro Glu Pro Gly Arg Cys Arg Arg Thr Asp Gly Lys Lys Trp Arg
1               5                   10                  15

Cys Ser Lys Asp Ala Tyr Pro Asp Ser Lys Tyr Cys Glu Lys His Met
            20                  25                  30

His Arg Gly Lys Asn Arg
        35


<210> SEQ ID NO 80
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 80

Asp Pro Glu Pro Gly Arg Cys Arg Arg Thr Asp Gly Lys Lys Trp Arg
1               5                   10                  15

Cys Ala Lys Asp Ala Tyr Pro Asp Ser Lys Tyr Cys Glu Lys His Met
            20                  25                  30

His Arg Gly Lys Asn Arg
        35


<210> SEQ ID NO 81
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 81

Asp Pro Glu Pro Gly Arg Cys Arg Arg Thr Asp Gly Lys Lys Trp Arg
1               5                   10                  15

Cys Ser Arg Glu Ala His Pro Asp Ser Lys Tyr Cys Glu Lys His Met
            20                  25                  30
```

His Arg Gly Lys Asn Arg
35

<210> SEQ ID NO 82
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 82

Asp Pro Glu Pro Gly Arg Cys Arg Arg Thr Asp Gly Lys Lys Trp Arg
1 5 10 15

Cys Ala Arg Glu Ala His Pro Asp Ser Lys Tyr Cys Glu Lys His Met
20 25 30

His Arg Gly Lys Asn Arg
35

<210> SEQ ID NO 83
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 83

Asp Pro Glu Pro Gly Arg Cys Arg Arg Thr Asp Gly Lys Lys Trp Arg
1 5 10 15

Cys Ser Lys Glu Ala His Pro Asp Ser Lys Tyr Cys Glu Lys His Met
20 25 30

His Arg Gly Lys Asn Arg
35

<210> SEQ ID NO 84
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 84

Asp Pro Glu Pro Gly Arg Cys Arg Arg Thr Asp Gly Lys Lys Trp Arg
1 5 10 15

Cys Ala Lys Glu Ala His Pro Asp Ser Lys Tyr Cys Glu Lys His Met
20 25 30

His Arg Gly Lys Asn Arg
35

<210> SEQ ID NO 85
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 85

Asp Pro Glu Pro Gly Arg Cys Arg Arg Thr Asp Gly Lys Lys Trp Arg
1 5 10 15

Cys Ser Arg Asp Ala His Pro Asp Ser Lys Tyr Cys Glu Lys His Met
20 25 30

His Arg Gly Lys Asn Arg
35

```
<210> SEQ ID NO 86
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 86

Asp Pro Glu Pro Gly Arg Cys Arg Arg Thr Asp Gly Lys Lys Trp Arg
1               5                   10                  15

Cys Ala Arg Asp Ala His Pro Asp Ser Lys Tyr Cys Glu Lys His Met
            20                  25                  30

His Arg Gly Lys Asn Arg
        35


<210> SEQ ID NO 87
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 87

Asp Pro Glu Pro Gly Arg Cys Arg Arg Thr Asp Gly Lys Lys Trp Arg
1               5                   10                  15

Cys Ser Lys Asp Ala His Pro Asp Ser Lys Tyr Cys Glu Lys His Met
            20                  25                  30

His Arg Gly Lys Asn Arg
        35


<210> SEQ ID NO 88
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 88

Asp Pro Glu Pro Gly Arg Cys Arg Arg Thr Asp Gly Lys Lys Trp Arg
1               5                   10                  15

Cys Ala Lys Asp Ala His Pro Asp Ser Lys Tyr Cys Glu Lys His Met
            20                  25                  30

His Arg Gly Lys Asn Arg
        35


<210> SEQ ID NO 89
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 89

Asp Pro Glu Pro Gly Arg Cys Arg Arg Thr Asp Gly Lys Lys Trp Arg
1               5                   10                  15

Cys Ser Arg Glu Ala Tyr Pro Asp Ser Lys Tyr Cys Glu Arg His Met
            20                  25                  30

His Arg Gly Lys Asn Arg
        35


<210> SEQ ID NO 90
<211> LENGTH: 38
```

<212> TYPE: PRT
<213> ORGANISM: Artificial Sequence
<220> FEATURE:
<223> OTHER INFORMATION: variant of the indicator motif

<400> SEQUENCE: 90

Asp Pro Glu Pro Gly Arg Cys Arg Arg Thr Asp Gly Lys Lys Trp Arg
1               5                   10                  15

Cys Ala Arg Glu Ala Tyr Pro Asp Ser Lys Tyr Cys Glu Arg His Met
            20                  25                  30

His Arg Gly Lys Asn Arg
        35

<210> SEQ ID NO 91
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 91

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Arg His Met
            20                  25                  30

His Arg Gly Lys Asn Arg
        35

<210> SEQ ID NO 92
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 92

Asp Pro Glu Pro Gly Arg Cys Arg Arg Thr Asp Gly Lys Lys Trp Arg
1               5                   10                  15

Cys Ala Lys Glu Ala Tyr Pro Asp Ser Lys Tyr Cys Glu Arg His Met
            20                  25                  30

His Arg Gly Lys Asn Arg
        35

<210> SEQ ID NO 93
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 93

Asp Pro Glu Pro Gly Arg Cys Arg Arg Thr Asp Gly Lys Lys Trp Arg
1               5                   10                  15

Cys Ser Arg Asp Ala Tyr Pro Asp Ser Lys Tyr Cys Glu Arg His Met
            20                  25                  30

His Arg Gly Lys Asn Arg
        35

<210> SEQ ID NO 94
<211> LENGTH: 38
<212> TYPE: PRT
<213> ORGANISM: Artificial Sequence
<220> FEATURE:

<223> OTHER INFORMATION: variant of the indicator motif

<400> SEQUENCE: 94

Asp Pro Glu Pro Gly Arg Cys Arg Arg Thr Asp Gly Lys Lys Trp Arg
1 5 10 15

Cys Ala Arg Asp Ala Tyr Pro Asp Ser Lys Tyr Cys Glu Arg His Met
20 25 30

His Arg Gly Lys Asn Arg
35

<210> SEQ ID NO 95
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 95

Asp Pro Glu Pro Gly Arg Cys Arg Arg Thr Asp Gly Lys Lys Trp Arg
1 5 10 15

Cys Ser Lys Asp Ala Tyr Pro Asp Ser Lys Tyr Cys Glu Arg His Met
20 25 30

His Arg Gly Lys Asn Arg
35

<210> SEQ ID NO 96
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 96

Asp Pro Glu Pro Gly Arg Cys Arg Arg Thr Asp Gly Lys Lys Trp Arg
1 5 10 15

Cys Ala Lys Asp Ala Tyr Pro Asp Ser Lys Tyr Cys Glu Arg His Met
20 25 30

His Arg Gly Lys Asn Arg
35

<210> SEQ ID NO 97
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 97

Asp Pro Glu Pro Gly Arg Cys Arg Arg Thr Asp Gly Lys Lys Trp Arg
1 5 10 15

Cys Ser Arg Glu Ala His Pro Asp Ser Lys Tyr Cys Glu Arg His Met
20 25 30

His Arg Gly Lys Asn Arg
35

<210> SEQ ID NO 98
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 98

```
Asp Pro Glu Pro Gly Arg Cys Arg Arg Thr Asp Gly Lys Lys Trp Arg
1               5                   10                  15

Cys Ala Arg Glu Ala His Pro Asp Ser Lys Tyr Cys Glu Arg His Met
            20                  25                  30

His Arg Gly Lys Asn Arg
        35


<210> SEQ ID NO 99
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 99

Asp Pro Glu Pro Gly Arg Cys Arg Arg Thr Asp Gly Lys Lys Trp Arg
1               5                   10                  15

Cys Ser Lys Glu Ala His Pro Asp Ser Lys Tyr Cys Glu Arg His Met
            20                  25                  30

His Arg Gly Lys Asn Arg
        35


<210> SEQ ID NO 100
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 100

Asp Pro Glu Pro Gly Arg Cys Arg Arg Thr Asp Gly Lys Lys Trp Arg
1               5                   10                  15

Cys Ala Lys Glu Ala His Pro Asp Ser Lys Tyr Cys Glu Arg His Met
            20                  25                  30

His Arg Gly Lys Asn Arg
        35


<210> SEQ ID NO 101
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 101

Asp Pro Glu Pro Gly Arg Cys Arg Arg Thr Asp Gly Lys Lys Trp Arg
1               5                   10                  15

Cys Ser Arg Asp Ala His Pro Asp Ser Lys Tyr Cys Glu Arg His Met
            20                  25                  30

His Arg Gly Lys Asn Arg
        35


<210> SEQ ID NO 102
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 102

Asp Pro Glu Pro Gly Arg Cys Arg Arg Thr Asp Gly Lys Lys Trp Arg
1               5                   10                  15
```

Cys Ala Arg Asp Ala His Pro Asp Ser Lys Tyr Cys Glu Arg His Met
20 25 30

His Arg Gly Lys Asn Arg
35

<210> SEQ ID NO 103
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 103

Asp Pro Glu Pro Gly Arg Cys Arg Arg Thr Asp Gly Lys Lys Trp Arg
1 5 10 15

Cys Ser Lys Asp Ala His Pro Asp Ser Lys Tyr Cys Glu Arg His Met
20 25 30

His Arg Gly Lys Asn Arg
35

<210> SEQ ID NO 104
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 104

Asp Pro Glu Pro Gly Arg Cys Arg Arg Thr Asp Gly Lys Lys Trp Arg
1 5 10 15

Cys Ala Lys Asp Ala His Pro Asp Ser Lys Tyr Cys Glu Arg His Met
20 25 30

His Arg Gly Lys Asn Arg
35

<210> SEQ ID NO 105
<211> LENGTH: 1080
<212> TYPE: DNA
<213> ORGANISM: Artificial Sequence
<220> FEATURE:
<223> OTHER INFORMATION: cDNA of GmGRF5

<400> SEQUENCE: 105
atgatgagtg caagtgcagg tgcaagaaat aggtctccgt tcacacaaat tcagtggcaa 60
gagcttgagc aacaagctct tgtttttaag tacatggtta caggaacacc tatcccacca 120
gatctcatct actctattaa aagaagtcta gacacttcaa tttcttcaag gctcttccca 180
catcatccaa ttgggtgggg atgttttgaa atgggatttg gcagaaaagt agacccagag 240
ccagggaggt gcagaagaac agatggcaag aaatggagat gttcaaagga ggcatatcca 300
gactcaaagt actgtgaaag acacatgcac agaggcagaa accgttcaag aaagcctgtg 360
gaagtttctt cagcaacaag caccgccaca aacacctccc aaacaatccc atcatcttat 420
accagaaacc tttccttgac caataacagt aaccccaaca taacaccacc accaccaccc 480
tcttctttcc ctttctctca tttgccctct tctatgccta ttgatcagtc ccaacccttt 540
tcccaatcct accaaaactc ttctctcaat cccttcttct actcccaatc aacctcctct 600
agacccccag atgctgattt tccaccccaa gatgccacca cccaccacct attcatggac 660
tctgctggct cttattctca tgatgaaaag aattataggc atgttcatgg aataagggaa 720

```
gatgtggatg agagagcttt cttcccagaa gcatcaggat cagctaggag ctatacagac    780

tcgtaccaac aactatcaat gagctcctac aagtcctatt caaactccaa ctttcagaac    840

attaataatg atgccaccac caacccaaga cagcaagagc agcaactaca acaacaacaa    900

cactgttttg ttttagggac agacttcaaa tcaacaaggc caagcaaaga gaaagaagct    960

gagacaacaa caggtcagag accccttcac cgtttctttg gggagtggcc accaaagaac   1020

acaacaacag attcctggct agatcttgct tccaactcca gaatccaaac cgatgaatga   1080


<210> SEQ ID NO 106
<211> LENGTH: 359
<212> TYPE: PRT
<213> ORGANISM: Glycine max

<400> SEQUENCE: 106

Met Met Ser Ala Ser Ala Gly Ala Arg Asn Arg Ser Pro Phe Thr Gln
1               5                   10                  15

Ile Gln Trp Gln Glu Leu Glu Gln Gln Ala Leu Val Phe Lys Tyr Met
            20                  25                  30

Val Thr Gly Thr Pro Ile Pro Pro Asp Leu Ile Tyr Ser Ile Lys Arg
        35                  40                  45

Ser Leu Asp Thr Ser Ile Ser Ser Arg Leu Phe Pro His His Pro Ile
    50                  55                  60

Gly Trp Gly Cys Phe Glu Met Gly Phe Gly Arg Lys Val Asp Pro Glu
65                  70                  75                  80

Pro Gly Arg Cys Arg Arg Thr Asp Gly Lys Lys Trp Arg Cys Ser Lys
                85                  90                  95

Glu Ala Tyr Pro Asp Ser Lys Tyr Cys Glu Arg His Met His Arg Gly
            100                 105                 110

Arg Asn Arg Ser Arg Lys Pro Val Glu Val Ser Ser Ala Thr Ser Thr
        115                 120                 125

Ala Thr Asn Thr Ser Gln Thr Ile Pro Ser Ser Tyr Thr Arg Asn Leu
    130                 135                 140

Ser Leu Thr Asn Asn Ser Asn Pro Asn Ile Thr Pro Pro Pro Pro Pro
145                 150                 155                 160

Ser Ser Phe Pro Phe Ser His Leu Pro Ser Ser Met Pro Ile Asp Gln
                165                 170                 175

Ser Gln Pro Phe Ser Gln Ser Tyr Gln Asn Ser Ser Leu Asn Pro Phe
            180                 185                 190

Phe Tyr Ser Gln Ser Thr Ser Ser Arg Pro Pro Asp Ala Asp Phe Pro
        195                 200                 205

Pro Gln Asp Ala Thr Thr His His Leu Phe Met Asp Ser Ala Gly Ser
    210                 215                 220

Tyr Ser His Asp Glu Lys Asn Tyr Arg His Val His Gly Ile Arg Glu
225                 230                 235                 240

Asp Val Asp Glu Arg Ala Phe Phe Pro Glu Ala Ser Gly Ser Ala Arg
                245                 250                 255

Ser Tyr Thr Asp Ser Tyr Gln Gln Leu Ser Met Ser Ser Tyr Lys Ser
            260                 265                 270

Tyr Ser Asn Ser Asn Phe Gln Asn Ile Asn Asn Asp Ala Thr Thr Asn
        275                 280                 285

Pro Arg Gln Gln Glu Gln Gln Leu Gln Gln Gln Gln His Cys Phe Val
    290                 295                 300

Leu Gly Thr Asp Phe Lys Ser Thr Arg Pro Ser Lys Glu Lys Glu Ala
305                 310                 315                 320
```

Glu Thr Thr Thr Gly Gln Arg Pro Leu His Arg Phe Phe Gly Glu Trp
325 330 335

Pro Pro Lys Asn Thr Thr Thr Asp Ser Trp Leu Asp Leu Ala Ser Asn
340 345 350

Ser Arg Ile Gln Thr Asp Glu
355

<210> SEQ ID NO 107
<211> LENGTH: 1173
<212> TYPE: DNA
<213> ORGANISM: Artificial Sequence
<220> FEATURE:
<223> OTHER INFORMATION: cDNA of BnGRF5

<400> SEQUENCE: 107
atgatgagtc taagtggaaa tggtgggaga acaatagaga ggcctccatt tacaccaaca 60
caatggcaag aactggagaa tcaagcccta atttacaagt acatggtctc aggagttcct 120
gtcccacctg agctcatctt ctccattaga agaagcttgg actcttcctt ggtctctaga 180
ctcctccctc accaatccat tgggtgggga tgctatcaga tggggtttgg tagaaaacca 240
gatccagaac caggaaggtg cagaagaaca gatggtaaga aatggagatg ctcaagagaa 300
gcatacccag attcaaagta ctgtgaaaaa cacatgcaca gaggaaggaa ccgtgccaga 360
aaatctattg atcagaatca gacaactgct cctttaacat caccatctct ctctttcccc 420
aacaacaaca acccaagccc taccttgtct tcttcctcct ctacttattc agcttcttct 480
tcatctcctt ccattgatgc ttacagtaat atcaataggc ttggtgttgg taatagtaac 540
agtagaggtt acttcaacaa ccattccctt gactatcctt atcctttgtc ctcacctaaa 600
cagcaacaac aacaacagac tcttcatcat gcttctgctt tgtctcttca ccaaaacgca 660
tctactgctt ctcagttcaa tgccttagct tctgcaactg accataaaga cttcagatac 720
tttcaaggga ttggggagag agttggagtt ggagctgggg agaggacttt ttttccagaa 780
gcttctagaa gctttcaaga ttctccatac catcaccaac aaccgttagc tacagtaatg 840
aatgacccgt tccactctgg tactgatcat aaggttgatc atcagcatca cacatactca 900
tccgtatcat catcatctca gcatgatcaa gatcatcatc gacaacaaca gcagcaatgt 960
tttgttatgg gcgctgacat gttcaacaaa cccacaagaa ctgtcttcgc aaactcatct 1020
agacaagatc atcaagaaga ggaggagaaa gattcatcag aaacaaagaa gtctctacat 1080
catttctttg gtgaggactg ggcacagaac aaaaacagtt cagattcttg gcttgacctt 1140
tcttcccatt caagactgga cactggtagt tga 1173

<210> SEQ ID NO 108
<211> LENGTH: 390
<212> TYPE: PRT
<213> ORGANISM: Brassica napus

<400> SEQUENCE: 108

Met Met Ser Leu Ser Gly Asn Gly Gly Arg Thr Ile Glu Arg Pro Pro
1 5 10 15

Phe Thr Pro Thr Gln Trp Gln Glu Leu Glu Asn Gln Ala Leu Ile Tyr
20 25 30

Lys Tyr Met Val Ser Gly Val Pro Val Pro Pro Glu Leu Ile Phe Ser
35 40 45

Ile Arg Arg Ser Leu Asp Ser Ser Leu Val Ser Arg Leu Leu Pro His
50 55 60

```
Gln Ser Ile Gly Trp Gly Cys Tyr Gln Met Gly Phe Gly Arg Lys Pro
65                  70                  75                  80

Asp Pro Glu Pro Gly Arg Cys Arg Arg Thr Asp Gly Lys Lys Trp Arg
                85                  90                  95

Cys Ser Arg Glu Ala Tyr Pro Asp Ser Lys Tyr Cys Glu Lys His Met
            100                 105                 110

His Arg Gly Arg Asn Arg Ala Arg Lys Ser Ile Asp Gln Asn Gln Thr
        115                 120                 125

Thr Ala Pro Leu Thr Ser Pro Ser Leu Ser Phe Pro Asn Asn Asn Asn
    130                 135                 140

Pro Ser Pro Thr Leu Ser Ser Ser Ser Ser Thr Tyr Ser Ala Ser Ser
145                 150                 155                 160

Ser Ser Pro Ser Ile Asp Ala Tyr Ser Asn Ile Asn Arg Leu Gly Val
                165                 170                 175

Gly Asn Ser Asn Ser Arg Gly Tyr Phe Asn Asn His Ser Leu Asp Tyr
            180                 185                 190

Pro Tyr Pro Leu Ser Ser Pro Lys Gln Gln Gln Gln Gln Gln Thr Leu
        195                 200                 205

His His Ala Ser Ala Leu Ser Leu His Gln Asn Ala Ser Thr Ala Ser
    210                 215                 220

Gln Phe Asn Ala Leu Ala Ser Ala Thr Asp His Lys Asp Phe Arg Tyr
225                 230                 235                 240

Phe Gln Gly Ile Gly Glu Arg Val Gly Val Gly Ala Gly Glu Arg Thr
                245                 250                 255

Phe Phe Pro Glu Ala Ser Arg Ser Phe Gln Asp Ser Pro Tyr His His
            260                 265                 270

Gln Gln Pro Leu Ala Thr Val Met Asn Asp Pro Phe His Ser Gly Thr
        275                 280                 285

Asp His Lys Val Asp His Gln His His Thr Tyr Ser Ser Val Ser Ser
    290                 295                 300

Ser Ser Gln His Asp Gln Asp His His Arg Gln Gln Gln Gln Gln Cys
305                 310                 315                 320

Phe Val Met Gly Ala Asp Met Phe Asn Lys Pro Thr Arg Thr Val Phe
                325                 330                 335

Ala Asn Ser Ser Arg Gln Asp His Gln Glu Glu Glu Glu Lys Asp Ser
            340                 345                 350

Ser Glu Thr Lys Lys Ser Leu His His Phe Phe Gly Glu Asp Trp Ala
        355                 360                 365

Gln Asn Lys Asn Ser Ser Asp Ser Trp Leu Asp Leu Ser Ser His Ser
    370                 375                 380

Arg Leu Asp Thr Gly Ser
385                 390
```

<210> SEQ ID NO 109
<211> LENGTH: 981
<212> TYPE: DNA
<213> ORGANISM: Artificial Sequence
<220> FEATURE:
<223> OTHER INFORMATION: cDNA of HaGRF5

<400> SEQUENCE: 109

```
atgatgatga tgagtactac aagcagtaac caaaatccaa atgtgttcac agcatcacaa     60

tgggaagaac tggaacagca agctttaatc tacaagtata tggtttcagg tgttccagtt    120

ccaactgatc tcatcttgtc tgtcagaaga agtttgtata acacctcagc ttcatcacta    180
```

```
tctaaccaac acacctcctc cttaggaata tgggaagctg gatcaagctt tccatacaat    240

cagttgtatc agattggtgg gtatggtggc agaaagatag atttagaacc aggaagatgc    300

agaagaacag atggaaaaaa atggaggtgc tctaaagaag cttaccccga ttcaaaatac    360

tgcgagagac acatgcacag aggtagaaac cgttcaagaa agcctgtgga attctcttct    420

tcttcttctt catcttcatc tgctgccaca agtgttaata atgtttcttc ttcatcagca    480

atctccaaat caatcgatgc ttaccctcct cctttctcaa cttttatgga ttcttcatct    540

tattctcacc aaacccttaa agattacagg cagatgcaag gaatgaagga tttaggagag    600

gatgagagat catcagcagc agcagcagct tactttcaac taaatgatcc ttacaccgcc    660

actacacaat ctggtcaaca aaactactct catttcagtt ttcaaaacct gaaagatgag    720

cagaagaagg agcaagggca gcactgtttt gtgatgggta ctgatttcat aaagccatca    780

gaagaacatg aacccaccaa atccactacc acaaaagtta atgaaaccac cagtaaacaa    840

ccattccacc acttcttttc accaccaaaa gccacactgc ttaaccctaa ccatgaccca    900

aactggggtg aagttgacca cccaaaggcc cctttgtcca cccaagacct tttccaatcc    960

aaaccaagac cttactggta g                                              981
```

```
<210> SEQ ID NO 110
<211> LENGTH: 326
<212> TYPE: PRT
<213> ORGANISM: Helianthus annuus

<400> SEQUENCE: 110

Met Met Met Met Ser Thr Thr Ser Ser Asn Gln Asn Pro Asn Val Phe
1               5                   10                  15

Thr Ala Ser Gln Trp Glu Glu Leu Glu Gln Gln Ala Leu Ile Tyr Lys
            20                  25                  30

Tyr Met Val Ser Gly Val Pro Val Pro Thr Asp Leu Ile Leu Ser Val
        35                  40                  45

Arg Arg Ser Leu Tyr Asn Thr Ser Ala Ser Ser Leu Ser Asn Gln His
    50                  55                  60

Thr Ser Ser Leu Gly Ile Trp Glu Ala Gly Ser Ser Phe Pro Tyr Asn
65                  70                  75                  80

Gln Leu Tyr Gln Ile Gly Gly Tyr Gly Gly Arg Lys Ile Asp Leu Glu
                85                  90                  95

Pro Gly Arg Cys Arg Arg Thr Asp Gly Lys Lys Trp Arg Cys Ser Lys
            100                 105                 110

Glu Ala Tyr Pro Asp Ser Lys Tyr Cys Glu Arg His Met His Arg Gly
        115                 120                 125

Arg Asn Arg Ser Arg Lys Pro Val Glu Phe Ser Ser Ser Ser Ser Ser
    130                 135                 140

Ser Ser Ser Ala Ala Thr Ser Val Asn Asn Val Ser Ser Ser Ser Ala
145                 150                 155                 160

Ile Ser Lys Ser Ile Asp Ala Tyr Pro Pro Pro Phe Ser Thr Phe Met
                165                 170                 175

Asp Ser Ser Ser Tyr Ser His Gln Thr Leu Lys Asp Tyr Arg Gln Met
            180                 185                 190

Gln Gly Met Lys Asp Leu Gly Glu Asp Glu Arg Ser Ser Ala Ala Ala
        195                 200                 205

Ala Ala Tyr Phe Gln Leu Asn Asp Pro Tyr Thr Ala Thr Thr Gln Ser
    210                 215                 220
```

```
Gly Gln Gln Asn Tyr Ser His Phe Ser Phe Gln Asn Leu Lys Asp Glu
225                 230                 235                 240

Gln Lys Lys Glu Gln Gly Gln His Cys Phe Val Met Gly Thr Asp Phe
                245                 250                 255

Ile Lys Pro Ser Glu Glu His Glu Pro Thr Lys Ser Thr Thr Thr Lys
            260                 265                 270

Val Asn Glu Thr Thr Ser Lys Gln Pro Phe His His Phe Phe Ser Pro
        275                 280                 285

Pro Lys Ala Thr Leu Leu Asn Pro Asn His Asp Pro Asn Trp Gly Glu
    290                 295                 300

Val Asp His Pro Lys Ala Pro Leu Ser Thr Gln Asp Leu Phe Gln Ser
305                 310                 315                 320

Lys Pro Arg Pro Tyr Trp
                325


<210> SEQ ID NO 111
<211> LENGTH: 1131
<212> TYPE: DNA
<213> ORGANISM: Artificial Sequence
<220> FEATURE:
<223> OTHER INFORMATION: cDNA of ZmGRF5

<400> SEQUENCE: 111

atgatgatga tgagcggtcg agcggccacc gcggggcggt acccgttcac ggcgtcgcag      60

tggcaggagc tggagcacca ggcgctcatc tacaagtgcc tggcgtccgg caagcccatc     120

ccgtcctacc tcatgccacc gctccgccgc atcctcgact ccgccctcgc cacgtcgccg     180

tcgctcgccg ccttcccgcc gcaaccctcg ctggggtggg ggggctgctt cgggatgggc     240

ttcagcagga agcccgccga cgaggacccg gagcccgggc ggtgccggcg cacggacggc     300

aagaagtggc gctgctccaa ggaggcgtac ccggactcca agtactgcga gaagcacatg     360

caccggggca agaaccgttc aagaaagcct gtggaaatgt ccttggccac gccggcgccg     420

gcctcctccg ccacaagcgc cgccgccgcc gccacctcct cgtcccaggc gccgtcctac     480

cacagcccgg cccccgccgt gccgtaccac gcgccctacg gcgccgcgta ccatcacacg     540

cagacgcagg tgacgatgag cccccttccac ctcctccacc tcgagaccac ccacccgcac     600

ccgccgccgc cgccgccgcc gccctactac tacgcggacc agagggacta cgcctacggc     660

aaggaggtcg gcgagcgcgc cttcttctcc gacggcgcgg gcgagaggga ccggcagcag     720

caggccgcgg ggcagtggca gttcaagcag ctcgggacga tggaggcgac gaagcagccg     780

tgcaccacgc cgctgctcgt ccccgccgcc gggtacggcc acggcgcggc gtcgccgtac     840

ggcgtcggtc aggccaagga agacgaggag gaggaggaaa cgcggcggca gcagcagcac     900

tgcttcgttc ttggcgccga cctgcggctg gcggagcggc cgtcgggggc acatgacgcc     960

gccgcgcaga agccgctccg gcatttcatc gacgagtggc cgcacgagaa ggggagcaat    1020

aaggcggggt cgtggatggg ggggctcgac ggcgagacga cgcagctctc catgtctatc    1080

ccgatggcgg ccgctgccga cctccccgtc acctcccgct accgtacgtg a            1131


<210> SEQ ID NO 112
<211> LENGTH: 376
<212> TYPE: PRT
<213> ORGANISM: Zea mays

<400> SEQUENCE: 112

Met Met Met Met Ser Gly Arg Ala Ala Thr Ala Gly Arg Tyr Pro Phe
1               5                   10                  15
```

```
Thr Ala Ser Gln Trp Gln Glu Leu Glu His Gln Ala Leu Ile Tyr Lys
            20                  25                  30

Cys Leu Ala Ser Gly Lys Pro Ile Pro Ser Tyr Leu Met Pro Pro Leu
        35                  40                  45

Arg Arg Ile Leu Asp Ser Ala Leu Ala Thr Ser Pro Ser Leu Ala Ala
    50                  55                  60

Phe Pro Pro Gln Pro Ser Leu Gly Trp Gly Gly Cys Phe Gly Met Gly
65                  70                  75                  80

Phe Ser Arg Lys Pro Ala Asp Glu Asp Pro Glu Pro Gly Arg Cys Arg
                85                  90                  95

Arg Thr Asp Gly Lys Lys Trp Arg Cys Ser Lys Glu Ala Tyr Pro Asp
            100                 105                 110

Ser Lys Tyr Cys Glu Lys His Met His Arg Gly Lys Asn Arg Ser Arg
        115                 120                 125

Lys Pro Val Glu Met Ser Leu Ala Thr Pro Ala Pro Ala Ser Ser Ala
    130                 135                 140

Thr Ser Ala Ala Ala Ala Ala Thr Ser Ser Ser Gln Ala Pro Ser Tyr
145                 150                 155                 160

His Ser Pro Ala Pro Ala Val Pro Tyr His Ala Pro Tyr Gly Ala Ala
                165                 170                 175

Tyr His His Thr Gln Thr Gln Val Thr Met Ser Pro Phe His Leu Leu
            180                 185                 190

His Leu Glu Thr Thr His Pro His Pro Pro Pro Pro Pro Pro Pro Pro
        195                 200                 205

Tyr Tyr Tyr Ala Asp Gln Arg Asp Tyr Ala Tyr Gly Lys Glu Val Gly
    210                 215                 220

Glu Arg Ala Phe Phe Ser Asp Gly Ala Gly Glu Arg Asp Arg Gln Gln
225                 230                 235                 240

Gln Ala Ala Gly Gln Trp Gln Phe Lys Gln Leu Gly Thr Met Glu Ala
                245                 250                 255

Thr Lys Gln Pro Cys Thr Thr Pro Leu Leu Val Pro Ala Ala Gly Tyr
            260                 265                 270

Gly His Gly Ala Ala Ser Pro Tyr Gly Val Gly Gln Ala Lys Glu Asp
        275                 280                 285

Glu Glu Glu Glu Glu Thr Arg Arg Gln Gln Gln His Cys Phe Val Leu
    290                 295                 300

Gly Ala Asp Leu Arg Leu Ala Glu Arg Pro Ser Gly Ala His Asp Ala
305                 310                 315                 320

Ala Ala Gln Lys Pro Leu Arg His Phe Ile Asp Glu Trp Pro His Glu
                325                 330                 335

Lys Gly Ser Asn Lys Ala Gly Ser Trp Met Gly Gly Leu Asp Gly Glu
            340                 345                 350

Thr Thr Gln Leu Ser Met Ser Ile Pro Met Ala Ala Ala Ala Asp Leu
        355                 360                 365

Pro Val Thr Ser Arg Tyr Arg Thr
    370                 375
```

<210> SEQ ID NO 113
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 113

```
Asp Leu Glu Pro Gly Arg Cys Arg Arg Thr Asp Gly Lys Lys Trp Arg
1               5                   10                  15

Cys Ser Arg Glu Ala Tyr Pro Asp Ser Lys Tyr Cys Glu Lys His Met
            20                  25                  30

His Arg Gly Arg Asn Arg
        35


<210> SEQ ID NO 114
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 114

Asp Leu Glu Pro Gly Arg Cys Arg Arg Thr Asp Gly Lys Lys Trp Arg
1               5                   10                  15

Cys Ala Arg Glu Ala Tyr Pro Asp Ser Lys Tyr Cys Glu Lys His Met
            20                  25                  30

His Arg Gly Arg Asn Arg
        35


<210> SEQ ID NO 115
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 115

Asp Leu Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Lys His Met
            20                  25                  30

His Arg Gly Arg Asn Arg
        35


<210> SEQ ID NO 116
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 116

Asp Leu Glu Pro Gly Arg Cys Arg Arg Thr Asp Gly Lys Lys Trp Arg
1               5                   10                  15

Cys Ala Lys Glu Ala Tyr Pro Asp Ser Lys Tyr Cys Glu Lys His Met
            20                  25                  30

His Arg Gly Arg Asn Arg
        35


<210> SEQ ID NO 117
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 117

Asp Leu Glu Pro Gly Arg Cys Arg Arg Thr Asp Gly Lys Lys Trp Arg
1               5                   10                  15
```

Cys Ser Arg Asp Ala Tyr Pro Asp Ser Lys Tyr Cys Glu Lys His Met
20 25 30

His Arg Gly Arg Asn Arg
35

<210> SEQ ID NO 118
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 118

Asp Leu Glu Pro Gly Arg Cys Arg Arg Thr Asp Gly Lys Lys Trp Arg
1 5 10 15

Cys Ala Arg Asp Ala Tyr Pro Asp Ser Lys Tyr Cys Glu Lys His Met
20 25 30

His Arg Gly Arg Asn Arg
35

<210> SEQ ID NO 119
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 119

Asp Leu Glu Pro Gly Arg Cys Arg Arg Thr Asp Gly Lys Lys Trp Arg
1 5 10 15

Cys Ser Lys Asp Ala Tyr Pro Asp Ser Lys Tyr Cys Glu Lys His Met
20 25 30

His Arg Gly Arg Asn Arg
35

<210> SEQ ID NO 120
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 120

Asp Leu Glu Pro Gly Arg Cys Arg Arg Thr Asp Gly Lys Lys Trp Arg
1 5 10 15

Cys Ala Lys Asp Ala Tyr Pro Asp Ser Lys Tyr Cys Glu Lys His Met
20 25 30

His Arg Gly Arg Asn Arg
35

<210> SEQ ID NO 121
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 121

Asp Leu Glu Pro Gly Arg Cys Arg Arg Thr Asp Gly Lys Lys Trp Arg
1 5 10 15

Cys Ser Arg Glu Ala His Pro Asp Ser Lys Tyr Cys Glu Lys His Met
20 25 30

```
His Arg Gly Arg Asn Arg
        35


<210> SEQ ID NO 122
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 122

Asp Leu Glu Pro Gly Arg Cys Arg Arg Thr Asp Gly Lys Lys Trp Arg
1               5                   10                  15

Cys Ala Arg Glu Ala His Pro Asp Ser Lys Tyr Cys Glu Lys His Met
            20                  25                  30

His Arg Gly Arg Asn Arg
        35


<210> SEQ ID NO 123
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 123

Asp Leu Glu Pro Gly Arg Cys Arg Arg Thr Asp Gly Lys Lys Trp Arg
1               5                   10                  15

Cys Ser Lys Glu Ala His Pro Asp Ser Lys Tyr Cys Glu Lys His Met
            20                  25                  30

His Arg Gly Arg Asn Arg
        35


<210> SEQ ID NO 124
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 124

Asp Leu Glu Pro Gly Arg Cys Arg Arg Thr Asp Gly Lys Lys Trp Arg
1               5                   10                  15

Cys Ala Lys Glu Ala His Pro Asp Ser Lys Tyr Cys Glu Lys His Met
            20                  25                  30

His Arg Gly Arg Asn Arg
        35


<210> SEQ ID NO 125
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 125

Asp Leu Glu Pro Gly Arg Cys Arg Arg Thr Asp Gly Lys Lys Trp Arg
1               5                   10                  15

Cys Ser Arg Asp Ala His Pro Asp Ser Lys Tyr Cys Glu Lys His Met
            20                  25                  30

His Arg Gly Arg Asn Arg
        35
```

<210> SEQ ID NO 126
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 126

Asp Leu Glu Pro Gly Arg Cys Arg Arg Thr Asp Gly Lys Lys Trp Arg
1 5 10 15

Cys Ala Arg Asp Ala His Pro Asp Ser Lys Tyr Cys Glu Lys His Met
20 25 30

His Arg Gly Arg Asn Arg
35

<210> SEQ ID NO 127
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 127

Asp Leu Glu Pro Gly Arg Cys Arg Arg Thr Asp Gly Lys Lys Trp Arg
1 5 10 15

Cys Ser Lys Asp Ala His Pro Asp Ser Lys Tyr Cys Glu Lys His Met
20 25 30

His Arg Gly Arg Asn Arg
35

<210> SEQ ID NO 128
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 128

Asp Leu Glu Pro Gly Arg Cys Arg Arg Thr Asp Gly Lys Lys Trp Arg
1 5 10 15

Cys Ala Lys Asp Ala His Pro Asp Ser Lys Tyr Cys Glu Lys His Met
20 25 30

His Arg Gly Arg Asn Arg
35

<210> SEQ ID NO 129
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 129

Asp Leu Glu Pro Gly Arg Cys Arg Arg Thr Asp Gly Lys Lys Trp Arg
1 5 10 15

Cys Ser Arg Glu Ala Tyr Pro Asp Ser Lys Tyr Cys Glu Arg His Met
20 25 30

His Arg Gly Arg Asn Arg
35

<210> SEQ ID NO 130

<211> LENGTH: 38
<212> TYPE: PRT
<213> ORGANISM: Artificial Sequence
<220> FEATURE:
<223> OTHER INFORMATION: variant of the indicator motif

<400> SEQUENCE: 130

Asp Leu Glu Pro Gly Arg Cys Arg Arg Thr Asp Gly Lys Lys Trp Arg
1               5                   10                  15

Cys Ala Arg Glu Ala Tyr Pro Asp Ser Lys Tyr Cys Glu Arg His Met
            20                  25                  30

His Arg Gly Arg Asn Arg
        35

<210> SEQ ID NO 131
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 131

Asp Leu Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Arg His Met
            20                  25                  30

His Arg Gly Arg Asn Arg
        35

<210> SEQ ID NO 132
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 132

Asp Leu Glu Pro Gly Arg Cys Arg Arg Thr Asp Gly Lys Lys Trp Arg
1               5                   10                  15

Cys Ala Lys Glu Ala Tyr Pro Asp Ser Lys Tyr Cys Glu Arg His Met
            20                  25                  30

His Arg Gly Arg Asn Arg
        35

<210> SEQ ID NO 133
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 133

Asp Leu Glu Pro Gly Arg Cys Arg Arg Thr Asp Gly Lys Lys Trp Arg
1               5                   10                  15

Cys Ser Arg Asp Ala Tyr Pro Asp Ser Lys Tyr Cys Glu Arg His Met
            20                  25                  30

His Arg Gly Arg Asn Arg
        35

<210> SEQ ID NO 134
<211> LENGTH: 38
<212> TYPE: PRT
<213> ORGANISM: Artificial Sequence

```
<220> FEATURE:
<223> OTHER INFORMATION: variant of the indicator motif

<400> SEQUENCE: 134

Asp Leu Glu Pro Gly Arg Cys Arg Arg Thr Asp Gly Lys Lys Trp Arg
1               5                   10                  15

Cys Ala Arg Asp Ala Tyr Pro Asp Ser Lys Tyr Cys Glu Arg His Met
            20                  25                  30

His Arg Gly Arg Asn Arg
        35


<210> SEQ ID NO 135
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 135

Asp Leu Glu Pro Gly Arg Cys Arg Arg Thr Asp Gly Lys Lys Trp Arg
1               5                   10                  15

Cys Ser Lys Asp Ala Tyr Pro Asp Ser Lys Tyr Cys Glu Arg His Met
            20                  25                  30

His Arg Gly Arg Asn Arg
        35


<210> SEQ ID NO 136
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 136

Asp Leu Glu Pro Gly Arg Cys Arg Arg Thr Asp Gly Lys Lys Trp Arg
1               5                   10                  15

Cys Ala Lys Asp Ala Tyr Pro Asp Ser Lys Tyr Cys Glu Arg His Met
            20                  25                  30

His Arg Gly Arg Asn Arg
        35


<210> SEQ ID NO 137
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 137

Asp Leu Glu Pro Gly Arg Cys Arg Arg Thr Asp Gly Lys Lys Trp Arg
1               5                   10                  15

Cys Ser Arg Glu Ala His Pro Asp Ser Lys Tyr Cys Glu Arg His Met
            20                  25                  30

His Arg Gly Arg Asn Arg
        35


<210> SEQ ID NO 138
<211> LENGTH: 38
<212> TYPE: PRT
<213> ORGANISM: Artificial Sequence
<220> FEATURE:
<223> OTHER INFORMATION: variant of the indicator motif
```

<400> SEQUENCE: 138

Asp Leu Glu Pro Gly Arg Cys Arg Arg Thr Asp Gly Lys Lys Trp Arg
1               5                   10                  15

Cys Ala Arg Glu Ala His Pro Asp Ser Lys Tyr Cys Glu Arg His Met
            20                  25                  30

His Arg Gly Arg Asn Arg
        35

<210> SEQ ID NO 139
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 139

Asp Leu Glu Pro Gly Arg Cys Arg Arg Thr Asp Gly Lys Lys Trp Arg
1               5                   10                  15

Cys Ser Lys Glu Ala His Pro Asp Ser Lys Tyr Cys Glu Arg His Met
            20                  25                  30

His Arg Gly Arg Asn Arg
        35

<210> SEQ ID NO 140
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 140

Asp Leu Glu Pro Gly Arg Cys Arg Arg Thr Asp Gly Lys Lys Trp Arg
1               5                   10                  15

Cys Ala Lys Glu Ala His Pro Asp Ser Lys Tyr Cys Glu Arg His Met
            20                  25                  30

His Arg Gly Arg Asn Arg
        35

<210> SEQ ID NO 141
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 141

Asp Leu Glu Pro Gly Arg Cys Arg Arg Thr Asp Gly Lys Lys Trp Arg
1               5                   10                  15

Cys Ser Arg Asp Ala His Pro Asp Ser Lys Tyr Cys Glu Arg His Met
            20                  25                  30

His Arg Gly Arg Asn Arg
        35

<210> SEQ ID NO 142
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 142

Asp Leu Glu Pro Gly Arg Cys Arg Arg Thr Asp Gly Lys Lys Trp Arg 1 5 10 15

Cys Ala Arg Asp Ala His Pro Asp Ser Lys Tyr Cys Glu Arg His Met
20 25 30

His Arg Gly Arg Asn Arg
35

<210> SEQ ID NO 143
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 143

Asp Leu Glu Pro Gly Arg Cys Arg Arg Thr Asp Gly Lys Lys Trp Arg
1 5 10 15

Cys Ser Lys Asp Ala His Pro Asp Ser Lys Tyr Cys Glu Arg His Met
20 25 30

His Arg Gly Arg Asn Arg
35

<210> SEQ ID NO 144
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 144

Asp Leu Glu Pro Gly Arg Cys Arg Arg Thr Asp Gly Lys Lys Trp Arg
1 5 10 15

Cys Ala Lys Asp Ala His Pro Asp Ser Lys Tyr Cys Glu Arg His Met
20 25 30

His Arg Gly Arg Asn Arg
35

<210> SEQ ID NO 145
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 145

Asp Leu Glu Pro Gly Arg Cys Arg Arg Thr Asp Gly Lys Lys Trp Arg
1 5 10 15

Cys Ser Arg Glu Ala Tyr Pro Asp Ser Lys Tyr Cys Glu Lys His Met
20 25 30

His Arg Gly Lys Asn Arg
35

<210> SEQ ID NO 146
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 146

Asp Leu Glu Pro Gly Arg Cys Arg Arg Thr Asp Gly Lys Lys Trp Arg
1 5 10 15

Cys Ala Arg Glu Ala Tyr Pro Asp Ser Lys Tyr Cys Glu Lys His Met 20 25 30

His Arg Gly Lys Asn Arg
35

<210> SEQ ID NO 147
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 147

Asp Leu Glu Pro Gly Arg Cys Arg Arg Thr Asp Gly Lys Lys Trp Arg
1 5 10 15

Cys Ser Lys Glu Ala Tyr Pro Asp Ser Lys Tyr Cys Glu Lys His Met
20 25 30

His Arg Gly Lys Asn Arg
35

<210> SEQ ID NO 148
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 148

Asp Leu Glu Pro Gly Arg Cys Arg Arg Thr Asp Gly Lys Lys Trp Arg
1 5 10 15

Cys Ala Lys Glu Ala Tyr Pro Asp Ser Lys Tyr Cys Glu Lys His Met
20 25 30

His Arg Gly Lys Asn Arg
35

<210> SEQ ID NO 149
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 149

Asp Leu Glu Pro Gly Arg Cys Arg Arg Thr Asp Gly Lys Lys Trp Arg
1 5 10 15

Cys Ser Arg Asp Ala Tyr Pro Asp Ser Lys Tyr Cys Glu Lys His Met
20 25 30

His Arg Gly Lys Asn Arg
35

<210> SEQ ID NO 150
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 150

Asp Leu Glu Pro Gly Arg Cys Arg Arg Thr Asp Gly Lys Lys Trp Arg
1 5 10 15

Cys Ala Arg Asp Ala Tyr Pro Asp Ser Lys Tyr Cys Glu Lys His Met
20 25 30

His Arg Gly Lys Asn Arg

35

<210> SEQ ID NO 151
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 151

Asp Leu Glu Pro Gly Arg Cys Arg Arg Thr Asp Gly Lys Lys Trp Arg
1 5 10 15

Cys Ser Lys Asp Ala Tyr Pro Asp Ser Lys Tyr Cys Glu Lys His Met
20 25 30

His Arg Gly Lys Asn Arg
35

<210> SEQ ID NO 152
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 152

Asp Leu Glu Pro Gly Arg Cys Arg Arg Thr Asp Gly Lys Lys Trp Arg
1 5 10 15

Cys Ala Lys Asp Ala Tyr Pro Asp Ser Lys Tyr Cys Glu Lys His Met
20 25 30

His Arg Gly Lys Asn Arg
35

<210> SEQ ID NO 153
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 153

Asp Leu Glu Pro Gly Arg Cys Arg Arg Thr Asp Gly Lys Lys Trp Arg
1 5 10 15

Cys Ser Arg Glu Ala His Pro Asp Ser Lys Tyr Cys Glu Lys His Met
20 25 30

His Arg Gly Lys Asn Arg
35

<210> SEQ ID NO 154
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 154

Asp Leu Glu Pro Gly Arg Cys Arg Arg Thr Asp Gly Lys Lys Trp Arg
1 5 10 15

Cys Ala Arg Glu Ala His Pro Asp Ser Lys Tyr Cys Glu Lys His Met
20 25 30

His Arg Gly Lys Asn Arg
35

<210> SEQ ID NO 155
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 155

Asp Leu Glu Pro Gly Arg Cys Arg Arg Thr Asp Gly Lys Lys Trp Arg
1 5 10 15

Cys Ser Lys Glu Ala His Pro Asp Ser Lys Tyr Cys Glu Lys His Met
20 25 30

His Arg Gly Lys Asn Arg
35

<210> SEQ ID NO 156
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 156

Asp Leu Glu Pro Gly Arg Cys Arg Arg Thr Asp Gly Lys Lys Trp Arg
1 5 10 15

Cys Ala Lys Glu Ala His Pro Asp Ser Lys Tyr Cys Glu Lys His Met
20 25 30

His Arg Gly Lys Asn Arg
35

<210> SEQ ID NO 157
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 157

Asp Leu Glu Pro Gly Arg Cys Arg Arg Thr Asp Gly Lys Lys Trp Arg
1 5 10 15

Cys Ser Arg Asp Ala His Pro Asp Ser Lys Tyr Cys Glu Lys His Met
20 25 30

His Arg Gly Lys Asn Arg
35

<210> SEQ ID NO 158
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 158

Asp Leu Glu Pro Gly Arg Cys Arg Arg Thr Asp Gly Lys Lys Trp Arg
1 5 10 15

Cys Ala Arg Asp Ala His Pro Asp Ser Lys Tyr Cys Glu Lys His Met
20 25 30

His Arg Gly Lys Asn Arg
35

<210> SEQ ID NO 159
<211> LENGTH: 38
<212> TYPE: PRT

```
<213> ORGANISM: Artificial Sequence
<220> FEATURE:
<223> OTHER INFORMATION: variant of the indicator motif

<400> SEQUENCE: 159

Asp Leu Glu Pro Gly Arg Cys Arg Arg Thr Asp Gly Lys Lys Trp Arg
1               5                   10                  15

Cys Ser Lys Asp Ala His Pro Asp Ser Lys Tyr Cys Glu Lys His Met
            20                  25                  30

His Arg Gly Lys Asn Arg
        35


<210> SEQ ID NO 160
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 160

Asp Leu Glu Pro Gly Arg Cys Arg Arg Thr Asp Gly Lys Lys Trp Arg
1               5                   10                  15

Cys Ala Lys Asp Ala His Pro Asp Ser Lys Tyr Cys Glu Lys His Met
            20                  25                  30

His Arg Gly Lys Asn Arg
        35


<210> SEQ ID NO 161
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 161

Asp Leu Glu Pro Gly Arg Cys Arg Arg Thr Asp Gly Lys Lys Trp Arg
1               5                   10                  15

Cys Ser Arg Glu Ala Tyr Pro Asp Ser Lys Tyr Cys Glu Arg His Met
            20                  25                  30

His Arg Gly Lys Asn Arg
        35


<210> SEQ ID NO 162
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 162

Asp Leu Glu Pro Gly Arg Cys Arg Arg Thr Asp Gly Lys Lys Trp Arg
1               5                   10                  15

Cys Ala Arg Glu Ala Tyr Pro Asp Ser Lys Tyr Cys Glu Arg His Met
            20                  25                  30

His Arg Gly Lys Asn Arg
        35


<210> SEQ ID NO 163
<211> LENGTH: 38
<212> TYPE: PRT
<213> ORGANISM: Artificial Sequence
<220> FEATURE:
<223> OTHER INFORMATION: variant of the indicator motif
```

<400> SEQUENCE: 163

Asp Leu Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Arg His Met
            20                  25                  30

His Arg Gly Lys Asn Arg
        35

<210> SEQ ID NO 164
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 164

Asp Leu Glu Pro Gly Arg Cys Arg Arg Thr Asp Gly Lys Lys Trp Arg
1               5                   10                  15

Cys Ala Lys Glu Ala Tyr Pro Asp Ser Lys Tyr Cys Glu Arg His Met
            20                  25                  30

His Arg Gly Lys Asn Arg
        35

<210> SEQ ID NO 165
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 165

Asp Leu Glu Pro Gly Arg Cys Arg Arg Thr Asp Gly Lys Lys Trp Arg
1               5                   10                  15

Cys Ser Arg Asp Ala Tyr Pro Asp Ser Lys Tyr Cys Glu Arg His Met
            20                  25                  30

His Arg Gly Lys Asn Arg
        35

<210> SEQ ID NO 166
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 166

Asp Leu Glu Pro Gly Arg Cys Arg Arg Thr Asp Gly Lys Lys Trp Arg
1               5                   10                  15

Cys Ala Arg Asp Ala Tyr Pro Asp Ser Lys Tyr Cys Glu Arg His Met
            20                  25                  30

His Arg Gly Lys Asn Arg
        35

<210> SEQ ID NO 167
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 167

Asp Leu Glu Pro Gly Arg Cys Arg Arg Thr Asp Gly Lys Lys Trp Arg
1 5 10 15

Cys Ser Lys Asp Ala Tyr Pro Asp Ser Lys Tyr Cys Glu Arg His Met
20 25 30

His Arg Gly Lys Asn Arg
35

<210> SEQ ID NO 168
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 168

Asp Leu Glu Pro Gly Arg Cys Arg Arg Thr Asp Gly Lys Lys Trp Arg
1 5 10 15

Cys Ala Lys Asp Ala Tyr Pro Asp Ser Lys Tyr Cys Glu Arg His Met
20 25 30

His Arg Gly Lys Asn Arg
35

<210> SEQ ID NO 169
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 169

Asp Leu Glu Pro Gly Arg Cys Arg Arg Thr Asp Gly Lys Lys Trp Arg
1 5 10 15

Cys Ser Arg Glu Ala His Pro Asp Ser Lys Tyr Cys Glu Arg His Met
20 25 30

His Arg Gly Lys Asn Arg
35

<210> SEQ ID NO 170
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 170

Asp Leu Glu Pro Gly Arg Cys Arg Arg Thr Asp Gly Lys Lys Trp Arg
1 5 10 15

Cys Ala Arg Glu Ala His Pro Asp Ser Lys Tyr Cys Glu Arg His Met
20 25 30

His Arg Gly Lys Asn Arg
35

<210> SEQ ID NO 171
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 171

Asp Leu Glu Pro Gly Arg Cys Arg Arg Thr Asp Gly Lys Lys Trp Arg
1 5 10 15

```
Cys Ser Lys Glu Ala His Pro Asp Ser Lys Tyr Cys Glu Arg His Met
            20                  25                  30

His Arg Gly Lys Asn Arg
        35


<210> SEQ ID NO 172
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 172

Asp Leu Glu Pro Gly Arg Cys Arg Arg Thr Asp Gly Lys Lys Trp Arg
1               5                   10                  15

Cys Ala Lys Glu Ala His Pro Asp Ser Lys Tyr Cys Glu Arg His Met
            20                  25                  30

His Arg Gly Lys Asn Arg
        35


<210> SEQ ID NO 173
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 173

Asp Leu Glu Pro Gly Arg Cys Arg Arg Thr Asp Gly Lys Lys Trp Arg
1               5                   10                  15

Cys Ser Arg Asp Ala His Pro Asp Ser Lys Tyr Cys Glu Arg His Met
            20                  25                  30

His Arg Gly Lys Asn Arg
        35


<210> SEQ ID NO 174
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 174

Asp Leu Glu Pro Gly Arg Cys Arg Arg Thr Asp Gly Lys Lys Trp Arg
1               5                   10                  15

Cys Ala Arg Asp Ala His Pro Asp Ser Lys Tyr Cys Glu Arg His Met
            20                  25                  30

His Arg Gly Lys Asn Arg
        35


<210> SEQ ID NO 175
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 175

Asp Leu Glu Pro Gly Arg Cys Arg Arg Thr Asp Gly Lys Lys Trp Arg
1               5                   10                  15

Cys Ser Lys Asp Ala His Pro Asp Ser Lys Tyr Cys Glu Arg His Met
            20                  25                  30
```

His Arg Gly Lys Asn Arg
35

<210> SEQ ID NO 176
<211> LENGTH: 38
<212> TYPE: PRT
<213> ORGANISM: Artificial Sequence
<220> FEATURE:
<223> OTHER INFORMATION: variant of the indicator motif

<400> SEQUENCE: 176

Asp Leu Glu Pro Gly Arg Cys Arg Arg Thr Asp Gly Lys Lys Trp Arg
1 5 10 15

Cys Ala Lys Asp Ala His Pro Asp Ser Lys Tyr Cys Glu Arg His Met
20 25 30

His Arg Gly Lys Asn Arg
35

<210> SEQ ID NO 177
<211> LENGTH: 38
<212> TYPE: PRT
<213> ORGANISM: Artificial Sequence
<220> FEATURE:
<223> OTHER INFORMATION: GRF5 specific indicator motif
<220> FEATURE:
<221> NAME/KEY: VARIANT
<222> LOCATION: (2)..(2)
<223> OTHER INFORMATION: X is proline (P) or leucine (L)
<220> FEATURE:
<221> NAME/KEY: VARIANT
<222> LOCATION: (18)..(18)
<223> OTHER INFORMATION: X is serine (S) or alanine (A)
<220> FEATURE:
<221> NAME/KEY: VARIANT
<222> LOCATION: (19)..(19)
<223> OTHER INFORMATION: X is arginine (R) or lysine (K)
<220> FEATURE:
<221> NAME/KEY: VARIANT
<222> LOCATION: (20)..(20)
<223> OTHER INFORMATION: X is glutamic acid (E) or aspartic acid (D)
<220> FEATURE:
<221> NAME/KEY: VARIANT
<222> LOCATION: (22)..(22)
<223> OTHER INFORMATION: X is tyrosine (Y) or histidine (H)
<220> FEATURE:
<221> NAME/KEY: VARIANT
<222> LOCATION: (30)..(30)
<223> OTHER INFORMATION: X is lysine (K) or arginine (R)
<220> FEATURE:
<221> NAME/KEY: VARIANT
<222> LOCATION: (36)..(36)
<223> OTHER INFORMATION: X is arginine (R) or lysine (K)

<400> SEQUENCE: 177

Asp Xaa Glu Pro Gly Arg Cys Arg Arg Thr Asp Gly Lys Lys Trp Arg
1 5 10 15

Cys Xaa Xaa Xaa Ala Xaa Pro Asp Ser Lys Tyr Cys Glu Xaa His Met
20 25 30

His Arg Gly Xaa Asn Arg
35

<210> SEQ ID NO 178
<211> LENGTH: 38
<212> TYPE: PRT
<213> ORGANISM: Arabidopsis thaliana

<400> SEQUENCE: 178

Asp Pro Glu Pro Gly Arg Cys Arg Arg Thr Asp Gly Lys Lys Trp Arg
1 5 10 15

```
Cys Ser Arg Asp Ala Val Pro Asp Gln Lys Tyr Cys Glu Arg His Ile
            20                  25                  30

Asn Arg Gly Arg His Arg
        35


<210> SEQ ID NO 179
<211> LENGTH: 38
<212> TYPE: PRT
<213> ORGANISM: Arabidopsis thaliana

<400> SEQUENCE: 179

Asp Pro Glu Pro Gly Arg Cys Arg Arg Thr Asp Gly Lys Lys Trp Arg
1               5                   10                  15

Cys Ser Arg Asp Ala Val Pro Asp Gln Lys Tyr Cys Glu Arg His Ile
            20                  25                  30

Asn Arg Gly Arg His Arg
        35


<210> SEQ ID NO 180
<211> LENGTH: 38
<212> TYPE: PRT
<213> ORGANISM: Arabidopsis thaliana

<400> SEQUENCE: 180

Asp Pro Glu Pro Gly Arg Cys Arg Arg Thr Asp Gly Lys Lys Trp Arg
1               5                   10                  15

Cys Ser Arg Asp Val Phe Ala Gly His Lys Tyr Cys Glu Arg His Met
            20                  25                  30

His Arg Gly Arg Asn Arg
        35


<210> SEQ ID NO 181
<211> LENGTH: 38
<212> TYPE: PRT
<213> ORGANISM: Arabidopsis thaliana

<400> SEQUENCE: 181

Asp Pro Glu Pro Gly Arg Cys Lys Arg Thr Asp Gly Lys Lys Trp Arg
1               5                   10                  15

Cys Ser Arg Asp Val Val Ala Gly His Lys Tyr Cys Asp Arg His Ile
            20                  25                  30

His Arg Gly Arg Asn Arg
        35


<210> SEQ ID NO 182
<211> LENGTH: 38
<212> TYPE: PRT
<213> ORGANISM: Arabidopsis thaliana

<400> SEQUENCE: 182

Asp Ala Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Arg His Met
            20                  25                  30

His Arg Gly Lys Asn Arg
        35


<210> SEQ ID NO 183
<211> LENGTH: 38
<212> TYPE: PRT
```

<213> ORGANISM: Arabidopsis thaliana

<400> SEQUENCE: 183

Asp Leu Glu Pro Gly Arg Cys Arg Arg Thr Asp Gly Lys Lys Trp Arg
1               5                   10                  15

Cys Ala Lys Glu Val Val Ser Asn His Lys Tyr Cys Glu Lys His Leu
            20                  25                  30

His Arg Gly Arg Pro Arg
        35

<210> SEQ ID NO 184
<211> LENGTH: 38
<212> TYPE: PRT
<213> ORGANISM: Arabidopsis thaliana

<400> SEQUENCE: 184

Asp Leu Glu Pro Trp Arg Cys Lys Arg Thr Asp Gly Lys Lys Trp Arg
1               5                   10                  15

Cys Ser Arg Asn Val Ile Pro Asp Gln Lys Tyr Cys Glu Arg His Thr
            20                  25                  30

His Lys Ser Arg Pro Arg
        35

<210> SEQ ID NO 185
<211> LENGTH: 38
<212> TYPE: PRT
<213> ORGANISM: Arabidopsis thaliana

<400> SEQUENCE: 185

Glu Thr Glu Pro Thr Arg Cys Arg Arg Thr Asp Gly Lys Lys Trp Arg
1               5                   10                  15

Cys Ser Asn Thr Val Leu Leu Phe Glu Lys Tyr Cys Glu Arg His Met
            20                  25                  30

His Arg Gly Arg Lys Arg
        35

<210> SEQ ID NO 186
<211> LENGTH: 38
<212> TYPE: PRT
<213> ORGANISM: Arabidopsis thaliana

<400> SEQUENCE: 186

Asp Pro Glu Pro Gly Arg Cys Arg Arg Thr Asp Gly Lys Lys Trp Arg
1               5                   10                  15

Cys Ser Arg Glu Ala Tyr Pro Asp Ser Lys Tyr Cys Glu Lys His Met
            20                  25                  30

His Arg Gly Arg Asn Arg
        35

<210> SEQ ID NO 187
<211> LENGTH: 38
<212> TYPE: PRT
<213> ORGANISM: Beta vulgaris

<400> SEQUENCE: 187

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Arg His Met
            20                  25                  30

His Arg Gly Lys Asn Arg

```
        35


<210> SEQ ID NO 188
<211> LENGTH: 38
<212> TYPE: PRT
<213> ORGANISM: Zea mays

<400> SEQUENCE: 188

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Lys His Met
            20                  25                  30

His Arg Gly Lys Asn Arg
        35


<210> SEQ ID NO 189
<211> LENGTH: 38
<212> TYPE: PRT
<213> ORGANISM: Triticum aestivum

<400> SEQUENCE: 189

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Lys His Met
            20                  25                  30

His Arg Gly Lys Asn Arg
        35


<210> SEQ ID NO 190
<211> LENGTH: 38
<212> TYPE: PRT
<213> ORGANISM: Brassica napus

<400> SEQUENCE: 190

Asp Pro Glu Pro Gly Arg Cys Arg Arg Thr Asp Gly Lys Lys Trp Arg
1               5                   10                  15

Cys Ser Arg Glu Ala Tyr Pro Asp Ser Lys Tyr Cys Glu Lys His Met
            20                  25                  30

His Arg Gly Arg Asn Arg
        35


<210> SEQ ID NO 191
<211> LENGTH: 38
<212> TYPE: PRT
<213> ORGANISM: Brassica rapa

<400> SEQUENCE: 191

Asp Pro Glu Pro Gly Arg Cys Arg Arg Thr Asp Gly Lys Lys Trp Arg
1               5                   10                  15

Cys Ser Arg Glu Ala His Pro Asp Ser Lys Tyr Cys Glu Lys His Met
            20                  25                  30

His Arg Gly Arg Asn Arg
        35


<210> SEQ ID NO 192
<211> LENGTH: 38
<212> TYPE: PRT
<213> ORGANISM: Brassica oleracea

<400> SEQUENCE: 192

Asp Pro Glu Pro Gly Arg Cys Arg Arg Thr Asp Gly Lys Lys Trp Arg
```

```
1               5                   10                  15

Cys Ser Arg Glu Ala Tyr Pro Asp Ser Lys Tyr Cys Glu Lys His Met
            20                  25                  30

His Arg Gly Arg Asn Arg
        35


<210> SEQ ID NO 193
<211> LENGTH: 38
<212> TYPE: PRT
<213> ORGANISM: Raphanus sativus

<400> SEQUENCE: 193

Asp Pro Glu Pro Gly Arg Cys Arg Arg Thr Asp Gly Lys Lys Trp Arg
1               5                   10                  15

Cys Ser Arg Glu Ala Tyr Pro Asp Ser Lys Tyr Cys Glu Lys His Met
            20                  25                  30

His Arg Gly Arg Asn Arg
        35


<210> SEQ ID NO 194
<211> LENGTH: 38
<212> TYPE: PRT
<213> ORGANISM: Sorghum bicolor

<400> SEQUENCE: 194

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Lys His Met
            20                  25                  30

His Arg Gly Lys Asn Arg
        35


<210> SEQ ID NO 195
<211> LENGTH: 38
<212> TYPE: PRT
<213> ORGANISM: Helianthus annuus

<400> SEQUENCE: 195

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Arg His Met
            20                  25                  30

His Arg Gly Arg Asn Arg
        35


<210> SEQ ID NO 196
<211> LENGTH: 38
<212> TYPE: PRT
<213> ORGANISM: Solanum tuberosum

<400> SEQUENCE: 196

Asp Pro Glu Pro Gly Arg Cys Arg Arg Thr Asp Gly Lys Lys Trp Arg
1               5                   10                  15

Cys Ala Lys Asp Ala Tyr Pro Asp Ser Lys Tyr Cys Glu Arg His Met
            20                  25                  30

His Arg Gly Arg Asn Arg
        35


<210> SEQ ID NO 197
<211> LENGTH: 38
```

<212> TYPE: PRT
<213> ORGANISM: Hordeum vulgare

<400> SEQUENCE: 197

Asp Pro Glu Pro Gly Arg Cys Arg Arg Thr Asp Gly Lys Lys Trp Arg
1               5                   10                  15

Cys Ser Arg Glu Ala Tyr Pro Asp Ser Lys Tyr Cys Glu Lys His Met
            20                  25                  30

His Arg Gly Lys Asn Arg
        35

<210> SEQ ID NO 198
<211> LENGTH: 38
<212> TYPE: PRT
<213> ORGANISM: Secale cereale

<400> SEQUENCE: 198

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Lys His Met
            20                  25                  30

His Arg Gly Lys Asn Arg
        35

<210> SEQ ID NO 199
<211> LENGTH: 38
<212> TYPE: PRT
<213> ORGANISM: Glycine max

<400> SEQUENCE: 199

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Arg His Met
            20                  25                  30

His Arg Gly Arg Asn Arg
        35

<210> SEQ ID NO 200
<211> LENGTH: 38
<212> TYPE: PRT
<213> ORGANISM: Gossypium hirsutum

<400> SEQUENCE: 200

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Arg His Met
            20                  25                  30

His Arg Gly Arg Asn Arg
        35

<210> SEQ ID NO 201
<211> LENGTH: 38
<212> TYPE: PRT
<213> ORGANISM: Oryza sativa

<400> SEQUENCE: 201

Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Lys His Met
            20                  25                  30

His Arg Gly Lys Asn Arg
35

<210> SEQ ID NO 202
<211> LENGTH: 38
<212> TYPE: PRT
<213> ORGANISM: Glycine max

<400> SEQUENCE: 202

Asp Pro Glu Pro Gly Arg Cys Arg Arg Thr Asp Gly Lys Lys Trp Arg
1 5 10 15

Cys Ser Lys Glu Ala Tyr Pro Asp Ser Lys Tyr Cys Glu Arg His Met
20 25 30

His Arg Gly Arg Asn Arg
35

<210> SEQ ID NO 203
<211> LENGTH: 38
<212> TYPE: PRT
<213> ORGANISM: Brassica napus

<400> SEQUENCE: 203

Asp Pro Glu Pro Gly Arg Cys Arg Arg Thr Asp Gly Lys Lys Trp Arg
1 5 10 15

Cys Ser Arg Glu Ala Tyr Pro Asp Ser Lys Tyr Cys Glu Lys His Met
20 25 30

His Arg Gly Arg Asn Arg
35

<210> SEQ ID NO 204
<211> LENGTH: 38
<212> TYPE: PRT
<213> ORGANISM: Helianthus annuus

<400> SEQUENCE: 204

Asp Leu Glu Pro Gly Arg Cys Arg Arg Thr Asp Gly Lys Lys Trp Arg
1 5 10 15

Cys Ser Lys Glu Ala Tyr Pro Asp Ser Lys Tyr Cys Glu Arg His Met
20 25 30

His Arg Gly Arg Asn Arg
35

<210> SEQ ID NO 205
<211> LENGTH: 38
<212> TYPE: PRT
<213> ORGANISM: Zea mays

<400> SEQUENCE: 205

Asp Pro Glu Pro Gly Arg Cys Arg Arg Thr Asp Gly Lys Lys Trp Arg
1 5 10 15

Cys Ser Lys Glu Ala Tyr Pro Asp Ser Lys Tyr Cys Glu Lys His Met
20 25 30

His Arg Gly Lys Asn Arg
35

<210> SEQ ID NO 206
<211> LENGTH: 38
<212> TYPE: PRT
<213> ORGANISM: Zea mays

<400> SEQUENCE: 206

```
Asp Pro Glu Pro Gly Arg Cys Arg Arg Thr Asp Gly Lys Lys Trp Arg
1               5                   10                  15

Cys Ser Lys Glu Ala Tyr Pro Asp Ser Lys Tyr Cys Glu Lys His Met
            20                  25                  30

His Arg Gly Lys Asn Arg
        35
```

<210> SEQ ID NO 207
<211> LENGTH: 1143
<212> TYPE: DNA
<213> ORGANISM: Artificial Sequence
<220> FEATURE:
<223> OTHER INFORMATION: synthetic DNA encoding BvGRF5 protein of SEQ ID NO: 4

<400> SEQUENCE: 207

```
atgtctactg ctacagctac tgttggaggc ggaggtggtg gtggaagatc taagtttcct     60

ttcacggcga cccaatggca agagcttgaa catcaggctc tcatctacaa gtacatggct    120

gctggtgtgc ctattcctcc tgatctcttg ttcaccatca agcgtagcct cgacagcagc    180

ctctcttcta aactcttccc ataccagcct tcaccgcttg gatggaaccc ttaccaaatg    240

ggatacggga agaagatcga tcctgagcct ggaagatgta ggcgtaccga tggaaaaaag    300

tggcgttgca gcaaagaggc ttacccggat tctaagtact gcgagagaca catgcaccgt    360

gggaagaaca gatctaggaa gcctgttgag tctccgctca ctactacttc taccaccgtg    420

tcgaacaata acaacaacaa caacaataac aacaactccg ccgccaactc ctctctcact    480

gttgctgctg ctgcagctgc cgcttctctt actaatcagt cactcctcaa caagaacccg    540

tcctccgtgt ctactagcct tttcagcctt ccgtcctctg acagctcttg caactctcat    600

cttctctacc cgcactccag ctacaaccac aaggattaca gagagaggta ctaccagggg    660

ctcaaagaag aagttggaga gcacgccttc ttcaccgagt catctggatc ttctatgcgt    720

gggttcagcg ggtcatctat ggatgagtct tggcaaatcg gcggagggtc taacatcgat    780

catcatcaac agcaacagca gcagtccaag cagtctggtg gataccctaa ctaccttcag    840

cagctccagt ctaacagcac cacctctaac aacggaacca gcgctaagca agagaagcag    900

tgttacatct ggggccgtga tttcaactgc gacctctcta tgaaggtcga agaggaacgt    960

gagaacttcc acgaaaagac gacccaccac ttcttcgatg agtggcctat caaatctggt   1020

ggacgtggtg gtagggattc ttcttggcac gatagcagct ctactaccca gctctctatc   1080

agcatcccgt cctctacttc tcatcaccac gactttttct tgaccaactc gcgagacagc   1140

tga                                                                 1143
```

<210> SEQ ID NO 208
<211> LENGTH: 1206
<212> TYPE: DNA
<213> ORGANISM: Artificial Sequence
<220> FEATURE:
<223> OTHER INFORMATION: synthetic DNA encoding ZmGRF5 protein according to SEQ ID NO: 209

<400> SEQUENCE: 208

```
atgatgatga tgtcatctgg tagagctggc ggcggtgcta ccgctggtag atacccattc     60

accgccagcc agtggcaaga gcttgagcac caggcgctga tctacaagtg cctggctagc    120

ggcaagccga ttccgagcta cctgatgcca ccactgaggc gcatcctgga ctctgctctg    180

gctacctctc caagcctggc ttacccacca cagccatctc ttggttgggg ctgcttcggc    240
```

```
atgggcttca ctagaaaggc tgacgaggat ccagagcctg gtaggtgcag aaggaccgac    300

ggtaagaagt ggcgctgcag caaagaggct tacccggaca gcaagtactg cgagaagcac    360

atgcacaggg gcaagaacag gtcccgcaag ccagttgaga tgagcctcgc tactcctgct    420

ccggcaccag ctccagctgc tgctactacc gctactgcta ccagctctcc ggctccatct    480

taccacaggc cagctcacga tgctacccca tctccatacc acgctctgta cggcggaggc    540

ggtggtggcg gtggctctcc ttactctgct tctgctaggc caggcgctac aggtggtggt    600

ggggcttacc atcatgctca gcacgtgagc ccattccacc tccacctcga gactacccat    660

ccgcatcctc cgccgccata caactactct gctgaccaga gggactacgc ctacggccat    720

gcagctgcta aagaggttgg cgagcacgcc ttcttctctg atggtgctgg tgagagggtt    780

gacaggcagg ctgctgctgg ccaatggcag ttcaggcaac tgggcgtcga gactaagccg    840

ggtccaactc cactgttccc agttgctggc tacggtcacg gtgctgcttc tccatacggc    900

gttgagatgg gcaaagacga cgacgagcaa gaggaaaggc gcaggcagca ttgcttcgtg    960

cttggcgctg acctgaggct cgagaggcca tcttctggtc acggccacgg ccatgaccac   1020

gatgatgccg ctgctgctca gaagccactc aggccattct tcgacgagtg gccacaccag   1080

aagggcgaca aggctggttc ttggatgggc ctcgatggcg agactcagct gtccatgagc   1140

atcccaatgg ccgctaccga tctgccagtg acctctaggt ttaggaacgg cggccactac   1200

gagtga                                                               1206
```

<210> SEQ ID NO 209
<211> LENGTH: 401
<212> TYPE: PRT
<213> ORGANISM: Zea mays

<400> SEQUENCE: 209

```
Met Met Met Met Ser Ser Gly Arg Ala Gly Gly Gly Ala Thr Ala Gly
1               5                   10                  15

Arg Tyr Pro Phe Thr Ala Ser Gln Trp Gln Glu Leu Glu His Gln Ala
            20                  25                  30

Leu Ile Tyr Lys Cys Leu Ala Ser Gly Lys Pro Ile Pro Ser Tyr Leu
        35                  40                  45

Met Pro Pro Leu Arg Arg Ile Leu Asp Ser Ala Leu Ala Thr Ser Pro
    50                  55                  60

Ser Leu Ala Tyr Pro Pro Gln Pro Ser Leu Gly Trp Gly Cys Phe Gly
65                  70                  75                  80

Met Gly Phe Thr Arg Lys Ala Asp Glu Asp Pro Glu Pro Gly Arg Cys
                85                  90                  95

Arg Arg Thr Asp Gly Lys Lys Trp Arg Cys Ser Lys Glu Ala Tyr Pro
            100                 105                 110

Asp Ser Lys Tyr Cys Glu Lys His Met His Arg Gly Lys Asn Arg Ser
        115                 120                 125

Arg Lys Pro Val Glu Met Ser Leu Ala Thr Pro Ala Pro Ala Pro Ala
    130                 135                 140

Pro Ala Ala Ala Thr Thr Ala Thr Ala Thr Ser Ser Pro Ala Pro Ser
145                 150                 155                 160

Tyr His Arg Pro Ala His Asp Ala Thr Pro Ser Pro Tyr His Ala Leu
                165                 170                 175

Tyr Gly Gly Gly Gly Gly Gly Gly Gly Ser Pro Tyr Ser Ala Ser Ala
            180                 185                 190

Arg Pro Gly Ala Thr Gly Gly Gly Gly Ala Tyr His His Ala Gln His
```

```
        195                 200                 205

Val Ser Pro Phe His Leu His Leu Glu Thr Thr His Pro His Pro Pro
    210                 215                 220

Pro Pro Tyr Asn Tyr Ser Ala Asp Gln Arg Asp Tyr Ala Tyr Gly His
225                 230                 235                 240

Ala Ala Ala Lys Glu Val Gly Glu His Ala Phe Phe Ser Asp Gly Ala
                245                 250                 255

Gly Glu Arg Val Asp Arg Gln Ala Ala Ala Gly Gln Trp Gln Phe Arg
            260                 265                 270

Gln Leu Gly Val Glu Thr Lys Pro Gly Pro Thr Pro Leu Phe Pro Val
        275                 280                 285

Ala Gly Tyr Gly His Gly Ala Ala Ser Pro Tyr Gly Val Glu Met Gly
    290                 295                 300

Lys Asp Asp Asp Glu Gln Glu Glu Arg Arg Arg Gln His Cys Phe Val
305                 310                 315                 320

Leu Gly Ala Asp Leu Arg Leu Glu Arg Pro Ser Ser Gly His Gly His
                325                 330                 335

Gly His Asp His Asp Asp Ala Ala Ala Ala Gln Lys Pro Leu Arg Pro
            340                 345                 350

Phe Phe Asp Glu Trp Pro His Gln Lys Gly Asp Lys Ala Gly Ser Trp
        355                 360                 365

Met Gly Leu Asp Gly Glu Thr Gln Leu Ser Met Ser Ile Pro Met Ala
    370                 375                 380

Ala Thr Asp Leu Pro Val Thr Ser Arg Phe Arg Asn Gly Gly His Tyr
385                 390                 395                 400

Glu
```

<210> SEQ ID NO 210
<211> LENGTH: 1131
<212> TYPE: DNA
<213> ORGANISM: Artificial Sequence
<220> FEATURE:
<223> OTHER INFORMATION: synthetic DNA encoding ZmGRF5 protein of SEQ ID NO: 6

<400> SEQUENCE: 210

```
atgatgatga tgtctggcag ggctgctacc gccggcagat acccattcac tgctagccag     60

tggcaagagc ttgagcacca ggcgctgatc tacaagtgcc tggctagcgg caagccgatt    120

ccgagctacc tgatgccacc actgaggcgc atcctggact ctgctctggc tacctctcca    180

agcctggctg cttttccacc acagccatct cttggttggg gcggctgctt cggtatgggc    240

ttttctagga agccagccga cgaggatcca gagcctggta gatgtagaag gaccgacggc    300

aagaagtggc gctgcagcaa agaggcttac ccggacagca agtactgcga gaagcacatg    360

cacaggggca agaacaggtc ccgcaagcca gttgagatga gcctggctac tccagctcca    420

gctagcagcg ctacatcagc cgctgctgct gctacttcta gctctcaggc cccgtcctac    480

cattcaccgg ctccagctgt tccataccac gctccatacg gcgctgccta ccaccatact    540

cagacccagg tgaccatgtc tccgttccat ctgctgcacc tcgagactac ccatccgcat    600

cctccgcctc cgccacctcc accatattac tacgctgacc agagggacta cgcctacggc    660

aaagaggttg gcgagagggc cttcttctct gatggtgctg gtgagaggga tcgccagcaa    720

caagctgctg gccaatggca gttcaagcag ctgggcacca tggaagccac caagcagcca    780

tgcactaccc cactgcttgt gccagctgct ggttacggtc atggcgccgc ttcaccatac    840
```

-continued

| | |
|---|---|
| ggtgttggcc aggctaaaga ggacgaggaa gaagaggaaa ccaggcgcca gcagcaacac | 900 |
| tgcttcgtgc tgggtgctga tctgaggctt gccgagaggc catctggcgc tcatgatgcc | 960 |
| gctgctcaga agccactcag gcacttcatt gacgagtggc cgcacgagaa gggctctaac | 1020 |
| aaggctggct cttggatggg cggcctggat ggcgagacta ctcagctgtc tatgagcatc | 1080 |
| ccaatggccg ctgccgctga tctgccagtg acttctaggt acaggacctg a | 1131 |